(12) United States Patent
Dejima

(10) Patent No.: US 9,308,049 B2
(45) Date of Patent: Apr. 12, 2016

(54) MEDICAL TREATMENT ENDOSCOPE

(75) Inventor: Takumi Dejima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1077 days.

(21) Appl. No.: 12/024,704

(22) Filed: Feb. 1, 2008

(65) Prior Publication Data

US 2008/0287737 A1    Nov. 20, 2008

Related U.S. Application Data

(63) Continuation-in-part of application No. 11/809,488, filed on Jun. 1, 2007, now Pat. No. 8,021,293, which is a continuation-in-part of application No. 11/652,880, filed on Jan. 12, 2007, now Pat. No. 8,444,547, which is a continuation-in-part of application No. 11/435,183, filed on May 16, 2006, now Pat. No. 8,617,054, which is a continuation-in-part of application No. 11/331,963, filed on Jan. 13, 2006, now Pat. No. 8,092,371.

(51) Int. Cl.
| | | |
|---|---|---|
| *A61B 1/00* | (2006.01) | |
| *A61B 1/04* | (2006.01) | |
| *A61B 17/00* | (2006.01) | |
| *A61B 19/00* | (2006.01) | |
| *A61B 17/29* | (2006.01) | |
| *A61B 18/14* | (2006.01) | |

(52) U.S. Cl.
CPC ........ *A61B 19/2203* (2013.01); *A61B 17/00234* (2013.01); *A61B 17/29* (2013.01); *A61B 18/1492* (2013.01); *A61B 2017/2905* (2013.01); *A61B 2017/2906* (2013.01); *A61B 2017/2927* (2013.01); *A61B 2019/2211* (2013.01); *A61B 2019/2223* (2013.01)

(58) Field of Classification Search
USPC ......... 600/104, 106, 114, 118, 132, 139–154, 600/107, 115, 127, 129, 131; 606/1, 606/205–209; 604/528
See application file for complete search history.

(56) References Cited

U.S. PATENT DOCUMENTS

| 4,245,624 A | 1/1981 | Komiya ........................ 600/106 |
| 4,577,621 A | 3/1986 | Patel |

(Continued)

FOREIGN PATENT DOCUMENTS

| CN | 1602166 A | 3/2005 |
| CN | 1886087 A | 12/2006 |

(Continued)

OTHER PUBLICATIONS

U.S. Office Action dated Feb. 1, 2011 received in related U.S. Appl. No. 11/809,488.

(Continued)

*Primary Examiner* — Ryan Henderson
(74) *Attorney, Agent, or Firm* — Scully, Scott, Murphy & Presser, P.C.

(57) ABSTRACT

A medical treatment endoscope includes: a flexible sheath capable of a bending operation; a viewing unit for observing the vicinity of the tip relative to the sheath; an arm section protruding from the tip of the sheath and capable of bending operation; an operation section for operating the arm section; and at least a transmission member, connected to the arm section and the operation section, for transmitting the operation of the operation section to the arm section. The transmission member is detachably connected to the operation section.

9 Claims, 40 Drawing Sheets

(56) References Cited

U.S. PATENT DOCUMENTS

| | | | |
|---|---|---|---|
| 4,873,965 A | 10/1989 | Danieli | |
| 5,173,716 A | 12/1992 | Tetsuka | 343/903 |
| 5,217,114 A | 6/1993 | Gadberry et al. | |
| 5,299,559 A | 4/1994 | Bruce et al. | 600/141 |
| 5,318,013 A | 6/1994 | Wilk | |
| 5,395,367 A | 3/1995 | Wilk | |
| 5,448,989 A | 9/1995 | Heckele | |
| 5,683,349 A | 11/1997 | Makower et al. | |
| 5,855,569 A | 1/1999 | Komi | 604/526 |
| 5,916,147 A | 6/1999 | Boury | |
| 5,976,075 A | 11/1999 | Beane et al. | |
| 6,013,024 A | 1/2000 | Mitsuda et al. | |
| 6,352,503 B1 | 3/2002 | Matsui et al. | |
| 6,780,151 B2 | 8/2004 | Grabover et al. | |
| 7,833,156 B2 | 11/2010 | Williams et al. | |
| 2002/0087048 A1 | 7/2002 | Brock et al. | 600/114 |
| 2004/0044270 A1 | 3/2004 | Barry | |
| 2004/0117032 A1 | 6/2004 | Roth | |
| 2004/0138525 A1 | 7/2004 | Saadat et al. | |
| 2004/0138529 A1 | 7/2004 | Wiltshire et al. | |
| 2004/0193212 A1 | 9/2004 | Taniguchi et al. | |
| 2005/0065397 A1 | 3/2005 | Saadat et al. | |
| 2005/0075538 A1 | 4/2005 | Banik et al. | |
| 2005/0090709 A1 | 4/2005 | Okada et al. | 600/106 |
| 2005/0119522 A1 | 6/2005 | Okada | 600/106 |
| 2005/0222495 A1 | 10/2005 | Okada et al. | |
| 2005/0228224 A1 | 10/2005 | Okada et al. | |
| 2005/0234294 A1 | 10/2005 | Saadat et al. | |
| 2005/0234296 A1 | 10/2005 | Saadat et al. | |
| 2005/0250989 A1 | 11/2005 | Suzuki et al. | |
| 2005/0273085 A1 | 12/2005 | Hinman et al. | 606/1 |
| 2006/0111615 A1 | 5/2006 | Danitz et al. | |
| 2006/0189845 A1 | 8/2006 | Maahs et al. | |
| 2007/0004967 A1 | 1/2007 | Ueno et al. | |
| 2007/0043338 A1* | 2/2007 | Moll et al. | 606/1 |
| 2007/0156019 A1 | 7/2007 | Larkin et al. | |
| 2007/0167679 A1 | 7/2007 | Miyamoto et al. | |
| 2007/0167680 A1 | 7/2007 | Miyamoto et al. | |
| 2007/0232856 A1 | 10/2007 | Ueno et al. | |
| 2007/0270640 A1 | 11/2007 | Dimitriou et al. | |
| 2007/0299387 A1 | 12/2007 | Williams et al. | |
| 2008/0051631 A1 | 2/2008 | Dejima et al. | |
| 2008/0065109 A1* | 3/2008 | Larkin | 606/130 |
| 2008/0221391 A1 | 9/2008 | Weitzner et al. | 600/118 |
| 2008/0262294 A1 | 10/2008 | Ewers et al. | |

FOREIGN PATENT DOCUMENTS

| | | |
|---|---|---|
| EP | 1 872 709 A1 | 1/2008 |
| EP | 1 967 123 A1 | 9/2008 |
| JP | 55-45436 | 3/1980 |
| JP | 56-104501 | 8/1981 |
| JP | 63-102401 | 7/1988 |
| JP | S63-242217 | 10/1988 |
| JP | 5-5105 U | 1/1993 |
| JP | 5-49594 | 3/1993 |
| JP | 8-131441 | 5/1996 |
| JP | 08322787 A | 12/1996 |
| JP | 10-258022 | 9/1998 |
| JP | 11-318815 A | 11/1999 |
| JP | 2001-46393 A | 2/2001 |
| JP | 2002-253563 A | 9/2002 |
| JP | 2004-180781 | 7/2004 |
| JP | 2004-290569 | 10/2004 |
| JP | 2005261688 A | 9/2005 |
| JP | 2005-287963 | 10/2005 |
| JP | 2005-296412 | 10/2005 |
| JP | 2006-141624 | 6/2006 |
| JP | 2006-516910 | 7/2006 |
| JP | 2006-516910 A | 7/2006 |
| JP | 2007-151595 | 6/2007 |
| JP | 2007-175070 | 7/2007 |
| JP | 2007-275624 | 10/2007 |
| WO | WO 2004/064600 A2 | 8/2004 |
| WO | 2005/009227 A1 | 2/2005 |
| WO | WO 2007/057880 A2 | 5/2007 |
| WO | WO 2007/074571 A1 | 7/2007 |
| WO | WO 2007/080974 A1 | 7/2007 |
| WO | WO 2007/127199 A1 | 11/2007 |

OTHER PUBLICATIONS

U.S. Office Action dated Mar. 2, 2011 received in related U.S. Appl. No. 11/652,880.
U.S. Office Action dated Mar. 16, 2011 received in related U.S. Appl. No. 11/435,183.
U.S. Office Action dated Jul. 9, 2010.
U.S. Office Action dated Mar. 24, 2010, received in related U.S. Appl. No. 11/435,183.
U.S. Office Action dated Nov. 30, 2011 of related received in related U.S. Appl. No. 12/057,990.
Office Action dated Oct. 5, 2011 from corresponding U.S. Appl. No. 11/652,880.
U.S. Office Action dated Mar. 28, 2012 of related U.S. Appl. No. 13/212,610.
Extended Supplementary European Search Report dated Jul. 18, 2014 from related European Application No. 07 70 6679.3.
U.S. Office Action mailed May 31, 2012 in related U.S. Appl. No. 12/024,704.
U.S. Office Action mailed Jun. 26, 2012 in related U.S. Appl. No. 12/058,029.
U.S. Office Action mailed Jul. 2, 2012 in related U.S. Appl. No. 12/057,990.
U.S. Office Action mailed Jul. 3, 2012 in related U.S. Appl. No. 12/035,535.
Japanese Notice of Allowance dated Aug. 20, 2013 issued in corresponding Application No. 2009-058066 with English language Translation.
U.S. Office Action dated Mar. 19, 2013 issued in corresponding U.S. Appl. No. 12/058,029.
U.S. Office Action dated May 15, 2012 received in related U.S. Appl. No. 11/652,880.
Japanese Notice of Allowance dated Jun. 4, 2013 issued in corresponding Application No. 2009-013615 together with an English Language Translation.
Chinese Office Action dated Jul. 3, 2012 from related Chinese Patent Application Publication No. 2007-80008372.7, together with an English language translation.
Japanese Office Action (Notice of Reasons for Rejection) dated Dec. 18, 2012 from corresponding Japanese Patent Application Publication No. JP 2009-013615, together with an English language translation.
Japanese Office Action (Notice of Reasons for Rejection) dated Dec. 18, 2012 from corresponding Japanese Patent Application Publication No. JP 2009-027835, together with an English language translation.
Japanese Office Action (Notice of Reasons for Rejection) dated Dec. 18, 2012 from corresponding Japanese Patent Application Publication No. JP 2009-033278, together with an English language translation.
U.S. Office Action mailed Jun. 6, 2012 in related U.S. Appl. No. 12/127,449.
Japanese Office Action dated Feb. 19, 2013 together with an English Translation issued in corresponding Japanese Application No. 2009-058066.
Notice of Allowance dated Jan. 22, 2013 issued in corresponding U.S. Appl. No. 11/652,880.
Office Action dated Dec. 16, 2014 received in related U.S. Patent Application, namely U.S. Appl. No. 12/035,535.

* cited by examiner

MEDICAL TREATMENT ENDOSCOPE

CROSS REFERENCE TO RELATED APPLICATIONS

This is a Continuation In-part Application (CIP) based on U.S. patent application Ser. No. 11/809,488, titled "MEDICAL TREATMENT ENDOSCOPE", filed Jun. 1, 2007, which is a CIP based on U.S. patent application Ser. No. 11/652,880, titled "MEDICAL TREATMENT ENDOSCOPE", filed Jan. 12, 2007, which is a CIP based on U.S. patent application Ser. No. 11/435,183, titled "MEDICAL TREATMENT ENDOSCOPE", filed May 16, 2006, which is a CIP based on U.S. patent application Ser. No. 11/331,963, titled "MEDICAL TREATMENT ENDOSCOPE", filed Jan. 13, 2006.

BACKGROUND OF THE INVENTION

1. Field of the Invention

The present invention relates to an endoscope apparatus.

2. Background Art

Laparoscopic surgery is a conventionally known technique that has been employed when performing a medical procedure such as observation or treatment of the internal organs of the human body. Rather than making a large abdominal incision, laparoscopic surgery provides for the procedure to be carried out by making several openings in the abdominal wall, and inserting a laparoscope and surgical instruments such as forceps into these respective openings. This type of surgery offers the benefit of being less invasive on the patient, since only small openings are made in the abdominal wall.

As a method of even further reducing stress on the patient, it has been proposed in recent years to carry out medical procedures by inserting a flexible endoscope into the patient via a natural opening such as the mouth, nostrils or anus. An example of a medical treatment endoscope used in such procedures is disclosed in U.S. Patent Application Publication No. 2005/0065397.

In the medical treatment endoscope disclosed in this reference, arm members that have a bendable end are respectively inserted into a plurality of lumens disposed within a flexible inserted part that is inserted into the body via the mouth of the patient. By inserting respective instruments through these arm members, the procedure site of interest can be approached from different directions with the various instruments. Accordingly, a plurality of procedures can be carried out in continuum by means of a single endoscope inserted into the body.

SUMMARY OF THE INVENTION

A first aspect of the present invention is a medical treatment endoscope which includes: a flexible sheath capable of a bending operation; a viewing unit for observing the vicinity of the tip relative to the sheath; an arm section protruding from the tip of the sheath and capable of a bending operation; an operation section for operating the arm section; and at least a transmission member, connected to the arm section and the operation section, for transmitting the operation of the operation section to the arm section. The transmission member is detachably connected to the operation section.

DETAILED DESCRIPTION OF THE INVENTION

Embodiments of the present embodiment will be described as follows. The basic structure of a medical treatment endoscope of the present invention is disclosed by the corresponding U.S. patent application Ser. Nos. 11/331,963, 11/435,183, and 11/652,880 of the present patent application. Disclosure by these applications is incorporated herein into the following explanation by reference.

First Embodiment

A medical treatment endoscope according to the present embodiment is functionally divided into an operation section for conducting necessary treatments by means of arm sections and procedure instruments; and an endoscope operation section for operating an endoscope. The present embodiment features operation sections that are operable in separate locations from the endoscope. An operation section built in an endoscope operation section necessitates an operator conducting all the operations alone, i.e., inevitably complex operations. The present embodiment enables two operators to share operations, i.e., operating an endoscope and conducting a treatment; thus, facilitating the operations.

Figure 1:
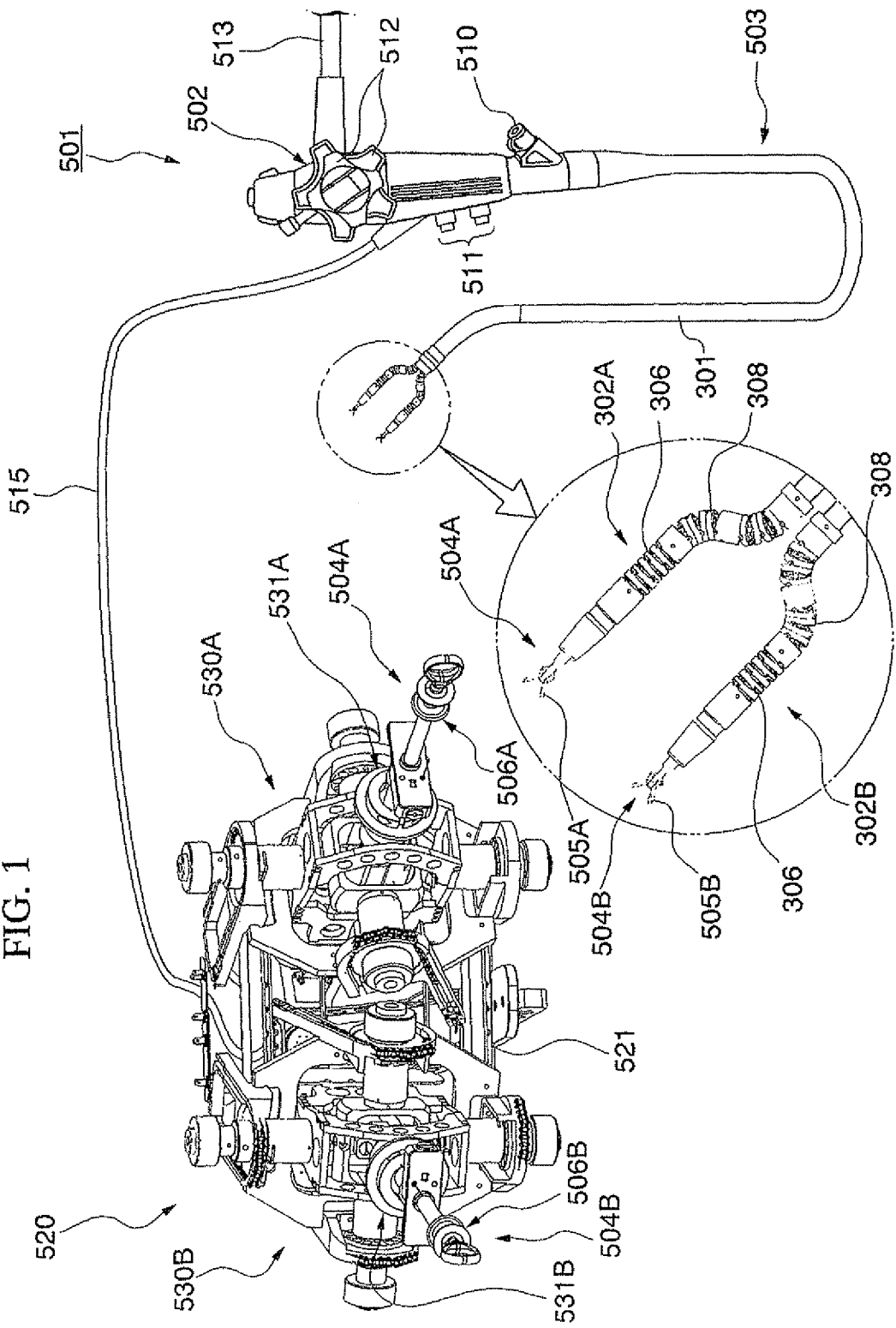
FIG. 1 is a perspective view showing a medical treatment endoscope according to a first embodiment.

As illustrated in FIG. 1, an endoscope insertion section 503 fully integrated with a medical treatment endoscope 501 extends from an end of an endoscope insertion section 502. An elongated and flexible endoscope insertion section 503 has the same structure as those of the U.S. patent application Ser. Nos. 11/435,183 and 11/652,880. That is, the endoscope insertion section 503 has a first sheath 301 having a first arm section 302A and a second arm section 302B on the tip of the first sheath 301. Treatment sections 505A and 505B of procedure instruments 504A and 504B each protrude from the tips of the arm sections 302A and 302B. A first bending part 306 and a second bending part 308, in this order from the tips of the arm sections 302A and 302B, are formed to each arm section 302A and 302B. Combined use with a third bending section 203B formed in the first sheath 301 enables a bending operation in a human body. The first and second arm members 302A and 302B may be inserted into another sheath protruding from the tip of the sheath 301 as disclosed by the U.S. patent application Ser. No. 11/652,880. Meanwhile, the operation section 520 is enlarged in FIG. 1 to help better understanding.

A forceps cap 510 is provided to a side of the endoscope insertion section 502 near an end that continues to the endoscope insertion section 503. The forceps cap 510 communicates to an operation channel formed in the first sheath 301. Inserting another procedure instrument, which is not shown in the drawing, from here enables the procedure instrument to protrude from the tip of the endoscope insertion section 503. In addition, disposed to the endoscope insertion section 502 are a switch 511, an angle knob 512, and a universal cable 513 that is connected to a control apparatus that is not shown in the drawing. For example, operating the switch 511 provides air-supply, water-supply, and suction through a channel formed in the first sheath 301. Operating the angle knob 512 bends the third bending section 203B into four directions with respect to an axial line.

In addition, an elongated flexible connection sheath 515 extends from the other end of the endoscope insertion section 502. An operation section 520 is disposed at an end of the connection sheath 515.

The operation section 520 has a base 521 that fixes the connection sheath 515. Attached to the base 521 are a first operation unit 530A and a second operation unit 530B. The first operation unit 530A has an operation stick 531A into which an operation section 506A of the procedure instrument 504A is inserted. The procedure instrument 504A is passed through the first arm member 302A. The operation section 506A is supported by the operation stick 531A so as to be capable of freely extending and retracting in the axial line and bending in four directions with respect to the axial line. The second operation unit 530B has an operation stick 531B into which an operation section 506B of the procedure instrument 504B is inserted. The procedure instrument 504B is passed through the second arm member 302B. The operation section 506B is supported by the operation stick 531B so as to be capable of freely extending and retracting in the axial line and bending in four directions with respect to the axial line. Furthermore, the operation section 520 fixed to an operation bed enables operation of the first second operation unit 530A and the second operation unit 530B.

Figure 2:
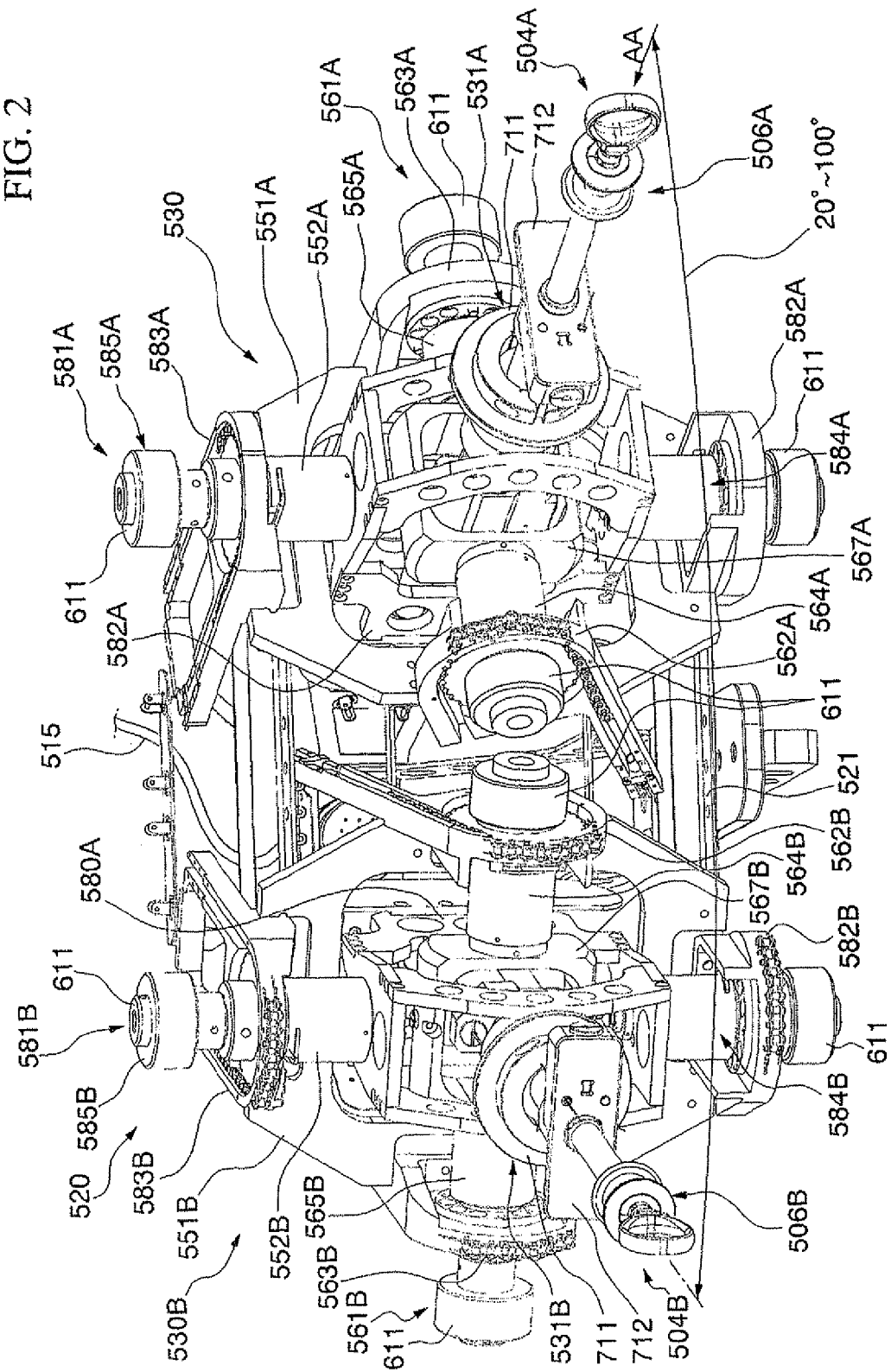
FIG. 2 is an enlarged view of an operation section.

As illustrated in FIG. 2 in an enlarged view, the operation units 530A and 530B are disposed diagonally so that portions closer to the connection sheath 515 are placed closer to each other. Two operation sections 506A and 506B (or two operation sticks 531A and 531B) are disposed at angles between 20° and 100°. Disposing the operation sections 506A and 506B with the opening angle relative to an operator facilitates the operator's operation, thus improving operability. In addition, the width of the operation section 520 closer to the connection sheath 515 can be reduced. Also, as disclosed by U.S. patent application Ser. No. 11/652,880, disposition (in horizontal direction) of arm sections 302A and 302B in an endoscope image obtained through an object lens of a viewing device (viewing unit) attached to the first sheath 301 can be coincided with the disposition (in horizontal direction) of the two operation units 530A and 530B. This improves correlation of an operator's perception and actual inner-body movement, thereby facilitating manipulation. Furthermore, less force is required for an operator to operate only the operation sticks 531A and 531B and the operation sections 506A and 506B of the procedure instruments 504A and 504B. Dispositions having reverse correlation with respect to horizontal or vertical direction provide similar operational perception obtained by laparoscopic instruments.

The configuration of the first operation unit 530A is explained.

Figure 3:
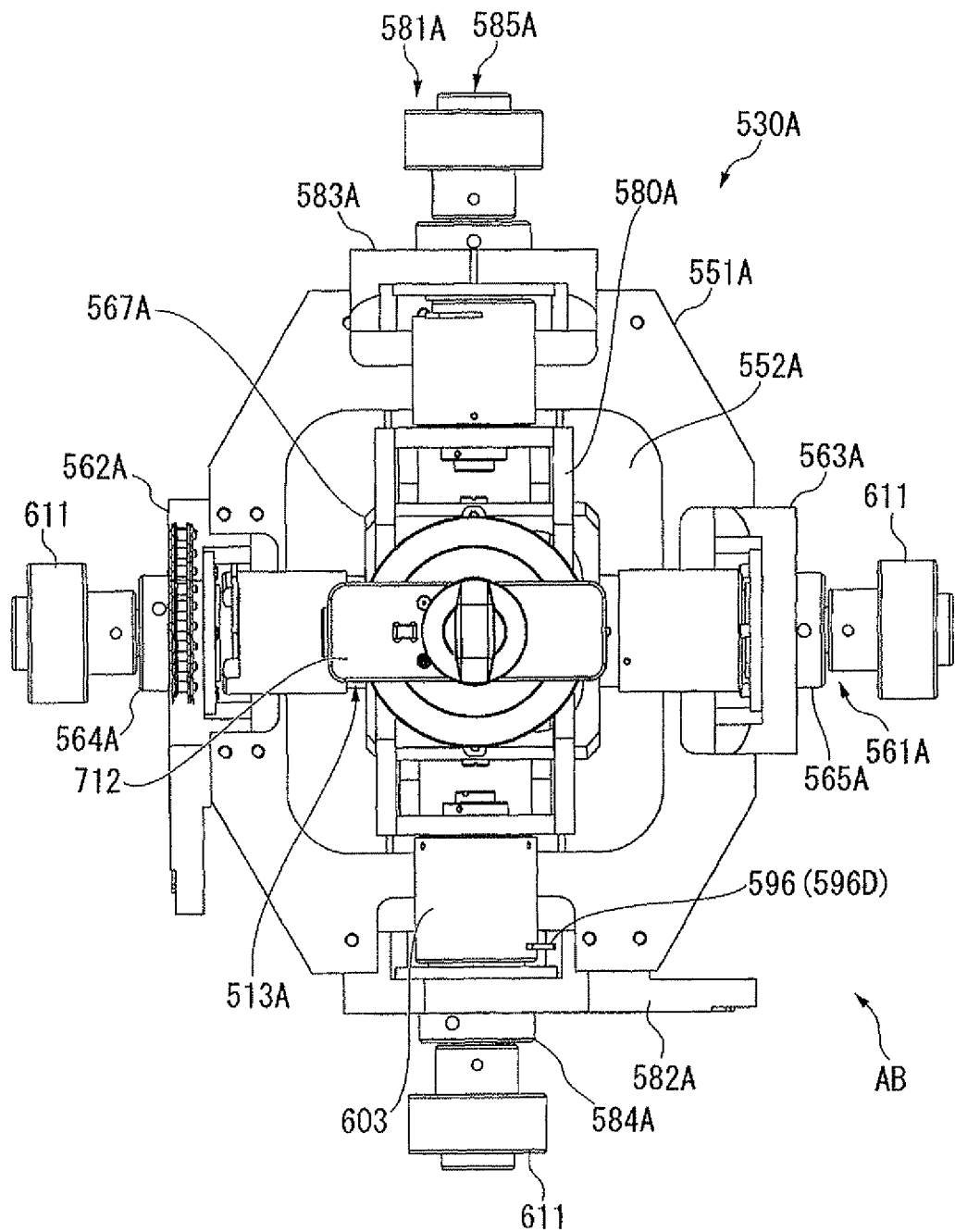
FIG. 3 is a view taken along the line A-A in FIG. 2 in parallel with an axial direction of a first operation section.
Figure 4:
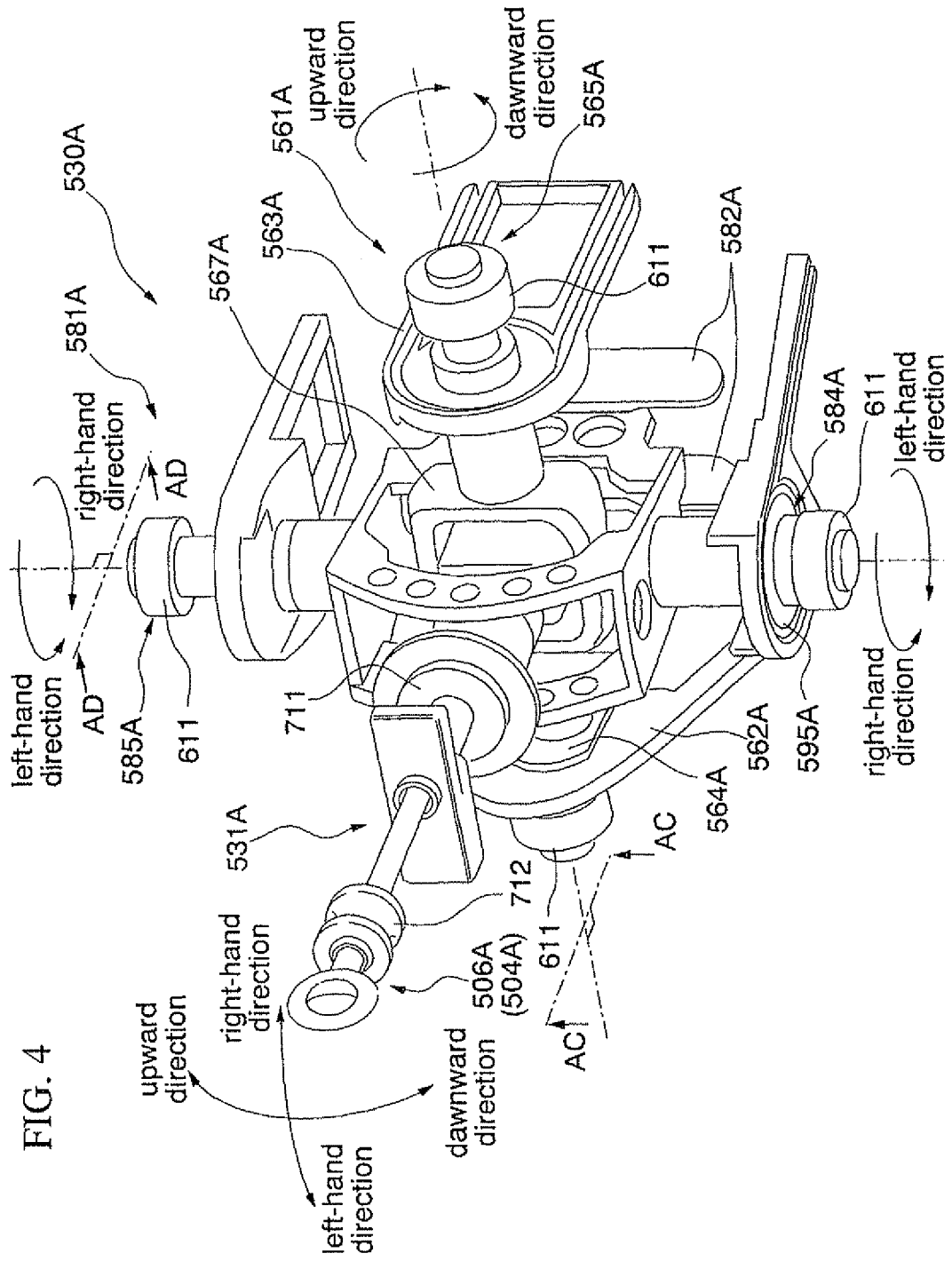
FIG. 4 is a view on arrow AB in FIG. 3.

As illustrated in FIGS. 2 to 4, the first operation unit 530A has a bracket 551A fixed to the base 521. The bracket 551A is fixed so that an opening 552A is substantially orthogonal to the center line of the first operation unit 530A. A first rotation mechanism 561A is attached to horizontal side surfaces of the bracket 551A. The first rotation mechanism 561A has a pair of support chips 562A and 563A that are fixed to place the opening 552A of the bracket 551A therebetween. A rotation shaft 564A is disposed to the support chip 562A. A rotation shaft 565A is disposed to the support chip 563A. The rotation shafts 564A and 565a are disposed coaxially. A frame 567A is supported by this pair of rotation shafts 564A and 565a so as to be freely capable of rotating with respect to the bracket 551. An opening of a rectangular frame 567A is disposed orthogonal to the center line of the first operation unit 530A. The operation stick 531A is inserted through the frame 567A. The operation stick 531A engaging with the frame 567A in rotating angles of the rotation shafts 564A and 565a is inserted so as to be independently capable of tilting in the axial lines of the rotation shafts 564A and 565A.

Figure 5:
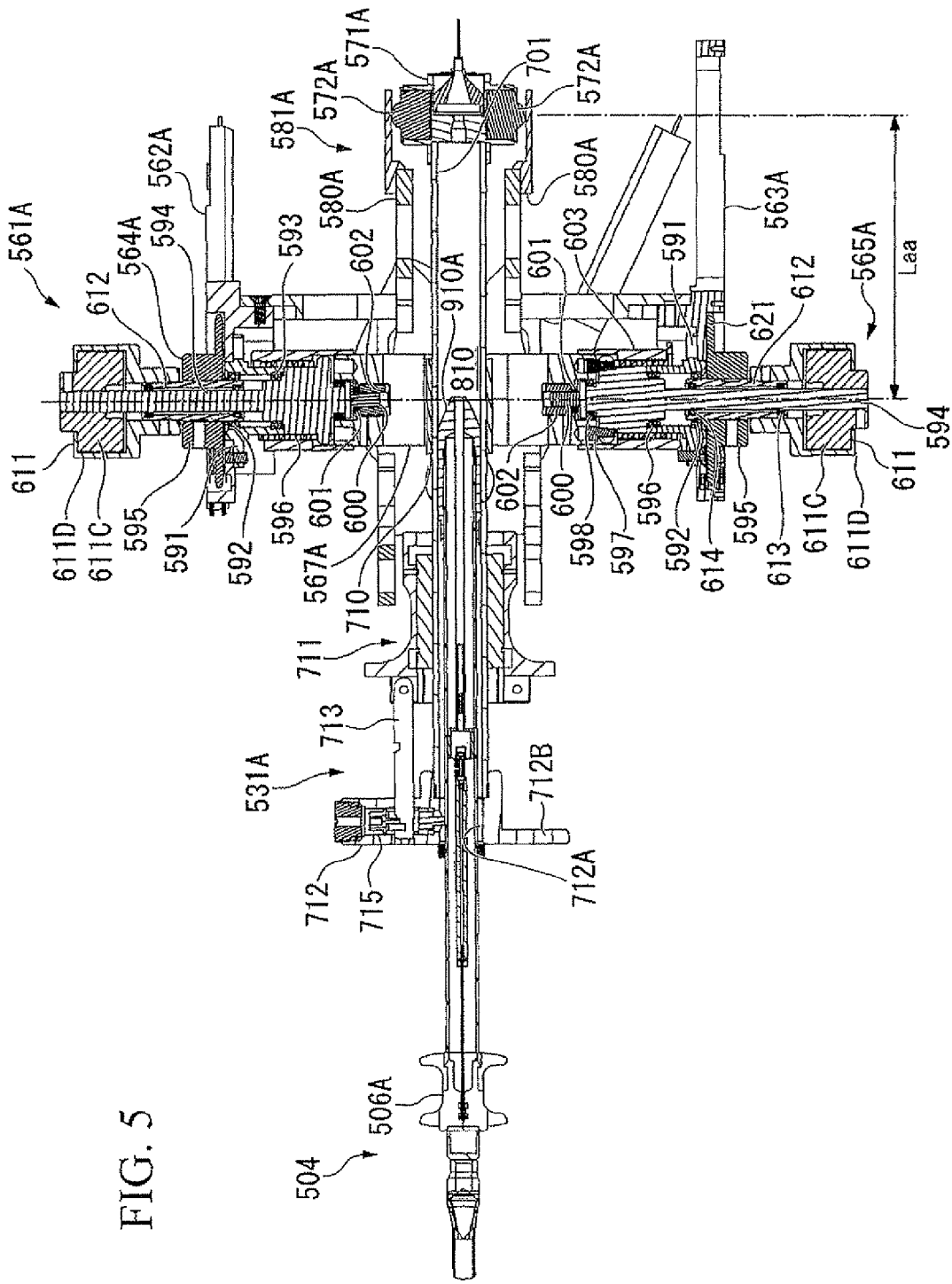
FIG. 5 is a cross-sectional view along the line AC-AC in FIG. 4.

As illustrated in FIG. 5, the tip section 571A of the operation stick 531A extends beyond the frame 567A. Ball rollers 572A are provided to the tip section 571A. The ball rollers 572A are disposed to place the center line of the operation stick 531A therebetween. The line passing through the centers of two ball rollers 572A is parallel with the axial lines of the rotation shafts 564A and 565A of the first rotation mechanism 561A as illustrated, i.e., where the operation stick 531A is not tilted. Distances Laa between the rotation shaft 564A and 565A and the ball rollers 572A are, for example, 50 to 200 mm.

Frames 580A of the second rotation mechanism 581A are further disposed so as to place the ball rollers 572A therebetween and slide on the ball rollers 572A. The frames 580A are supported rotatively by the pair of rotation shafts 584A and 585A. The pair of the rotation shafts 584A and 585A are disposed coaxially so that the axial lines are orthogonal to a pair of rotation shafts 564A and 565A and also orthogonal to the center line of the first operation unit 530A. The rotation shafts 584A and 585A are supported by support chips 582A and 583A each fixed on a vertical side surface of the bracket 551A.

The configuration of the rotation shafts 584A and 585A of the second rotation mechanism 581A will be explained here. Since the rotation shafts 584A and 585A have the same configuration, the rotation shaft 584A will be explained herein for reference.

Figure 6:
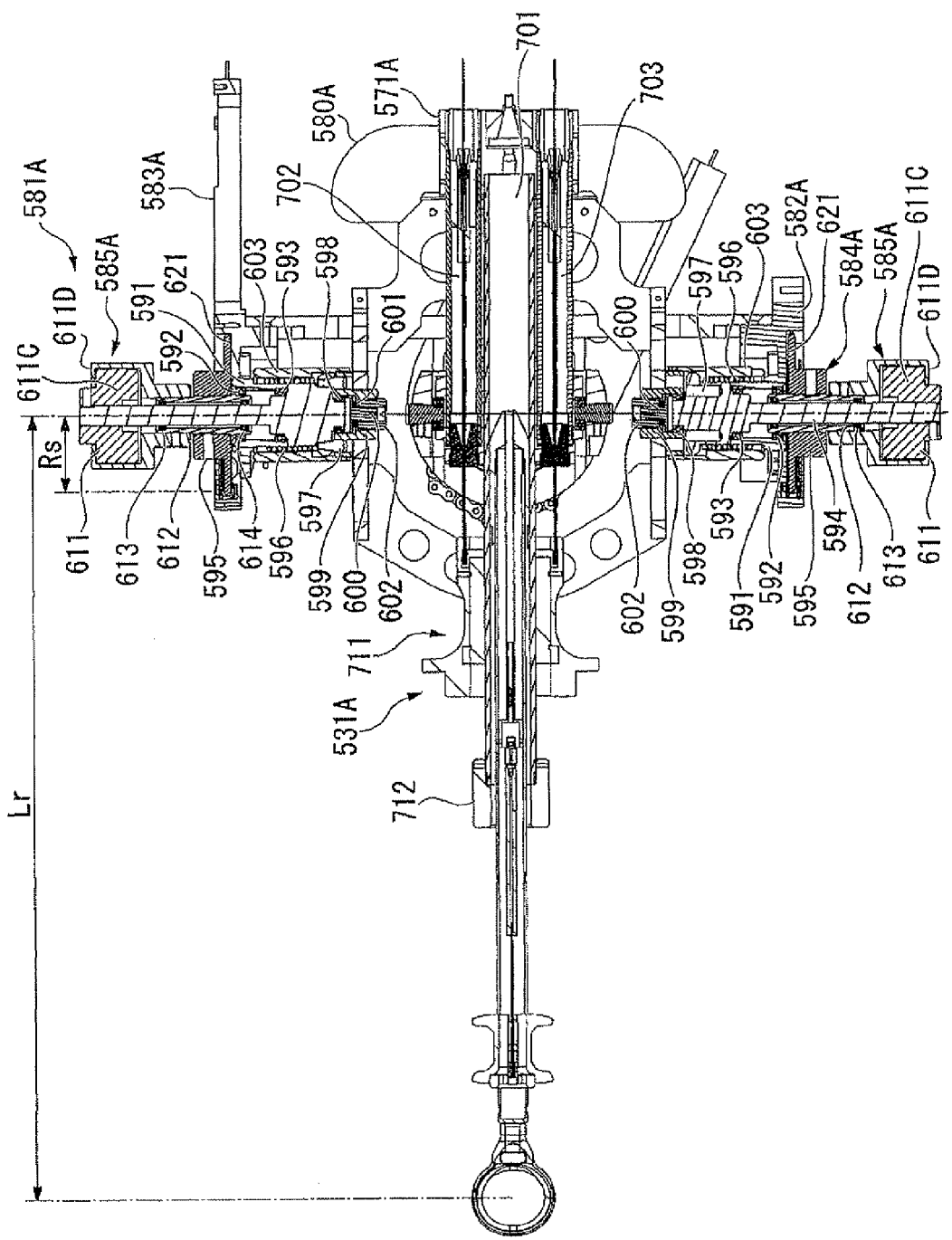
FIG. 6 is a cross-sectional view along the line AD-AD in FIG. 4.
Figure 7:
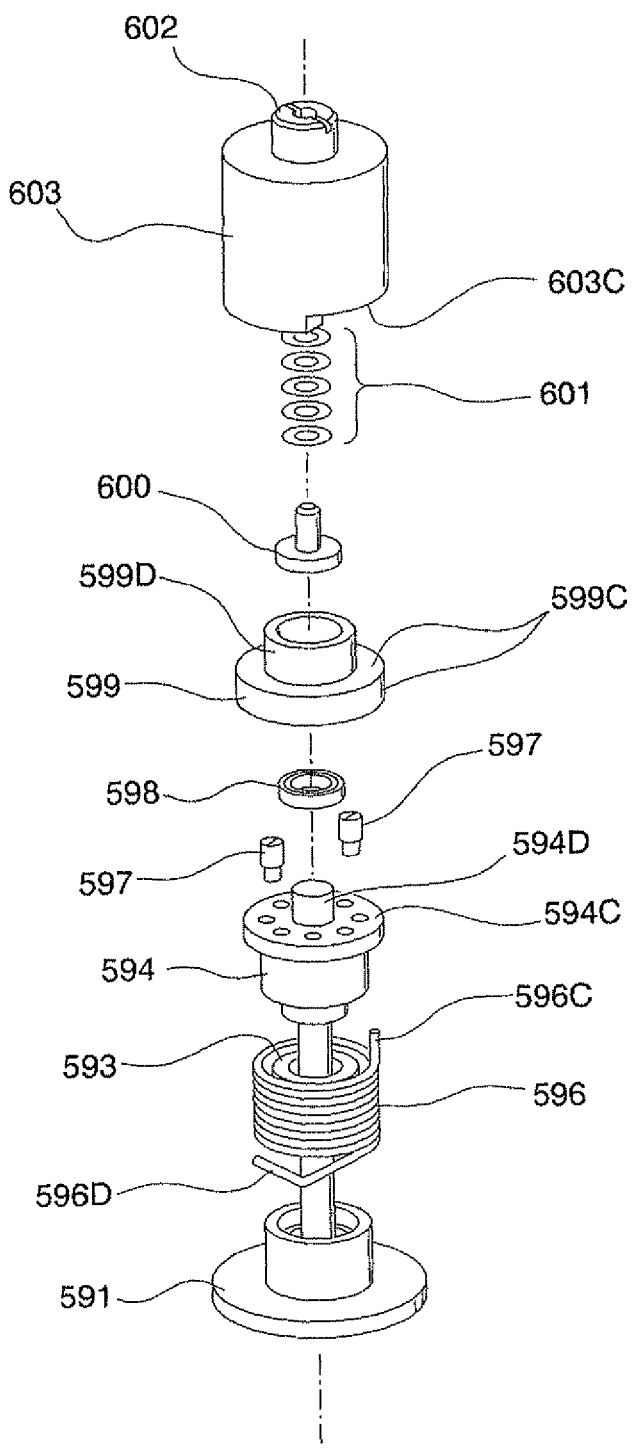
FIG. 7 is an exploded view for a rotational axis.

As illustrated in FIGS. 6 and 7, the rotation shaft 584A has a bearing 591 fixed to the support chip 582A. The bearing 591 has a flange at an end of the cylinder so that the bearing 591 is fixed to the support chip 582A by bolts passing through holes formed on the flange. Outer rings of the bearings 592 and 593 are press-fitted into the inside of the cylinder of the bearing 591 so as to be separate in the axial line. A drive shaft 594 is supported by the bearings 592 and 593 rotatively relative to the bearing 591. The reduced diameter portion of the drive shaft 594 passes through the bearing 591.

An end section of the drive shaft 594 is enlarged in diameter substantially to that of the bearing 591. A coil spring 596 is wound around between an outer periphery of the drive shaft 594 and an outer periphery of a cylindrical section of the bearing 591. Terminals 596C and 596D are bent on both sides of the coil spring 596. A terminal 596C is engaged with a groove formed on the flange 594C formed at an end of the drive shaft 594. An elemental wire of the coil spring 596 is rectangular in cross section. The rectangular shape may be a square or a rectangle.

The drive shaft 594 is formed by a protrusion 594D and a flange 594C. A plurality of screw holes are formed around the protrusion 594D. Each rotative pin 597 is screwed into each screw hole disposed by 180 degrees offset in a circumferential direction. An inner ring of the bearing 598 is press-fitted and fixed into the protrusion 594D. A bearing 599 is attached to an outer periphery of the bearing 598. The bearing 599 has a cylindrical section 599D having a flange. Inserted in advance into the cylindrical section 599D is a ring retainer 600 that depresses the ring retainer 600 toward a drive shaft 594 with a preload screw 602 via a diaphragm spring 601. A plurality of through-holes 599C are formed on the flange of the bearing 599 at equal intervals in a circumferential direction. The through-holes 599C are disposed corresponding to the disposition of the screw holes of the drive shaft 594. The diameter of the through-hole 599C is greater than that of a head portion of the rotative pin 597. That is, the through-hole 599C has freeplay.

Provided further to cover the flange 594C of the bearing 594 and the coil spring 576 is a cylindrical cover 603. A notch 603C is formed on a base portion of the cover 603. The other terminal 596D of the coil spring 596 is hooked at the notch 603C. In addition, a cylindrical section 599D of the bearing 599 protruding from the cover 603 is fixed to the frames 580A by a pin.

Since an initial state of the coil spring 596 tightens the outer peripheries of the drive shaft 594 and the bearing 591, the drive shaft 594 is joined to the bearing 591 by the coil spring 596. Since the bearing 591 is fixed to the support chip 582A, the drive shaft 594 cannot rotate in the direction for tightening the coil spring 596. However, it is rotatable in a direction for loosening the coil spring 596. In contrast, a tilting movement provided by an operator of the operation stick 531A into the direction for tightening the coil spring 596 tilts the frames 580A that makes contact with the operation stick 531A. Tilting the frames 580A rotates the bearing 594 of the rotation shaft 584A and the cover 603. Rotating the cover 603 loosens the coil spring 596, thereby releasing the drive shaft 594 locked to the bearing 591. This results in allowing the drive shaft 594 to rotate, thereby transferring the rotation to the sprocket 595. The present symmetric disposition of the rotation shaft 585A with respect to the operation stick 531A transfers the rotational movement of the operation stick 531A but not the rotational movement for tightening the coil spring 596 from the sprocket 595. The operator's operation is transferred but a reaction force by the sprocket 595 is maintained when the operator stops the operation. Thus, the position is maintained, and the operation can be facilitated.

The coil spring 596 for use in such a spring clutch must be made from a high-hardness material. Use of a high-gravity material, e.g., iron, may cause an increase in the weight of the operation section 520. Therefore, a high-hardness and low-gravity material, e.g., duralumin (#2000) or extra super duralumin (#7000), may be used.

Meanwhile, loosening the coil spring 596 to release the locked state and transferring the rotation via the coil spring 596 inevitably provide an excessive force acting on the coil spring 596. In order to avoid such a state, a play is provided so that the head portion of the rotative pin 597 of the drive shaft 594 makes contact with a periphery wall of the through-hole 599C of the bearing 594 after releasing the locked state. Rupture of the coil spring 596 is prevented by transferring the rotation by means of the rotative pin 597. The spring clutch having such a configuration, not limited to the present embodiment, can be used as a rotative structure for rotating the procedure instrument or the overtube.

In addition, the drive shaft 584 protruding from the flange of the bearing 591 is supported by bearings 613 and 614 so as to be rotative with respect to the hollow shaft 612. A sprocket 595 is fixed to a hollow shaft 611. It should be noted that a rotative member for pushing and drawing a wire, e.g., a wire pulley, may be used in place of the sprocket 595.

The hollow shaft 612 is rotatively supported by the bearing 592 with respect to the bearing 591. The drive shaft 594 and the hollow shaft 612 both protruding over the sprocket 595 are inserted in a torque limiter 611. The torque limiter 611 includes an outer 611C fixed to the hollow shaft 612 and an inner 61D fixed to the drive shaft 594. The inner 611D and the outer 611C unitarily rotate until a predetermined torque is applied. When excessive torque is applied, the outer 611C slides on the inner 611D; and thus, the rotation is not transferred.

Figure 8:
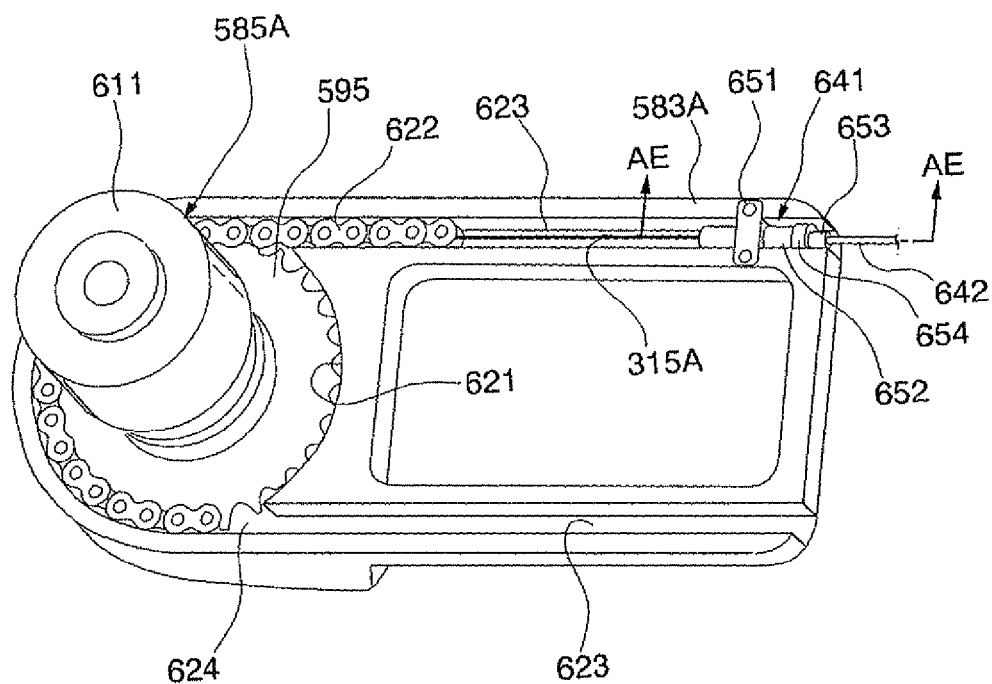
FIG. 8 is a perspective view for the other rotational axis, a support chip, and a bending wire.

As illustrated in FIG. 8 showing a configuration of the rotation shaft 585A, the sprocket 595 is rotatively housed in a circular recessing section 621 formed in the support chip 583A. A chain 622 is wound on teeth of the sprocket 595. A groove 623 is formed to the support chip 583A. An end part of the chain 622 can be drawn into the groove 623 that continues to the recessing section 621. The groove 623 is formed deeper than the recessing section 621. Providing a gap 624 between the groove 623 and the recessing section 621 prevents the chain 622 from being entangled between the sprocket 595 and the recessing section 621, thus guiding the chain 622 into the groove 623.

A first bending wire 315A is fixed to an end part of the chain 622. The first bending wire 315A bends the first bending parts 306 of the first arm members 302A illustrated in FIG. 1 in a right-hand direction.

Figure 9:
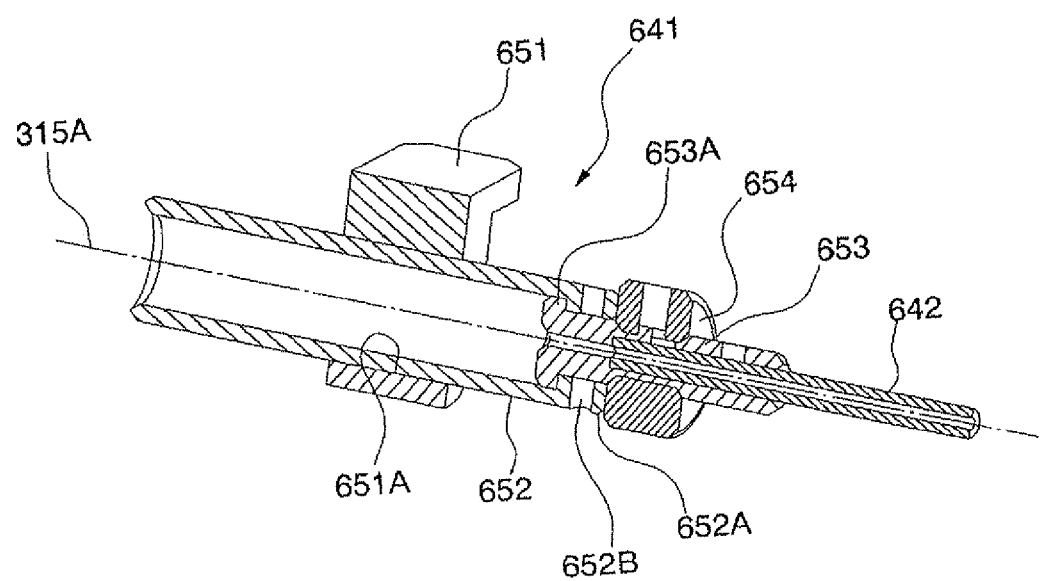
FIG. 9 is a cross-sectional view along the line AE-AE in FIG. 8.

As illustrated in FIG. 8, the first bending wire 315A is drawn into an adjuster 641 disposed at an end part of the groove 623 of the support chip 583A and introduced into a connection sheath 515 together with the coil sheath passing through the coil sheath 642 connected to the adjuster 641. The first bending wire 315A is finally reached to the first arm member 302A. As illustrated in FIGS. 8 and 9, the adjuster 641 has a coil base 651 fixed to the support chip 583A. A screw hole 651A is formed to the coil base 651. An adjustment shaft 652 having a thread on the outer periphery thereof is screwed into the screw hole 651A. The adjustment shaft 652 is a cylinder having a bottom. An end section 652A corresponds to the bottom part into which a coil stopper 653 is inserted. The removal of the coil stopper 653 is prevented by engaging a flange-shaped protrusion 653D with an inner surface of the end section 652A. Removal prevention in the reverse direction is provided by attaching a lock-screw 654 to the outer periphery. An end part of the coil sheath is fixed to the coil stopper 653. The first bending wire 315A passes through the adjustment shaft 652, followed by the coil stopper 653 and the coil sheath 642. The first bending wire 315A sometimes loosely extends during the step using the medical treatment endoscope 501. In this case, inserting a fixture into the hole 652B of the adjustment shaft 652 and rotating them cause the coil sheath 642 together with the adjustment shaft 652 to move in the axial direction. Forwarding the coil sheath 642 draws the first bending wire 315A from the coil sheath 642, thereby adjusting the loose state. Since the loose state can be adjusted by means of a screw, it is not necessary to dissemble the apparatus. Since the adjustment shaft 652 is rotatively engaged with the coil stopper 653, rotating the adjustment shaft 652 will never rotate the coil sheath 642.

Also, a sprocket 595 of the rotation shaft 584A is housed in the support chip 582A, and the chain 622 is wound around the sprocket 595. A first-bending wire which is not shown in the drawing is attached to the chain 622. The first bending wire 315A bends the first bending parts 306 of the first arm members 302A illustrated in FIG. 1 in a right-hand direction. An adjuster 641, also provided to the support chip 582A, can adjust the loose state by forwarding or drawing the coil sheath 642 having the first bending wire 315B therethrough. The first bending wire 315B inserted through the coil sheath 642 is introduced into the connection sheath 515 together with the coil sheath 642 and reached to the first arm member 302A.

As explained previously, the torque limiters 611 provided to the rotation shafts 584A and 585A prevent the rotation of the rotation shaft 585A from being transferred to the sprocket 595 when an excessive input is provided from the operation stick 531A. This results in preventing an excessive force from being applied to the first bending wire 315A. Considering a case assumed to use no torque limiter 611 may lead to a possibility where an excessive force is applied to the first bending wire 315A. The torque limiter 611 for controlling the maximum torque can prevent the first bending wire 315A from being fractured. In addition, disposing the torque limiter 611, the sprocket 595, and the rotation shafts 564A and 565A in this order from the outside shorten the distance between the support chips 582A and 583A, thereby downsizing the bracket 551A. This increases freedom in layout and contributes to a downsized and light-weight configuration.

The first rotation mechanism 561A will be explained next principally with reference to FIG. 5.

A rotation shaft 564A has a similar configuration to the rotation shaft 584A of the second rotation mechanism 581A except for the drive shaft 594 attachably engaged with the frame 567A via the rotative pin 597 in the rotative direction. Similarly, the other rotation shaft 565A has a similar configuration to the rotation shaft 585A of the second rotation mechanism 581A except for the drive shaft 594 attachably engaged with the frame 567A via the rotative pin 597 in the rotative direction.

Furthermore, a first bending wire 315D is joined to the sprocket 595 of one of the rotation shafts 564A via the chain 622. A first bending downward-operating wire 315D is joined to the sprocket 595 of one of the rotation shafts 564A via the chain 622. The first bending wire 315C and the bending wire 315D bend two first bending parts 306 of the first arm members 302A illustrated in FIG. 72 in vertical opening directions. The adjuster 641, also provided to the support chip 562A and 563A, can adjust the loose state by forwarding or drawing the coil sheath 642 having the first bending wires 315C and 315D therethrough.

Next, the operation stick 531A will be described.

Figure 10:
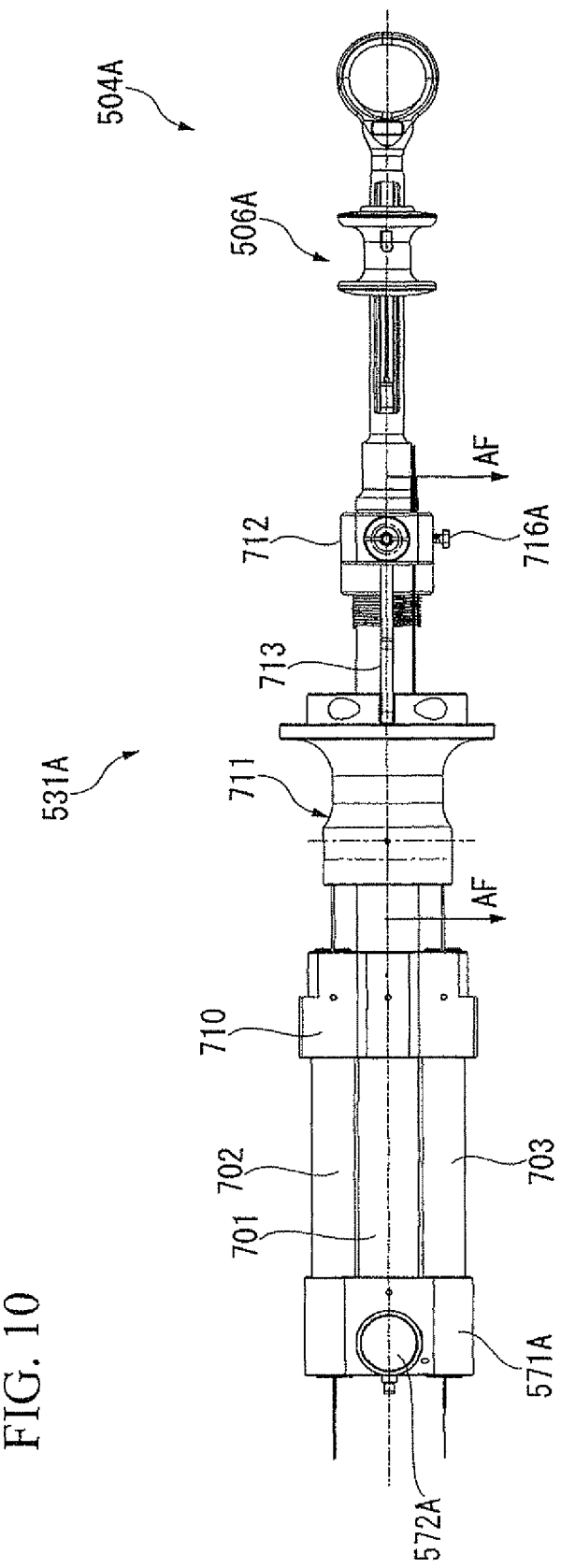
FIG. 10 is a plan view illustrating a first operation stick and a procedure instrument.

In the operation stick 531A as illustrated in FIGS. 5, 6, and 10, three cylindrical shafts 701, 702, and 703 bundled together are fixed to a tip portion to which a ball roller 572A is attached. The central shaft 701 is longer than two shafts, i.e., shafts 702 and 703. The other two shafts 702 and 703 barely reach to an abutment section 710 that serves as a rotative fulcrum making contact with the frame 567A of the first rotation mechanism 561A. In contrast, the central shaft 701 extends beyond the abutment section 710.

A second bending slider 711 capable of freely forwarding or retracting in the axial direction is attached to the central shaft 701. Furthermore, a ratchet base 712 is fixed to a base end of the shaft 701. In the initial state, the second bending slider 711 cannot be extended or retracted because the second bending slider 711 is joined to the ratchet base 712 by a connection plate 713 connected to the second bending slider 711.

Figure 11:
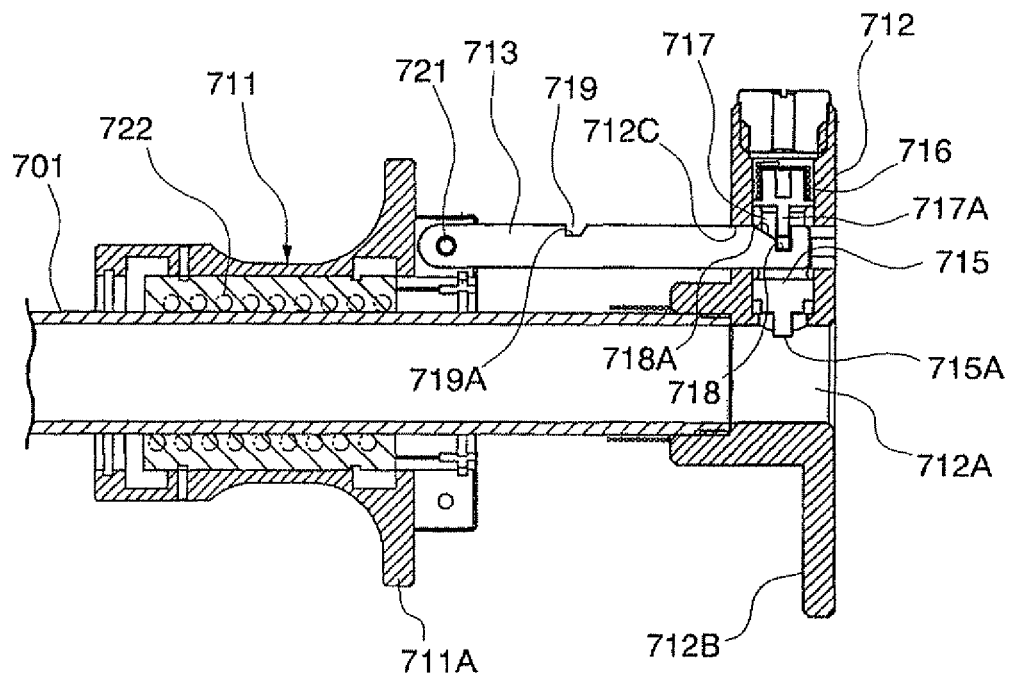
FIG. 11 is a cross-sectional view along the line AF-AF in FIG. 10 illustrating a pre-insertion state of the procedure instrument.
Figure 12:
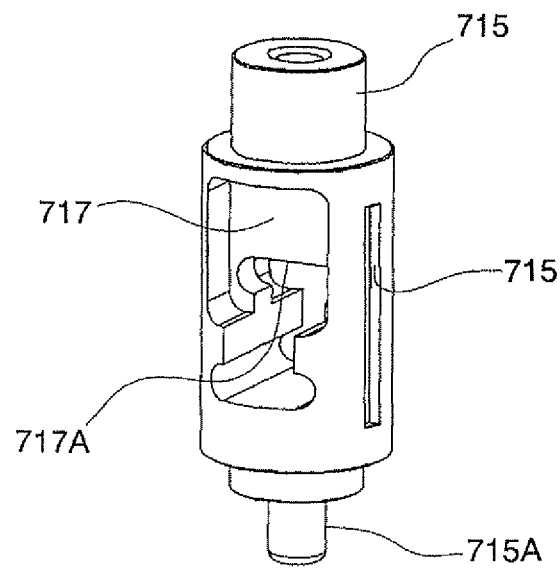
FIG. 12 is a perspective view for a piston.

As illustrated in FIG. 11, a through-hole 712A is formed in the center of the ratchet base 712. The through-hole 712A serves as an entrance from which the operation section 506A of the procedure instrument 504A is inserted. Furthermore, a part 712B of an outer periphery of the ratchet base 712 extends in a direction orthogonal to the axial line direction. Putting a thumb here allows the second bending slider 711 to be smoothly forwarded or retracted. A piston 715 slidable in a radial direction is housed in the ratchet base 712. The piston 715 is urged by a coil spring 716 in a radial direction orthogonal to the axial line direction. The protrusion 715A at the tip protrudes into a through-hole 712A that is an insertion path for the procedure instrument 504A. A slit 717 is formed on the piston 715. An engagement chip 717A is formed in the slit 717. A first groove 718 of the connection plate 713 is engaged with the engagement chip 717A. The first groove 718 is inserted through the slit 712C penetrating the ratchet base 712. Meanwhile, a vertical groove 717C that is parallel in a radial direction may be formed on the piston 715 as illustrated in FIG. 12. Inserting the tip portion of a clamping-bolt 716A (see FIG. 10) into the vertical groove 717C of an outer periphery of the ratchet base 712 can prevent the rotation of the piston 715. This prevents the piston 715 from galling the connection plate 713, thereby providing smooth movements of the piston 715 and the connection plate 713 as explained later.

Figure 23:
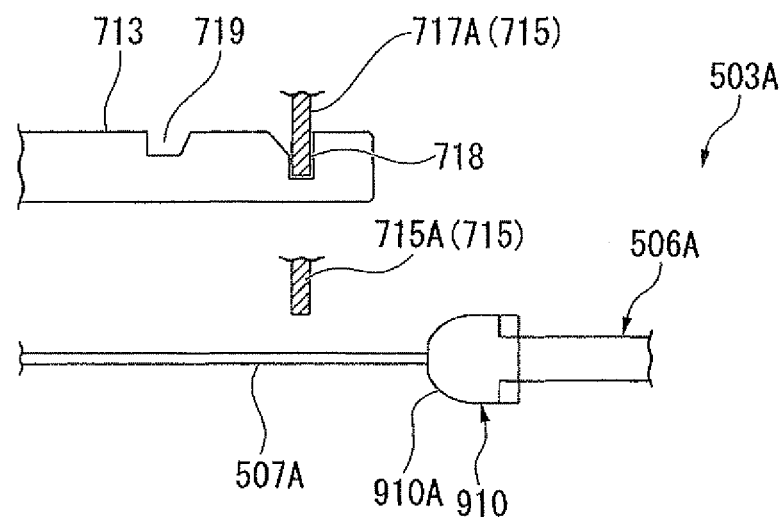
FIG. 23 illustrates motions provided by a cam, a piston, and a connection plate when the procedure instrument is inserted into the first operation stick.
Figure 25:
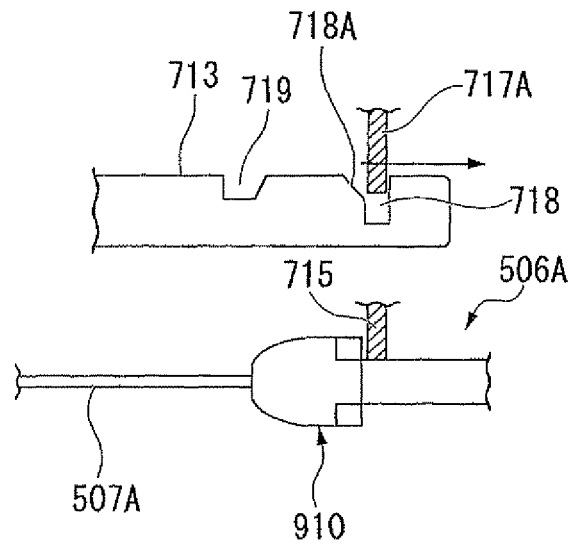
FIG. 25 illustrates of the connection plate in a retractable state.
Figure 27:
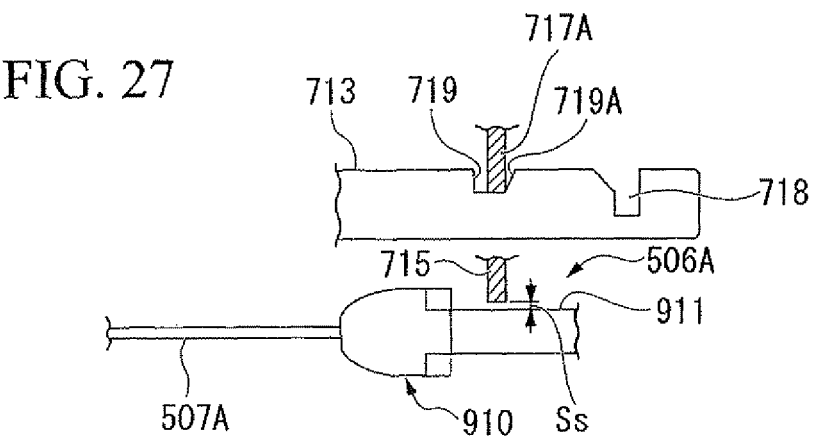
FIG. 27 illustrates an engaged state of the cam to a second groove.
Figure 28:
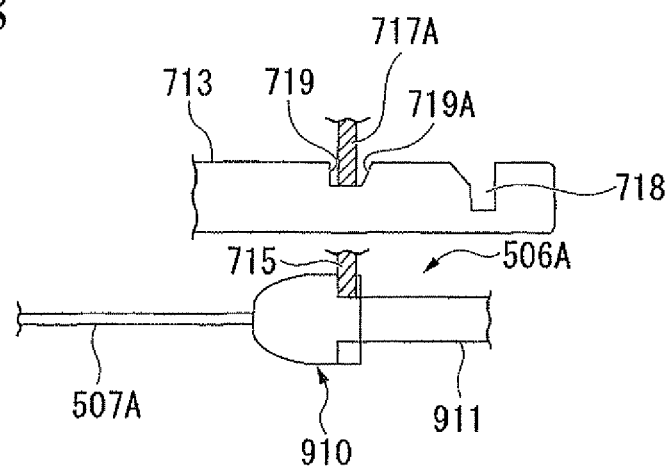
FIG. 28 illustrates the cam pushing up the piston when removing the procedure instrument.
Figure 29:
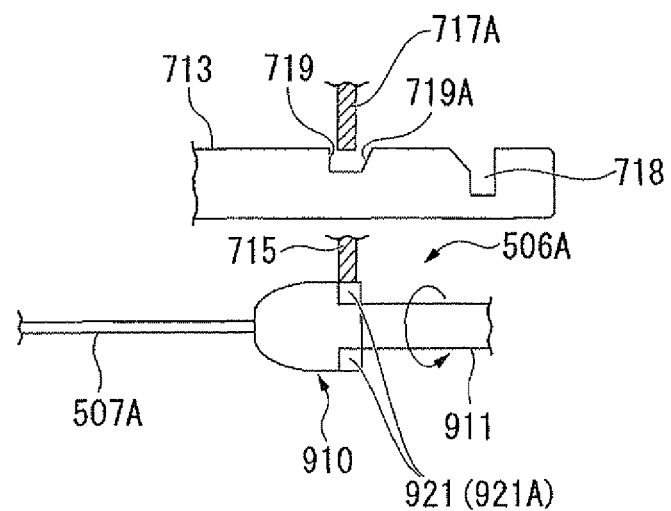
FIG. 29 illustrates the piston pushed up by rotating the cam.

The tip of the connection plate 713 is joined to the second bending slider 711 by a fulcrum pin 721 and extends substantially parallel in the axial line from here toward the ratchet base 712. The recessing shape of the first groove 718 allows the engagement chip 717A of the piston 715 to enter there, and a midpoint of the wall surface of the tip portion of the first groove 718 forms an inclination surface 718A. The inclination surface 718A gradually widens the first groove 718 from the midpoint to the tip portion. A second groove 719 is formed at a further tip portion than the first groove 718 is formed. The recessing shape of the second groove 719 allows the engagement chip 717A of the piston 715 to enter there. The second groove 719 is deeper than the first groove 718. The base end wall surface of the second groove 719 forms an inclination surface 719A. The inclination surface 719A gradually widens the second groove 719 toward the tip portion. The first groove 718 is positioned so that the second bending part 308 of the first arm member 302A as illustrated in FIG. 1 becomes straightened. The second groove 719 is positioned so that the second bending parts 308 bend to open the first arm member 302A. This allows the arm section 302A to close by engaging the first groove 718 with the piston 715, and allows the second arm member 303A to open by engaging the second groove 719 with the piston 715. As previously described, the engagement of the piston 715 with the grooves 718 and 719 can be released with a small force since the inclination surfaces 718A and 719A are formed in the grooves 718 and 719. This facilitates smooth switching of the engagement position of the piston 715 with the grooves 718 and 719. As illustrated in FIG. 23, the spring 791 forces the second bending slider 711 and the connection plate 713 to be positioned toward the tip portion by the spring force when the procedure instrument 504A is not inserted and thus, the first groove 718 engages with the piston 715. As illustrated in FIG. 25, the piston 715 is pushed by the operation section 506A of the procedure instrument 504A when the procedure instrument 504A is inserted. Since this state of the engagement chip 717A can move up the inclination surface 718A, the second bending slider 711 can be drawn, and the second bending part 308 can be opened. In this configuration, the procedure instrument 504A must be inserted to draw the second bending slider 711 because the tip of the procedure instrument 504A can hardly be passed through the opening state of the second bending part 308. As illustrated in FIG. 27, the engagement chip 717A makes contact with the inclination surface 719A as long as the second bending slider 711 is drawn toward the base end. The tension applied by the second bending wires 316A and 316B urges the slider 711 toward the tip. As illustrated in FIGS. 28 and 29, raising the piston 715 necessitates a significant force if the disposition angle of the inclination surface 719A is significantly equal to 90°. If the disposition angle is substantially horizontal, the piston 715 is spontaneously raised by the tension applied by the second bending wires 316A and 316B and therefore, the second bending slider 711 moves toward the tip, and the second bending part 308 closes. The suitable angle $\alpha$ of the inclination surface 719 is $60° \leq \alpha \leq 90°$.

The second bending slider 711 is disposed coaxially with the axial line of the operation stick 531A. Therefore, the compact first operation unit 530A can be obtained. Formed at the base end thereof is an edge section 711A for putting a thumb. A linear stroke 722 is built in a portion making contact with the shaft 701 to provide smooth sliding movement on the shaft 701.

Figure 13:
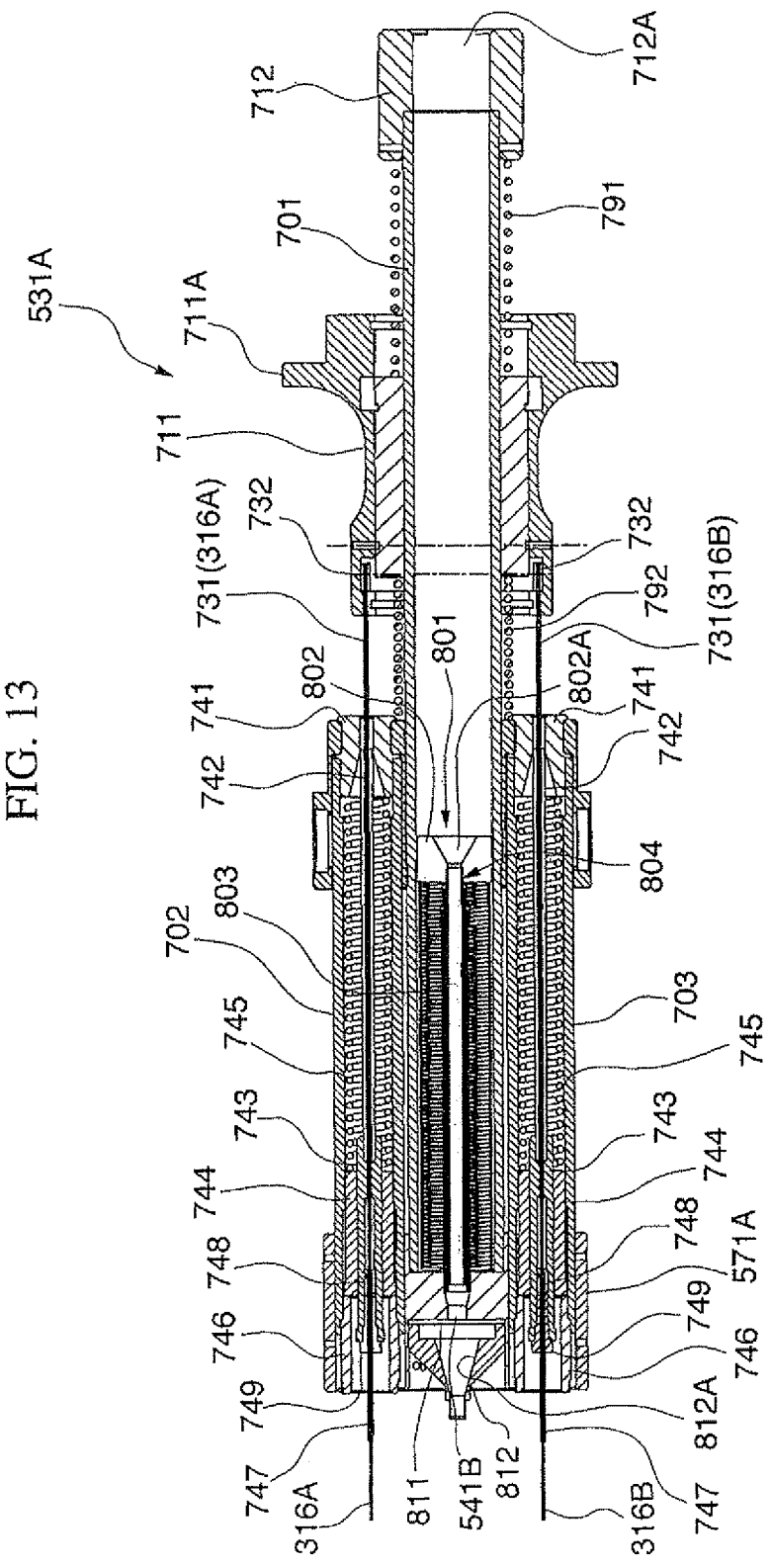
FIG. 13 is a cross-sectional view showing an enlarged state of a first operation stick illustrated in FIG. 6.

As illustrated in FIG. 13, two pipes 731 are attached to the tip of the second bending slider 711 so as to place the axial line between the pipes 731. Second bending wires 316A and 316B are passed respectively through these pipes 731. The second bending wires 316A and 316B are fixed in the second bending slider 711 so that the second bending wires 316A and 316B cannot be removed from the second bending slider 711. Disposing the second bending wires 316A and 316B symmetrically with respect to the second bending slider 711 equalizes the force applied to the second bending slider 711 and thus providing smooth movement thereof.

Two shafts 702 and 703, disposed further toward the tip, each have the pipe 731 inserted therethrough. The pipe 731 and the second bending wires 316A and 316B are inserted through the shafts 702 and 703 disposed side by side. The shafts 702 and 703 each have a retainer member 741 at the base end. Another pipe 742 is inserted from the tip through the retainer member 741. A pipe 731 and a second bending-wires 316A and 316B are passed through the pipe 742. The tip of the pipe 742 is supported by a coil-receiving casing 743. The coil-receiving casing 743 is screwed in the hole of the cylindrical pusher 744 and fixed there. An end portion of the coil spring 745 makes contact with the base end of the pusher 744. The other end portion of the coil spring 745 is butted against the retainer member 741. The pusher 744 is urged by the coil spring 745 toward the tip. In response to excessive force that draws the second bending wires 316A and 316B, a force that relatively moves the coil sheath 747 to an operator's hand is applied and thus, the coil spring 745 is compressed via the pusher 744. The coil spring 745 that is preset to a length exerting a predetermined force begins to contract if the preset force is overreached. Since the second bending wires 316A and 316B can further be drawn in accordance with the contraction of the coil spring 745, an excessive force is not applied to the second bending wires 316A and 316B. A force applied to the second bending wires 316A and 316B will never increase rapidly as long as the coil spring 745 can be contracted if an excessive force is applied and therefore, the second bending wires 316A and 316B will never be cut since overload mass is curbed. Meanwhile, the coil spring 745 is compressed by a pusher retainer 746 screwed from the tips of the shafts 702 and 703. Since the initial position of the pusher 744 can be adjusted in accordance with the compression mass of the pusher retainer 746, differences in rigidity and bending force based on the coil springs 745 can be adjusted.

Furthermore, only the second bending wires 316A and 316B are extracted from the pipe 742. The second bending wires 316A and 316B are inserted through the pusher retainer 746 in the coil-receiving casing 743 and introduced through the connection sheath 515 together with the coil sheath 747 to reach to the second bending part 308. The base end of the coil sheath 747 is brazed to a tubular coil receiver 748 and fixed there in the coil-receiving casing 743. A coil-receiver-retainer 749 is screwed from the tip through the coil-receiving casing 743. The coil-receiver-retainer 749 rotatively locking the coil receiver 748 prevents the coil sheath 747 from being removed from the coil-receiving casing 743, thereby preventing the pusher retainer 746 from being twisted. The lengths of the second bending wires 316A and 316B corresponding to the coil sheath 747 may sometimes have assembly error, and such error may sometimes be caused by the stretching of the second bending wires 316A and 316B. Adjusting the screwing amount of the coil-receiving casing 743 relative to the pusher 744 can adjust the error.

Figure 14:
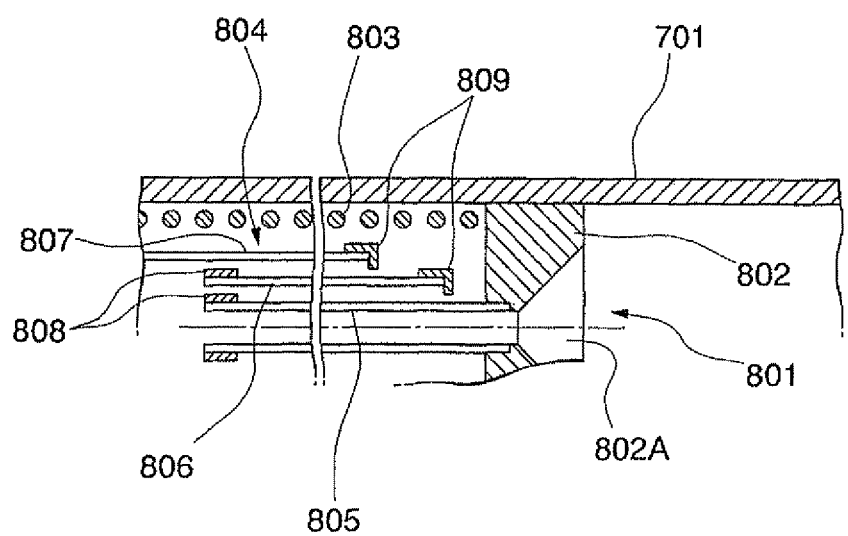
FIG. 14 shows a channel in magnified view.

As illustrated in FIGS. 13 and 14, a channel 801 for passing a procedure instrument 504A therethrough is built in the central shaft 701. The channel 801 has, in order from the base end, a retainer 802 that accommodates the procedure instrument 504A, a coil spring 803 inserted between the retainer 802 and the tip section 571A, and an extendable pipe 804 disposed in the coil spring 803. A hole 802A is formed in the center of the retainer 802. The hole 802A serves as an entrance for inserting the procedure instrument 504A therefrom. The hole 802A is a tapered hole where the opening diameter increases toward the base end. The hole 802A having a funnel shape facilitates the insertion of a distal end of the insertion section 507A of the procedure instrument 504A. The extendable pipe 804 has three pipes 805, 806, and 807 each of which are different in diameter. These pipes are disposed coaxially. A removal stop 808 is attached to the pipes 805 and 806. A stopper 809 locked to the removal stop 808 is attached to each pipe 806 and 807. That is, the extendable pipe 804 becomes the shortest when three pipes 805, 806, and 807 substantially overlap. Extending each pipe 805, 806, and 807 until engaging the locking stopper 809 with the removal stop 808 allows the extendable pipe 804 to be the longest. While the drawings illustrate the compressed state of the coil spring 803, it restores under the no-load condition. The retainer 802 moves to the vicinity of a shaft 701 and to the vicinity of the distal end of the piston 715. Since the retainer 802 is disposed at the base end of the shaft 701 unless the procedure instrument 504A is not inserted, the insertion section 507A of the procedure instrument 504A can be inserted easily. The retainer 802 is pushed by the tip portion of the operation section 506A of the procedure instrument 504A to be forwarded to the position illustrated in FIG. 13 when the procedure instrument 504A is inserted. It should be noted that the extendable pipe 807 is not limited to a triple-pipe structure.

A space for passing the procedure instrument 504A therethrough is provided in a tip section 571A that joins three shafts 701, 702, and 703. An airtight valve 811 is provided on a path into which the procedure instrument 504A is inserted and thus, the airtight condition inside of the body subjected to a medical operation can be maintained even if the procedure instrument 504A is removed during the medical operation. The airtight valve 811 is made of, for example, a rubber sheet disposed to seal a hole 571B that communicates with the shaft 701. Formed to the rubber sheet is a notch into which an insertion portion of the procedure instrument 504A can be inserted. Passing the procedure instrument 504A therethrough necessitates opening the notch. Removing the procedure instrument 504A closes the notch, thereby maintaining the airtight condition. A retainer 812 is used to fix the airtight valve 811. Fixing the retainer 812 onto the tip section 571A by screws facilitates exchanging the airtight valve 811 made of a rubber sheet. Meanwhile, the procedure instrument 504A is introduced into the body through a hole 812A formed in the retainer 812. Forming the hole 812A so as to be tapered toward the tip facilitates the insertion of the procedure instrument 504A.

The configuration of the second operation unit 530B is explained.

The second operation unit 530B has a symmetric configuration to the first operation unit 530A with respect to the horizontal center line of the operation section 520. A symbol "B" is added to some components included in the operation unit 530B to distinguish them from those of the first operation unit 530A.

A procedure instrument 504A inserted through the operation section 520 will be explained next. Although only the procedure instrument 504A will be explained here, it should be noted that the procedure instrument 504B has the same configuration. An end of each procedure instrument 504A and 504B may be a high-frequency knife, a puncture needle, a snare, a clip, or additional forceps.

Figure 15:
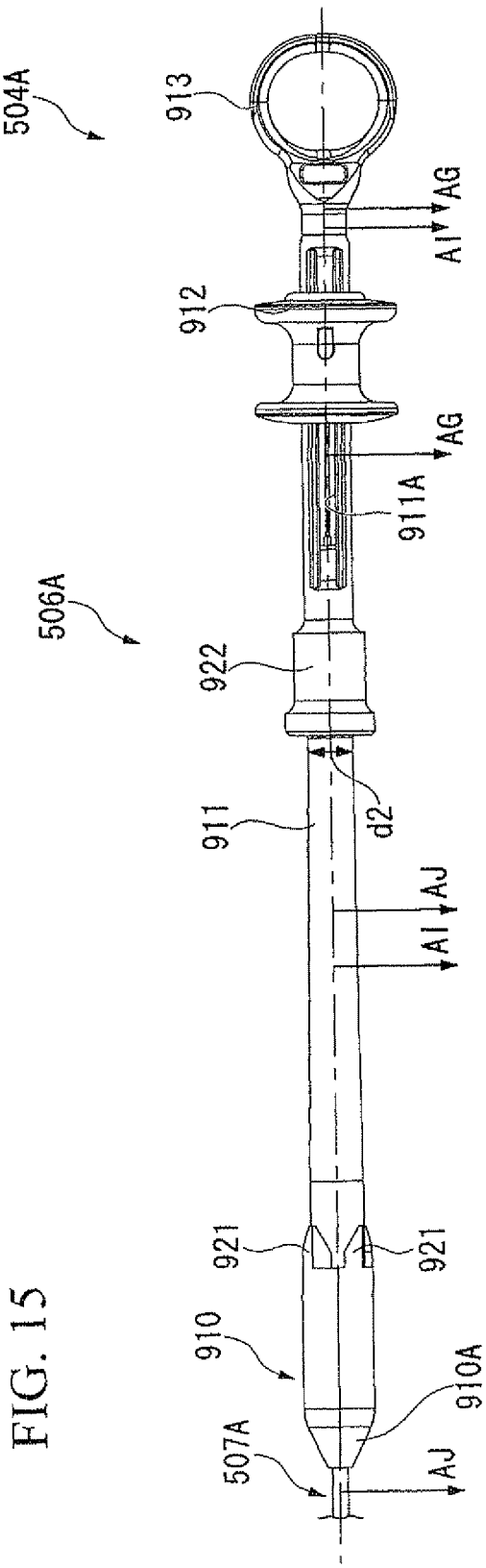
FIG. 15 is a plan view illustrating a procedure instrument.

As illustrated in FIG. 15, a treatment section 505A (see FIG. 1) and an operation section 506A both provided to the tip of the procedure instrument 504A are joined by an elongated flexible insertion section 507A. The operation section 506A has a main body section 911 having a cam 910 at the tip thereof. A slider 912 that drives the treatment section 505A is attached at the base end of the main body section 911 rotatively in the axial line direction. In addition, a finger-hook ring 913 is attached to the base end of the main body section 911.

Figure 16:
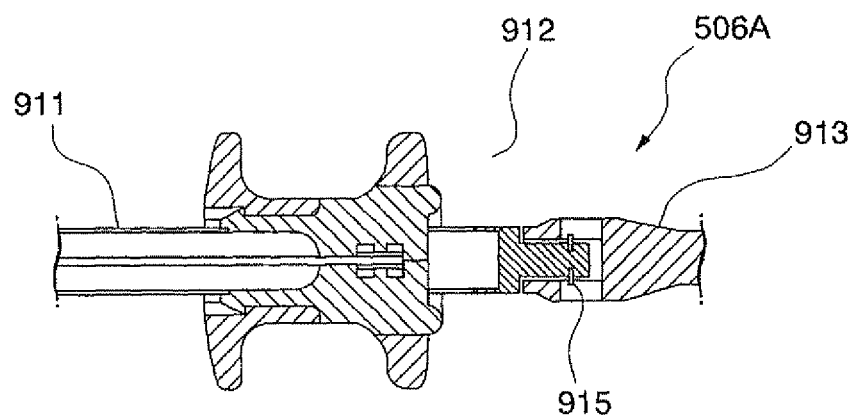
FIG. 16 is a cross-sectional view along the line AG-AG in FIG. 15.
Figure 17:
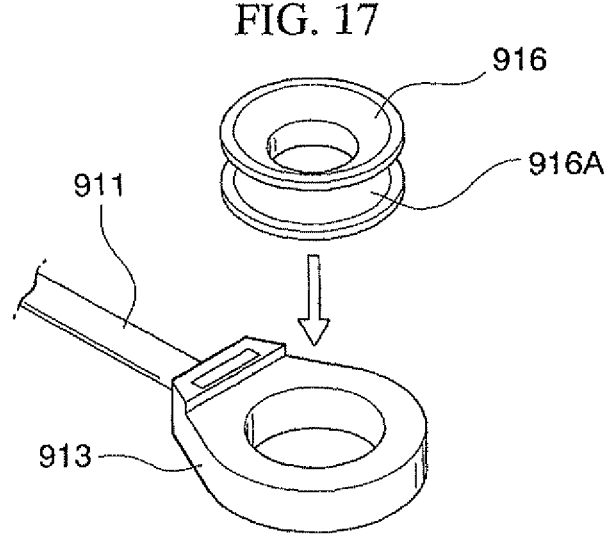
FIG. 17 describes how to attach a protection member to a ring.
Figure 18:
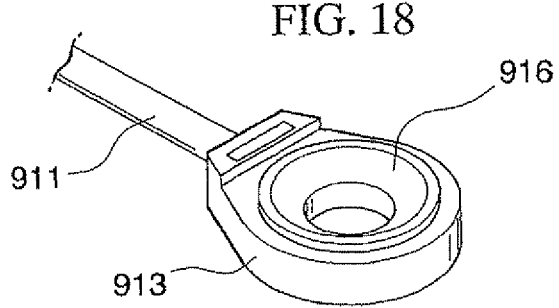
FIG. 18 describes a post-attached protection member disposed to the ring.

As illustrated in FIG. 16, a ring 913 is joined to the main body section 911 via an E ring 915. Operability is desirable since the ring 913 can be rotated by the E ring 915 around the axial line. It should be noted that a rubber-made protection member 916 may be used to be fitted to the inside of the ring 913 as illustrated in FIGS. 88 and 89. A groove 916A detachable from the ring 913 is formed on an outer periphery of the protection member 916. The use of rubber eases pain on fingers during operation. In addition, a detachable configuration is superior in maintaining cleanliness and sterilization. Making the protection member 916 of, for example, a silicone rubber, imparts chemical resistance and sterilization.

Figure 19A:
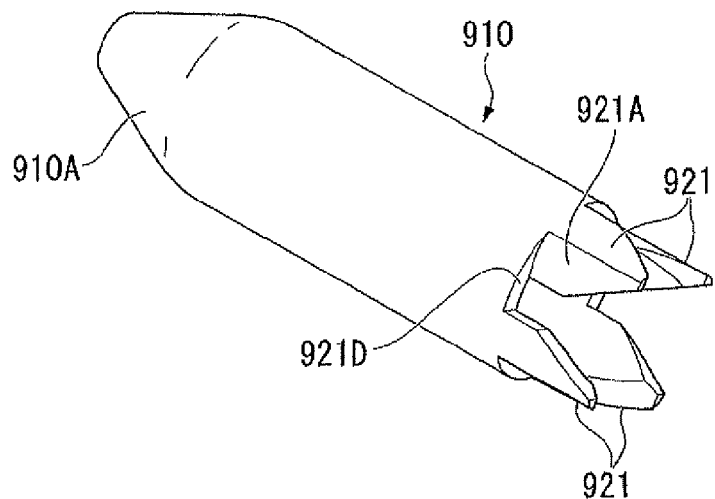
FIGS. 19A and 19B illustrate a cam in a perspective view.

As illustrated in FIGS. 5 and 15, the tip portion of the cam 910 is a taper where an opening diameter decreases. When the taper surface 910A is inserted through the operation stick 531A, the taper surface 910A serves for pushing up the piston 715 and pressing the channel 801. The outer diameter of the cam 910 is substantially the same as the inner diameter of the shaft 701 so that the cam 910 is slidable on the shaft 701. Four blade sections 921 extending in the axial line direction are provided to the base end of the cam 910. As illustrated in FIG. 19A, each blade section 921 is provided only on the outer periphery of the cam 910. A side surface 921A in the circumferential direction forms a tilted and curved surface from the center toward radially outward.

Figure 19B:
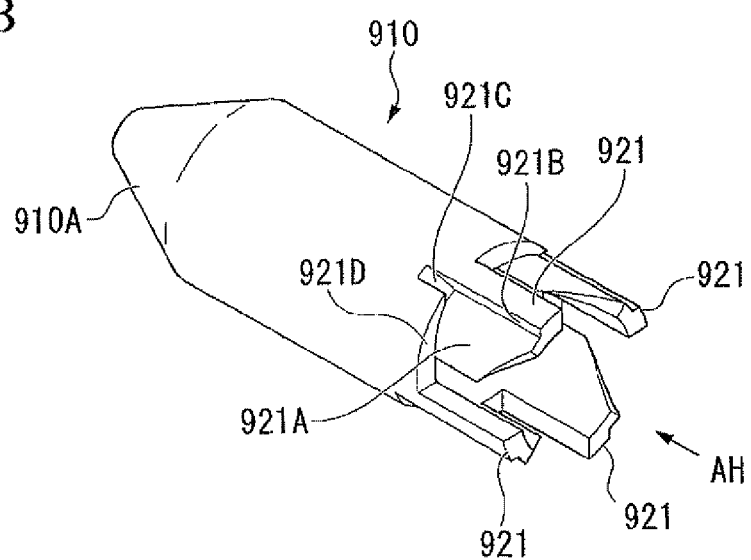
Figure 20:
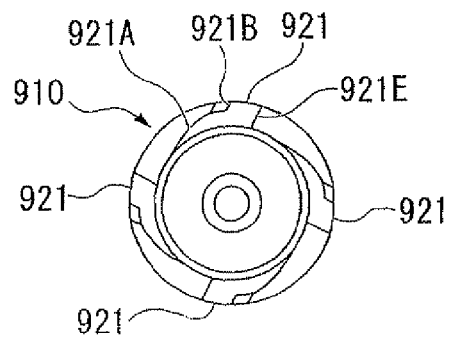
FIG. 20 is a view on arrow AH in FIG. 19.

In addition, as illustrated in FIGS. 19B and 20, a slope 921C directed to the tip together with a gap surface 921B standing in a radial direction may be formed on the outer periphery of the tilted side surface 921A of the cam 910. A gap 921D between the tilted side surface 921A and the outer periphery of the cam 910 is smoothly resolved by the slope 921C. A side surface 921L disposed opposite to the side surface 921A in the blade section 921 has a space greater than the diameter of the piston 715 between the side surface 921A of another blade section 921 adjacent in the circumferential direction and the side surface 921E. The side surface 921L is tilted in the direction the same as the tilting direction of the side surface 921A. The tilting direction of the side surface 921E is significant, i.e., forms a steep surface.

A main body section 911 is screwed into an inner hole of the cam 910 and fixed there. The outer diameter of the main body section 911 including a part inserted into the cam 910 and a stopper 922 having an increased diameter may be reduced gradually toward the base end. That is, FIG. 15 shows an example in which a diameter d2 at the base end is smaller than the diameter d1 at the tip. An operation section 506A of the hole 571B has a play relative to the operation stick 531A to prevent the main body section 911 from pushing up the piston 715 even if the operation section 506A is tilted or bent. Also, the tip of the piston 715 protruding into the shaft 701 is configured to have a correlation with the second groove 719 so that a space is formed between the piston 715 and the second groove 719. Thus, the piston 715 is prevented from interfering with the main body section 911 and therefore, the forward movement or retracting movement of the procedure instrument 504A can be smooth. In addition, the stopper 922 makes contact with a ratchet base 712 when the procedure instrument 504A is inserted through the operation stick 531A and regulates the procedure instrument 504A to prevent it from being pushed further.

Figure 21:
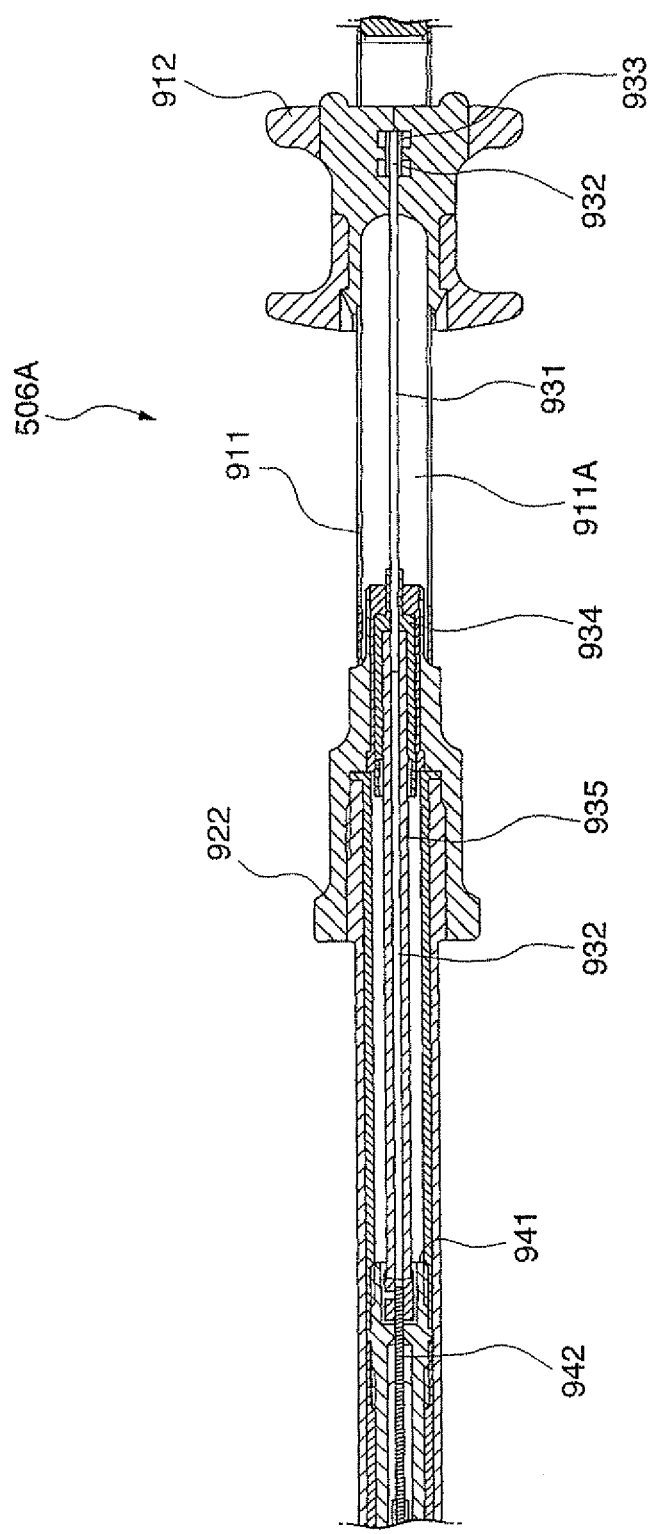
FIG. 21 is a cross-sectional view along the line AI-AI in FIG. 15.

As illustrated in FIG. 21, a pipe 931 is fixed to a slider 912. An operation wire 932 for driving the treatment section 505A is passed through the pipe 931. The base end of the operation wire 932 and the base end of the pipe 931 are locked to the slider 912 by an engagement member 933. The pipe 931 passing through a slit 911A of the main body section 911 is extendably supported by a resin-made pipe retainer 934. An operation wire 932 passing through another pipe 935 fixed to the pipe retainer 934 is extracted and enters an intermediate coupling 941 together with the pipe 935, and is inserted into a metal-made single-layered coil 942 therein. Isolation is imparted to the pipe 935 by coating it with a thermally-contracting tube.

Figure 22:
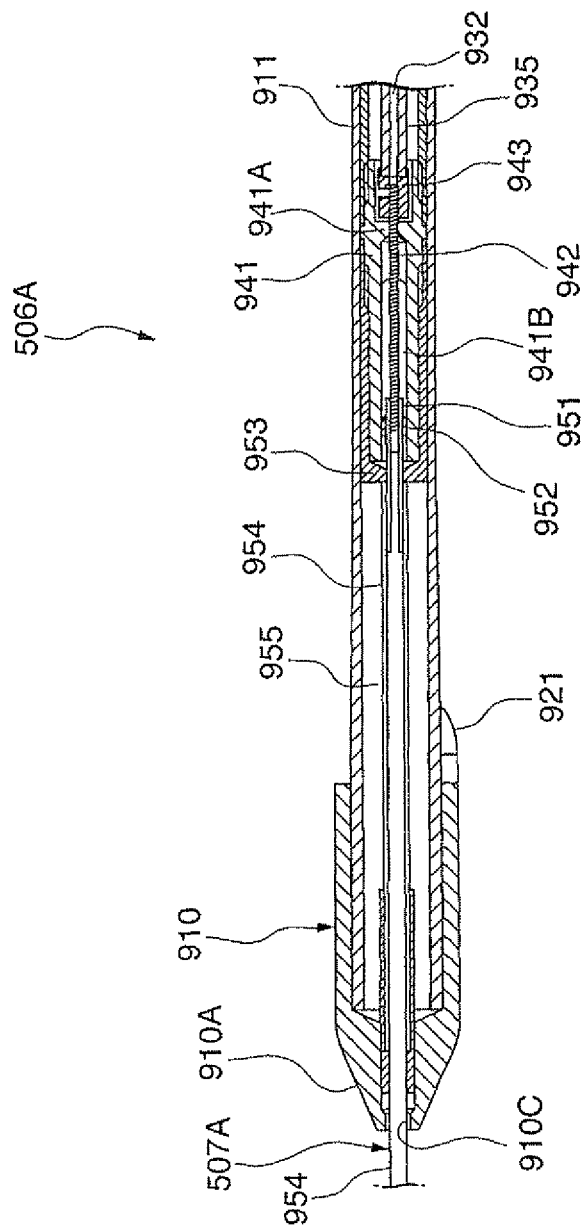
FIG. 22 is a cross-sectional view along the line AJ-AJ in FIG. 15.

As illustrated in FIG. 22, a coil receiver 943, to which the base end of the single-layered coil 942 is fixed, is housed in the base end of the intermediate coupling 941. The tip of the previously described pipe 935 is inserted into the coil receiver 943. A diameter-contracting section 941A is provided to the intermediate coupling 941 to prevent the coil receiver 943 from being removed toward the tip. The single-layered coil 942 is inserted into the multi-layered coil 951 further toward the tip than the diameter-contracting section 941A. The multi-layered coil 951 is configured to have more than three coils disposed coaxially. For example, an innermost layer coil and an outermost layer coil are wound in the same direction, and an intermediate-layer coil is wound in the opposite direction in the case of a three layer structure. This results in that rotating of the innermost layer coil and the outermost layer coil in the coil-loosening direction tightens the intermediate-layer coil, thereby causing the intermediate layer coil to interfere with the innermost layer coil. Thus, the rotation torque is transferred to the treatment section 505A at the tip. Rotating in the opposite direction causes the loosening intermediate layer coil to interfere with the outermost layer coil, thereby transferring the rotation torque to the treatment section 505A. In addition, using a metal-made multi-layered coil 951 improves the transferred rotation torque. A resin-made coil may be used for obtaining insulation.

A coil receiver 952 is brazed to the multi-layered coil 951. The coil receiver 952 is slidably inserted through a longitudinal groove 941B formed on the insulative intermediate coupling 941. Accordingly the multi-layered coil 951 can engage with the intermediate coupling 941 in the rotative direction, but not in the forward direction or the retracting direction. Meanwhile, a resin-made removal stop 953 is attached to the tip of the intermediate coupling 941. Since the removal stop 953 regulates the protrusion of the coil receiver 952, the multi-layered coil 951 will never be removed from the intermediate coupling 941. Also, the coil receiver 952 will never make contact with the main body section 911. This configuration will not affect the length of the multi-layered coil 951 even if the single-layered coil 942 contracts or extends during a medical operation.

Also, the single-layered coil 942 can be brazed to the coil receiver 943 that is slid toward the base end and extracted from the intermediate coupling 941 after brazing the multi-layered coil 951 to the coil receiver 952. Meanwhile, the intermediate coupling 941 should preferably be made of high heat-resistance resin, e.g., PEEK (polyetheretherketone) taking the high temperature applied during the brazing operation into account.

The outer periphery of the multi-layered coil 951 extracted from the intermediate coupling 941 is coated by an insulative tube 954. A fluoro resin-made insulative tube 954 has lower sliding friction, thus providing desirable rotation. The isolated and coated multi-layered coil 951 passing through a winding-protection pipe 955 is extracted from a hole 910C formed at the tip of the cam 910.

The main body section 911 should preferably be made of a metal material taking durability into account. In this case, providing insulation to the operation section 506A realizes a procedure instrument 504A for use in a medical operation with a high-frequency apparatus. Therefore, the use of a resin in the removal stop 953, intermediate coupling 941, thermally-contracting tube of the pipe 935, pipe retainer 934, and slider 912 reliably isolates the main body section 911 from the operation wire 932 and coils 942 and 951. This results in using high-frequency waves with the procedure instrument 504A such as an incision knife or high-frequency forceps. Apparatuses of this type can be used compatibly. Insulation coating onto the multi-layered coil 951 may not be necessary unless the procedure instrument is of a high frequency application-type apparatus. In this case, increasing the thickness of the multi-layered coil 951 corresponding to the thickness of the thermally contracting tube for use as a coating will provide a more rotative procedure instrument. The thickness of the thermally contracting tube utilized for the single-layered coil 942 will provide significantly more resistance against compression or expansion.

Consequently, steps for carrying out operations using the medical treatment endoscope 501 will be explained. Meanwhile, a case will be explained as follows where an endoscope is introduced from a mouth as a natural orifice of a patient, a procedure instrument is introduced from an opening formed in a stomach into an abdominal cavity to grasp tissue. It should be noted that operations can be carried out through another organ or another path. Although we concentrate on the procedure instrument 504A and the first operation unit 530A in the explanation, the procedure instrument 504B and the operation unit 530B can be used independently because they are mere symmetric components.

Figure 24:
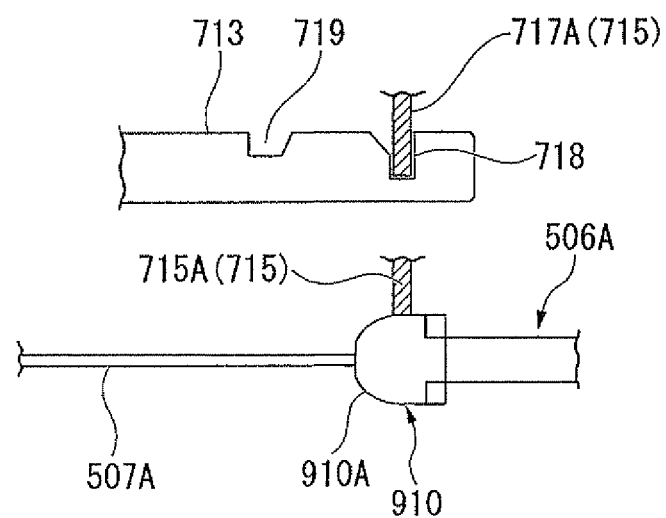
FIG. 24 illustrates the piston pushed up by the cam.

Two procedure instruments 504A and 503B are inserted into the medical treatment endoscope 501. The procedure instrument 504A is inserted into the first operation unit 530A. As schematically illustrated in FIG. 23, when the procedure instrument 504A is not inserted yet, the piston 715 provided to the ratchet base 712 at the tip of the first operation stick 531A engages with the first groove 718 of the connection plate 713 and locks the connection plate 713. Locking the connection plate 713 prevents the second bending slider 711 from moving since the ratchet base 712 is unmovable. This corresponds to a position where the second bending part 308 becomes straightened. That is, the second bending part 308 is always straightened in the medical treatment endoscope 501 when the procedure instrument 504A is inserted. As illustrated in FIG. 24, forwarding the operation section 506A into the first operation stick 531A pushes up the piston 715 with the taper surface 910A of the cam 910 at the tip of the operation section 506A. As illustrated in FIG. 25, the piston 715 being capable of moving up the inclination surface 718A of the first groove 718 of the connection plate 713 allows the second bending slider 711 to be controlled in the direction indicated by an arrow shown in the drawing.

As illustrated in FIG. 5, the insertion section 507A of the procedure instrument 504A passing through the channel 801 is introduced into a channel in the connection sheath 515. The insertion section 507A further passing through the endoscope insertion section 503 is introduced to the tip of the first arm member 302A. Similarly, the procedure instrument 504B inserted into the operation stick 531B of the operation unit 530B is introduced at the tip of the second arm member 303A.

After closing the arm sections 302A and 303A having the procedure instruments 504A and 504B previously passing therethrough, the endoscope insertion section 503 is introduced into a body cavity from an opening previously formed in a stomach wall. In addition, the endoscope insertion section 503 may be passed through an overtube previously inserted into a body.

A section to be treated is confirmed while observing with a monitor an image obtained by an endoscopic image-pickup device provided to the tip of the endoscope insertion section 503. At this time, a first operator manipulates an angle knob 512 of the endoscope insertion section 502 and bends a third bending part 203B. Furthermore, a second operator bends the second bending part 308 and the first bending part 306 if necessary.

Figure 26:
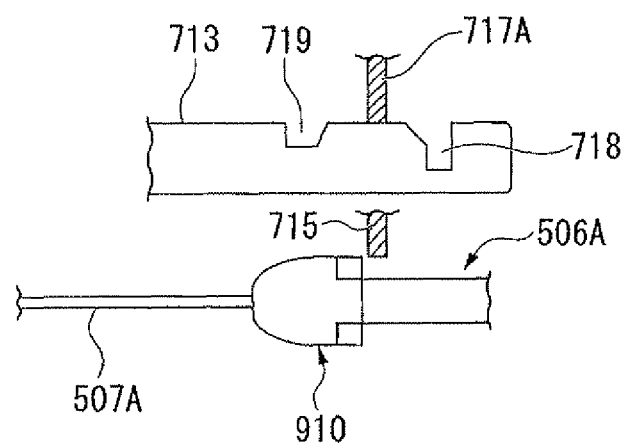
FIG. 26 illustrates the cam disposed between two grooves of the connection plate.

Bending the second bending part 308 necessitates retracting the second bending slider 711 provided to the operation sticks 531A and 531B. As illustrated in FIG. 25, retracting the second bending slider while the piston 715 is elevated causes the engagement chip 717A of the piston 715 to go up the inclination surface 718A, thereby causing the connection plate 713 to slide on the piston 715 as illustrated in FIG. 26. The second bending slider 711 cannot be further retracted after the piston 715 is housed in the second groove 719 as illustrated in FIG. 27. The second bending part 308 as illustrated in FIG. 1 bends at this position, causing the first arm member 302A to open. In addition, since the second groove 719 is shallower than the first groove 718, a space Ss is formed between the cam 910 and the main body section 911 of the operation section 506A when the piston 715 engages with the second groove 719. Absence of sliding friction between the main body section 911 and the piston 715 allows smooth extension and retraction of the main body section 911.

Furthermore, bending the first bending part 306 necessitates tilting the operation sections 506A and 506B of the procedure instruments 504A and 504B while observing the endoscopic image.

As illustrated in FIG. 4, tilting the operation section 506A upwardly relative to the operator causes the rotation shafts 564A and 565A of the first rotation mechanism 561A to rotate in accordance with the tilting angle. The rotation of the sprocket 595 attached to the rotation shafts 546A and 565*a* causes extension and retraction of the first bending wires 315A and 315B attached to the chain 622, thereby bending the first bending part 306 upwardly. In contrast, tilting the operation section 506A downwardly relative to the operator causes the rotation shafts 564A and 565A of the first rotation mechanism 561A to rotate in the direction reverse to the upward tilting direction in accordance with the tilting angle. The reverse rotation of the sprocket 595 attached to the rotation shafts 546A and 565*a* causes extension and retraction of the first bending wires 315A and 315B attached to the chain 622, thereby bending the first bending part 306 downward.

Tilting the operation section 506A in a right-hand direction relative to the operator causes the rotation shafts 584A and 585A of the second rotation mechanism 581A to rotate in accordance with the tilting angle. The rotation of the sprocket 595 attached to the rotation shafts 584A and 585A causes extension and retraction of a first-bending-downward operation wire and a second-bending-downward operation wire attached to the chain 622, thereby bending a first bending part 306 in the right-hand direction. In contrast, tilting the operation section 506A in a left-hand direction relative to the operator causes the rotation shafts 584A and 585A of the second rotation mechanism 581A to rotate in the reverse direction in accordance with the tilting angle. The rotation of the sprocket 595 attached to the rotation shafts 584A and 585A causes the first-bending-downward operation wire, the second-bending-downward operation wire, and the first bending part 306, that are attached to the chain 622 to bend in a left-hand direction.

Since the second rotation mechanism 581A is not driven when the first rotation mechanism 561A is driven, and the first rotation mechanism 561A is not driven when the second rotation mechanism 581A is driven, each bending can be obtained without being affected by these rotation mechanisms. Meanwhile, tilting the operation section 506A drives the first and second rotation mechanisms 561A and 581A in accordance with the tilting ratio with respect to the vertical and horizontal directions, thereby bending the first bending part 306 diagonally in a direction the same as the tilting direction of the operation section 506A. Since the center or barycenter of the operation stick 531A in the longitudinal direction is configured to substantially coincide with the positions of the rotation shafts 546A, 565A, 584A, and 585A, the operation stick 531A and the operation section 506A of the procedure instrument 504A during hands-free operation by the operator will not descend with gravity; therefore, erroneous operation can be prevented.

A necessary force is optimized to operate the first bending part 306 by means of a non-electric wire-assisted operation. To be more specific, a portion of the operation stick 531A operated by the operator who inputs a force is decelerated by separating and offsetting the portion from the rotation shafts 546A, 565A, 584A, and 585A. As illustrated in FIG. 6, since a deceleration ratio is obtained corresponding to a ratio between a distance Lr an a radius Rs of the sprocket 595, the bending operation can be carried out with a small force while downsizing the operation section 520. In this case the distance Lr indicates the length between the base end section of the operation section 506A of the procedure instrument 504A. In addition, the deceleration enhances resolution, thereby enabling accurate bending operation.

As illustrated in FIGS. 5 and 6, since the point of the second rotation mechanism 581A to which a force is transmitted from the first operation stick 531A is offset toward the tip relative to the rotation shafts 564A and 565A such as a roller bearing 572A as illustrated in FIG. 6, the force necessary at the transfer position is decreased, and friction among components can be reduced. This decreases the rigidity required for components used there and obtains a small and lightweight operation section 520. Also, the use of the ball roller 572A at the point of the second rotation mechanism 581A to which the force is transferred from the first operation stick 531A reduces the friction due to the second rotation mechanism 581A when rotating the first operation stick 531A vertically, thereby reducing the necessary force for the vertical operation.

Grasping tissue necessitates adjusting the position of a forceps member that is opened or closed by the operation section 506A of the procedure instrument 504A. For example, pushing the operation section 506A into the first operation stick 531A causes the treatment section 505A to protrude further from the first arm member 302A. Also, retracting the operation section 506A from the first operation stick 531A causes the treatment section 505A to be retracted into the first arm member 302A. As illustrated in FIG. 28, since this state of the cam 910 is hooked on the piston 715, the procedure instrument 504A will not be removed from the first operation stick 531A undesirably.

Adjusting the direction of the procedure instrument 504A around the axial line necessitates the main body section 911 of the operation section 506A to rotate around the axial line. Thus, rotational torque is input into the multi-layered coil 951 that is engaged to the intermediate coupling 941 in the rotational direction as illustrated in FIGS. 21 and 22. In the multi-layered coil 951, two coils adjacent to each other in a radial direction interfere with each other while they are tightened or loosened based on their combination of the winding direction and the rotational direction of the operation section 506A and thus, rotational torque is transferred. Since the treatment section 505A is fixed to the tip of the multi-layered coil 951, the transferred rotational torque rotates the treatment section 505A around the axial line. The rotation in the vicinity of the operator's hand is stopped after confirming that a desirable direction is obtained by means of an endoscopic image.

The slider 912 is forwarded after adjusting the direction and position of the treatment section 505A. The operation wire 932 moves an opening-and-closing mechanism of the treatment section 505A to open a pair of forceps members. The single-layered coil 942 receives an extension force generated by pushing the operation wire 932. The extension force is not applied to the multi-layered coil 951 because the multi-layered coil 951 is not engaged with the operation section 506A in the extension and retraction directions. This allows the treatment section 505A to be adjusted even if the forceps members are opened. Consequently, retracting the slider 912 causes the forceps members to close and grasp tissue. The compression force generated temporarily is received by the single-layered coil 942.

The procedure instruments 504A and 504B are retracted from the medical treatment endoscope 501 after completing necessary treatments. The procedure instruments 504A and 505B are also retracted from the medical treatment endoscope 501 in order to exchange procedure instruments necessary for a treatment. As illustrated in FIG. 28, the operation section 506A is rotated around the axial line after the cam 910 abuts the piston 715. The piston 715 is pushed up along the tilted side surface 921A of the blade section 921 of the cam 910. As illustrated in FIG. 29, providing the tilted side surface 921A enables pushing up of the piston 715 with a small force. Meanwhile, as illustrated in FIGS. 19 and 20, the procedure instrument 504A will never be rotated excessively if the gap surface 921B is provided. Furthermore, providing the slope 921C facilitates offsetting the piston 715 from the cam 910 in an axial line direction (thrust direction), thereby removal is easy. Meanwhile, it is preferable that the entire cam 910 be made of a metal in view of breakage protection. In addition, the cam 910 may be made of POM (polyoxymethylene) that has desirable slidability in view of facilitating operation in extension and retraction operations in the first operation stick 531A.

However, the treatment sections 505A and 505B cannot be removed if the second bending part 308 of the arm sections 302A and 303A is opened, and the engagement of the piston 715 and the cam 910 can be released. The piston 715 pushed up by the cam 910 in the operation section 520 is configured to automatically restore the second bending part 308 to a straightened state. That is, pushing up the piston 715 and releasing the engagement with the second groove 719 retract the second bending slider 711 with tension applied by the second bending wires 316A and 316B and a resilience of the coil spring 745. This results in causing the second bending part 308 to restore into the straightened state. In addition, a resilient part like the spring 792 as illustrated in FIG. 13 may be added to prevent energetic restoration of the second bending slider 711. Consequently, the medical treatment endoscope 501 is removed from the body after removing the procedure instrument 504A.

Next, a modified example of the present embodiment will be described as follows.

Figure 30:
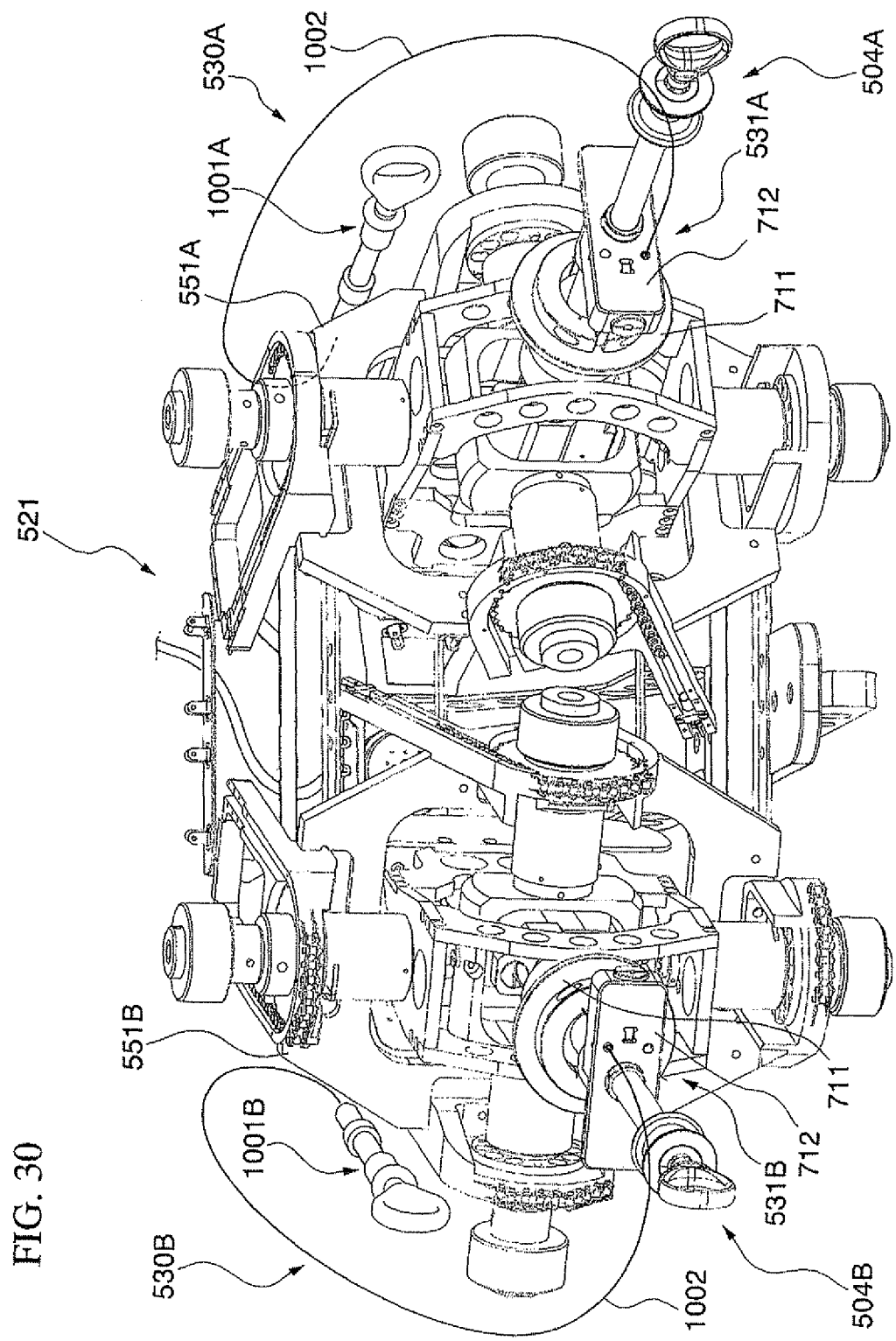
FIG. 30 illustrates a base having an operation section joined to a second bending slider disposed on a side of a base.
Figure 31:
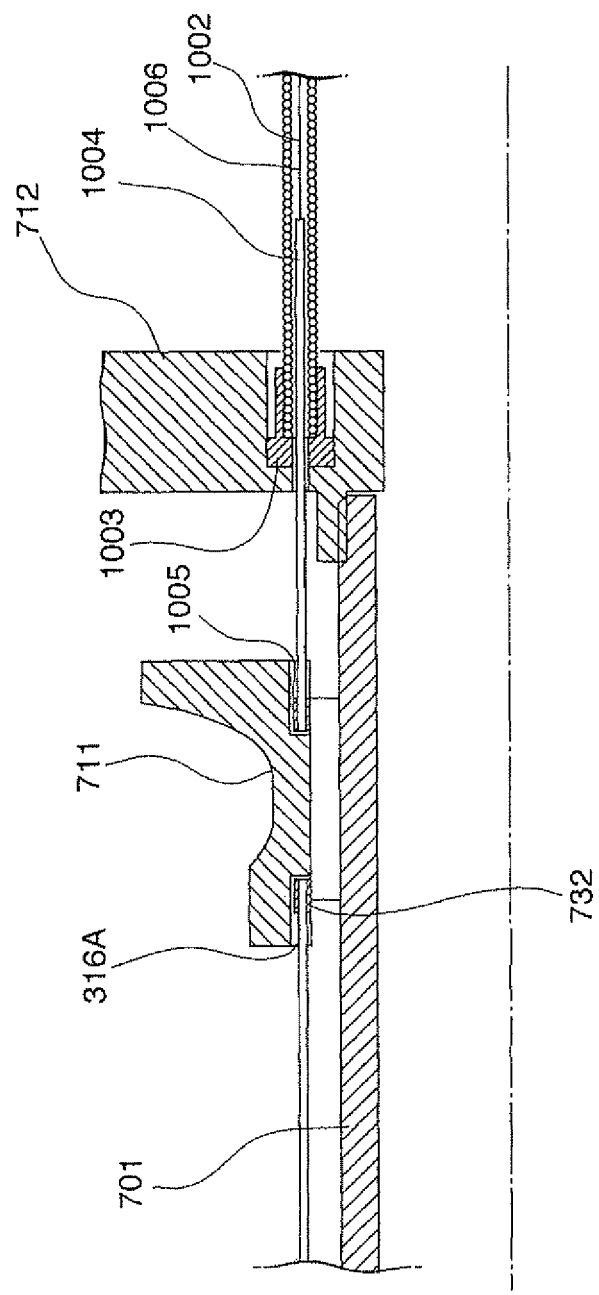
FIG. 31 is a cross-sectional view illustrating a mechanism for joining the second bending slider to the operation section in the configuration shown in FIG. 30.

As illustrated in FIG. 30, the operation sections 1001A and 1001B each for operating the second bending slider 711 may be fixed to the brackets 551A and 551B in parallel with each axial line of the operation sticks 531A and 531B. The operation sections 1001A and 1001B each have an extendable and retractable slider. Moving the slider causes the wire in the coil sheath 1002 to be extended or retracted. As illustrated in FIG. 31, the coil sheath 1002 is fixed to the coil receiver 1003 attached to the ratchet base 712. A pipe 1004 is passed through the coil receiver 1003. The pipe 1003 passing through the coil sheath 1002 is rotatively engaged with the second bending slider 711 via the wire receiver 1005 together with the second bending wires 316A, 316B. A wire 1006 joined to the sliders of the operation sections 1001A and 1001B is passed through the pipe 1004. Retracting the sliders of the operation sections 1001A and 1001B moves the wire 1006, thereby drawing the second bending slider 711 and opening the second bending part 308. In this configuration, the operation section 520 can be downsized and thus, operation of the second bending part 308 can be facilitated. Also, this configuration prevents the movement of the operation sticks 531A and 531B during the operation of the second bending part 308. Thus, grasped tissue will never be moved unexpectedly.

Figure 32:
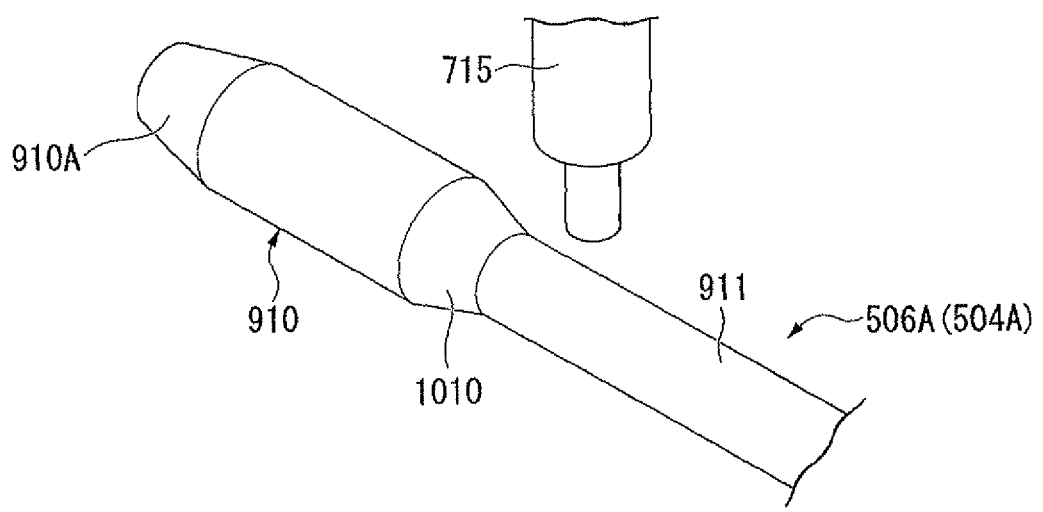
FIG. 32 shows a modified example of the cam.

As illustrated in FIG. 32, the base end of the cam 910 may be the inclination surface 1010. Drawing the procedure instrument 504A from the first operation stick 531A causes the piston 715 to move up the inclination surface 1010, thereby removing the procedure instrument 504A. The procedure instrument 504A cannot be removed with a force based on the retraction of the procedure instrument 504A toward the operator during a treatment. Further additional force will provide retraction. In this configuration, the procedure instrument 504A can be removed without rotating the operation section 506A.

Figure 33:
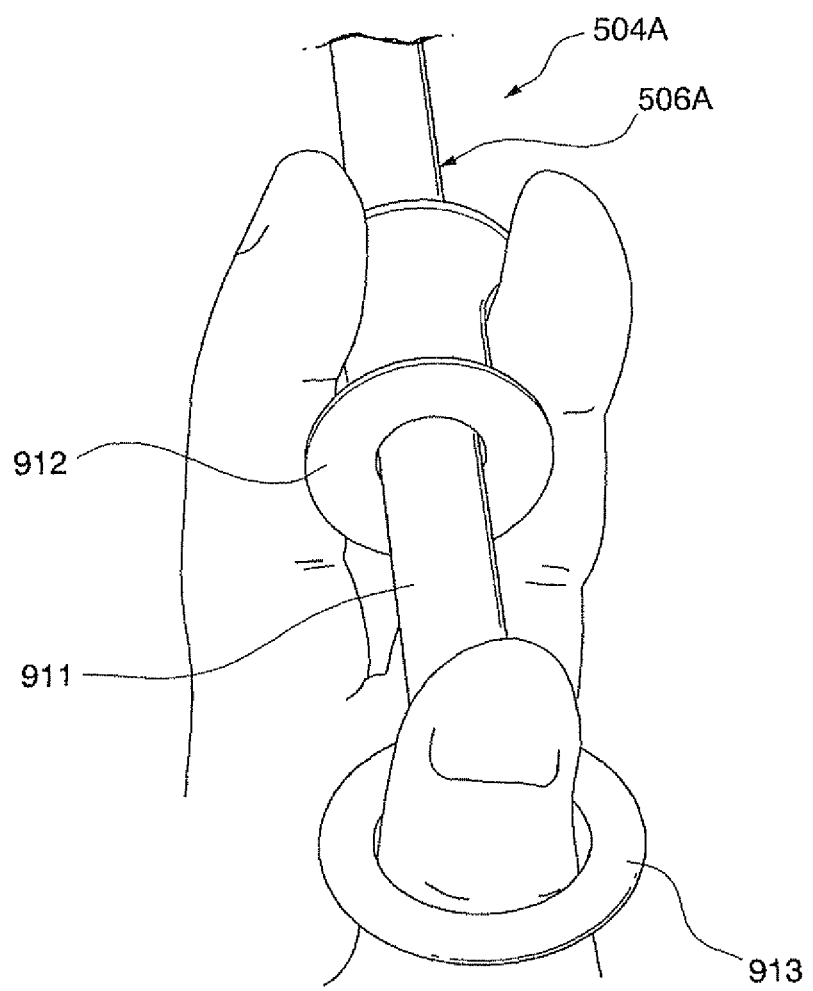
FIG. 33 illustrates a feed operation for the procedure instrument.
Figure 34:
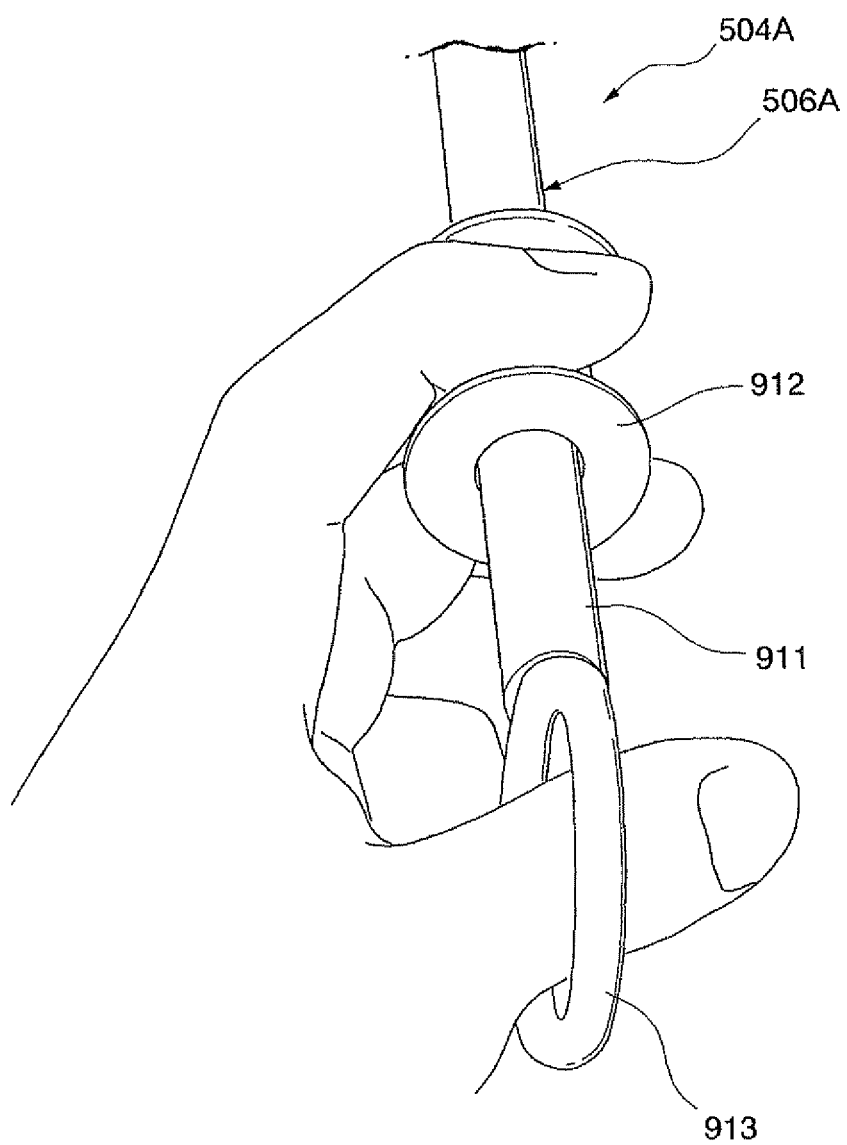
FIG. 34 illustrates a feed operation for the procedure instrument.

In addition, operations for significant rotations of the procedure instruments 504A and 504B will be explained with reference to FIGS. 33 and 34. This includes cases where we intend to adjust the treatment section 505A in the optimum direction to grasp tissue. As illustrated in FIG. 33, the slider 912 is held with an index finger and a middle finger. The hand-held state of the slider 912 is rotated in a clockwise direction by 90°. The index finger and the middle finger are withdrawn from the slider 912 after rotating the slider 912 and the main body section 911 to the positions illustrated in FIG. 34. The hand not holding the slider 912 is rotated in a counterclockwise direction by 90° to the position illustrated in FIG. 33. This state of the insertion section 507A of the procedure instrument 504A has friction relative to channels in a first operation stick 531A and the second arm member 302A. To be more specific, the channels are a channel 801, a channel in the connection sheath 515, and a channel in the endoscope insertion section 503. Therefore, the insertion section 507A will not rotate in the counterclockwise direction with a mere touch with the slider 912 and thus, its disposition is maintained. Repeating the above steps enables 90° feed operation of the procedure instrument 504A.

Figure 35:
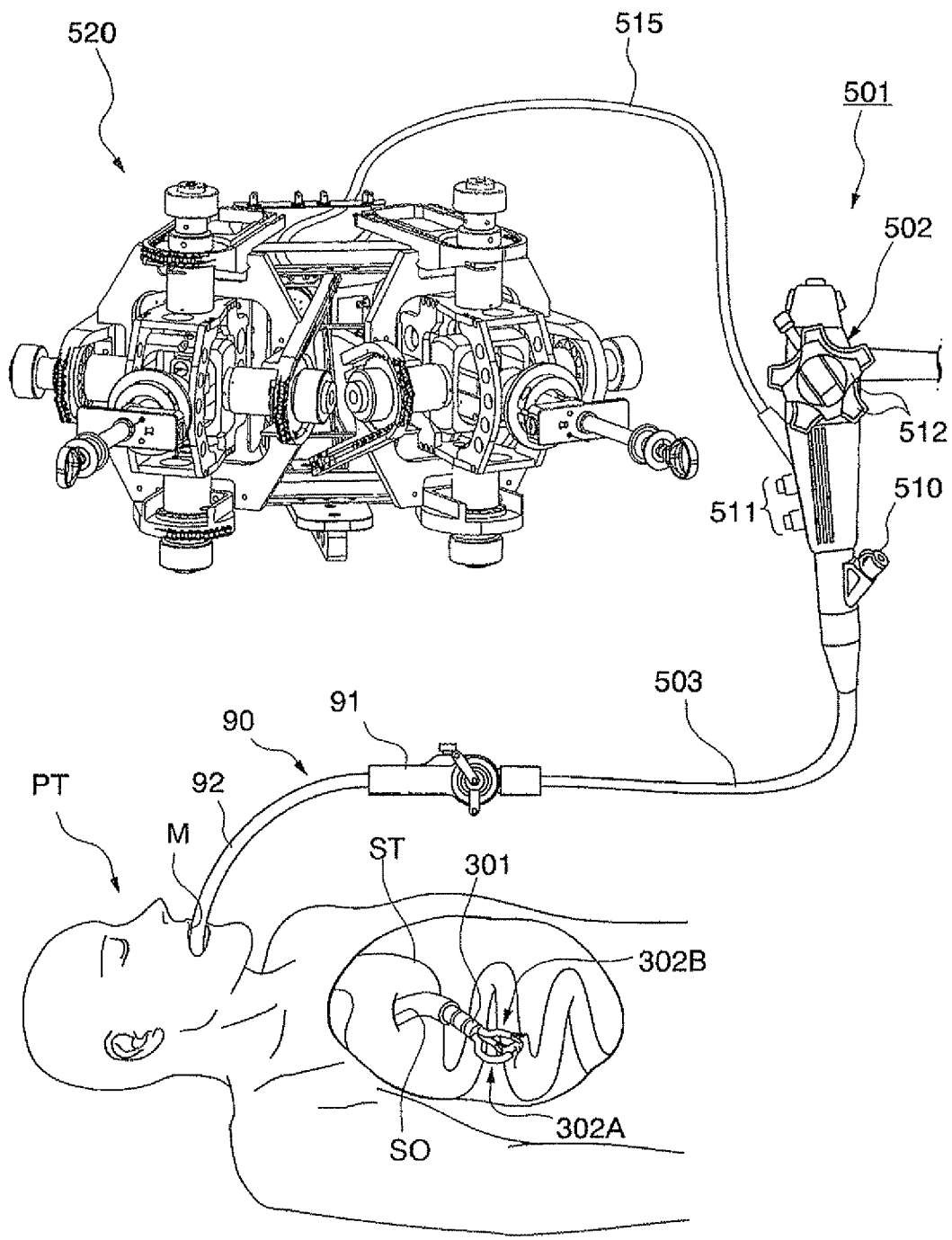
FIG. 35 illustrates a combined use of the medical treatment endoscope and an overtube.

As illustrated in FIG. 35, the medical treatment endoscope 501 may be passed through the overtube 90. The first operator handling the endoscope insertion section 502 conducts ordinary endoscopic operation with his/her left hand while operating the endoscope insertion section 503 and overtube 90 with his/her right hand. The use of bending of the overtube 90 improves the approachability to the object position in the abdominal cavity.

Second Embodiment

A medical treatment endoscope according to the present embodiment has an arm section; an operation section detachable from the arm section; and a wire, detachable from the arm section, for transferring the operation provided by the operation section.

Figure 36:
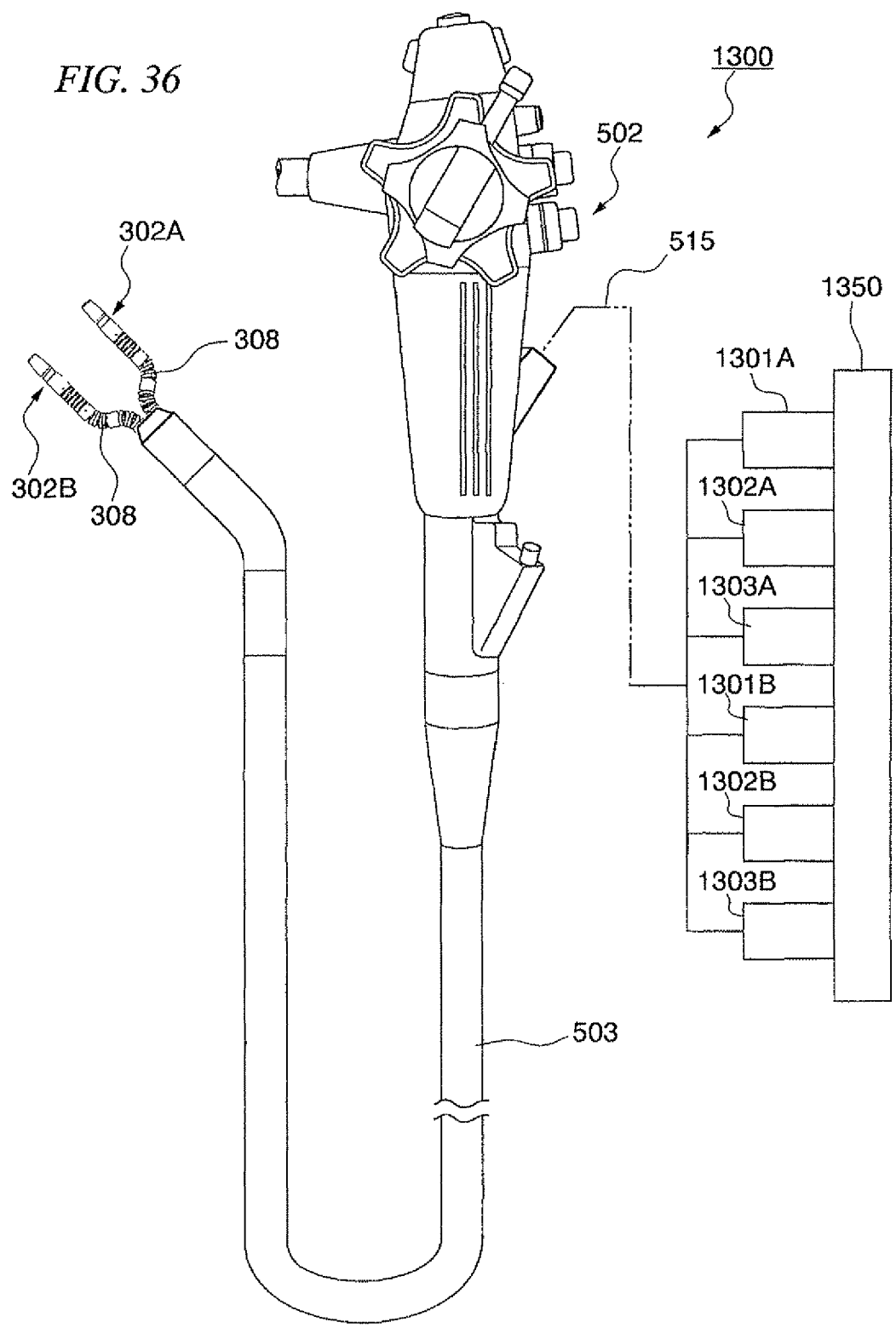
FIG. 36 shows the structure of the medical treatment endoscope according to the second embodiment of the present invention.

FIG. 36 is a view showing the structure of a medical treatment endoscope 1300 according to the present embodiment. The medical treatment endoscope is provided with the endoscope insertion section 502 and the endoscope insertion section 503 which are the same as those of the first embodiment; and an operation section 1350 having substantially the same basic structure as that of the operation section 520. As illustrated in FIG. 36, two arm sections 302A and 302B extend from the endoscope insertion section 503. A viewing device, not shown in the drawing, for observing the arm sections 302A and 302B is attached to the tip of the extruding sheath 301. A wire for transmitting the operation of an operation section 1350 to the arm sections 302A and 302B is connected through a connection sheath 515 to a wire unit (attachment section), which is detachable from the operation section 1350. Three wire units provided to each arm section are two first wire units including a vertically moving first wire unit 1301 and a horizontally moving second wire unit 1302; and a second-bending-wire unit 1303. Therefore, the present embodiment is provided with six wire units in total, i.e., the wire units 1301A, 1302A, and 1303A that are connected to the first arm section 302A and the wire units 1301B, 1302B, and 1303B that are connected to the second arm section 302B.

Figure 37:
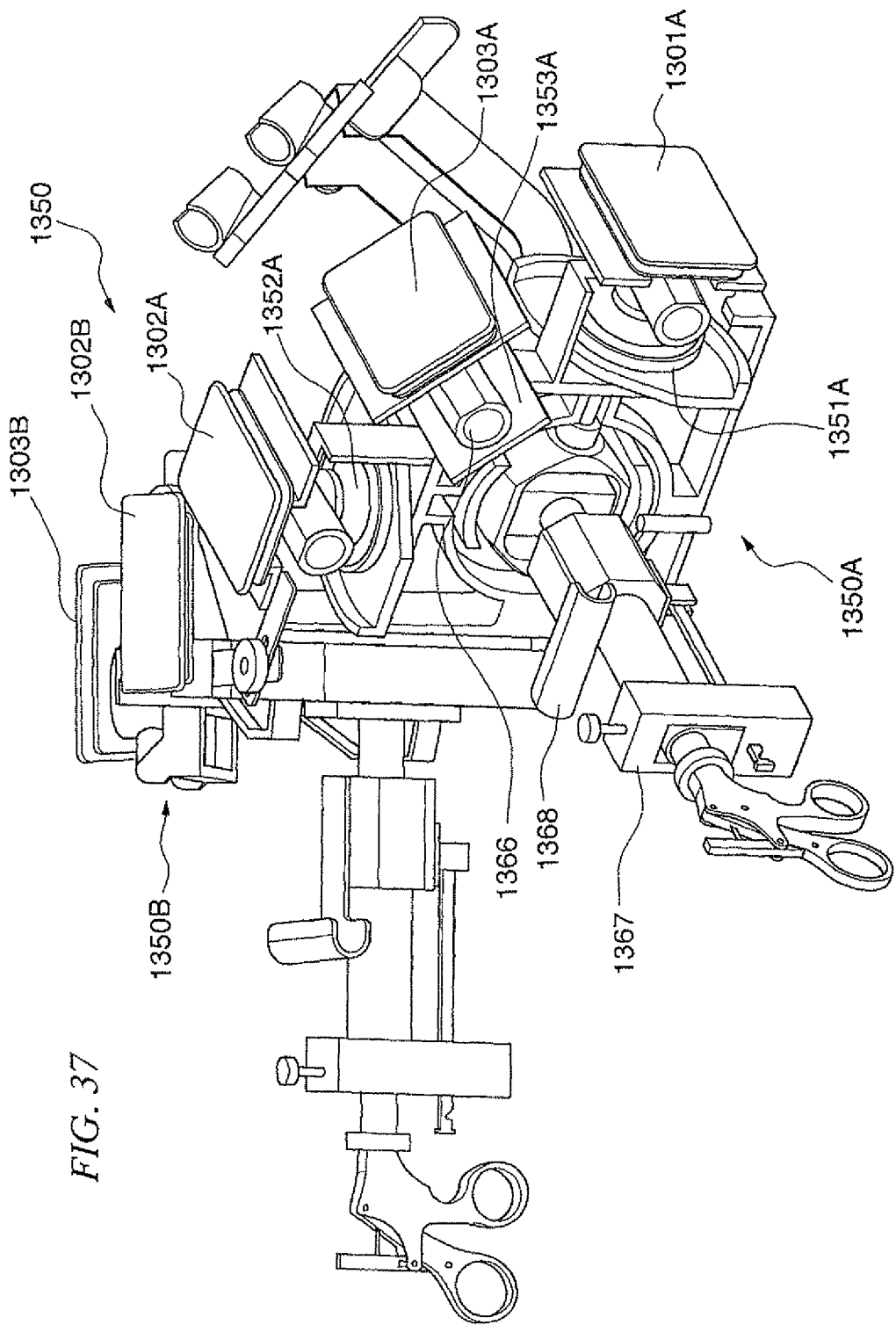
FIG. 37 shows an operation section of the medical treatment endoscope.

FIG. 37 is a view showing an operation section 1350. The operation section 1350 having substantially the same structure as the operation section 520 of the first embodiment includes a first operation unit 1350A for maneuvering the first arm section 302A; and a second operation unit 1350B for maneuvering the second arm section 302B.

The first wire units 1301A and 1301B are attached to first rotation mechanisms 1351A and 1351B of the operation units 1350A and 1350B, not shown in the drawing, respectively. The second wire units 1302A and 1302B are respectively attached to second rotation mechanisms 1352A and 1352B of each operation unit, not shown in the drawing. In each operation unit, the second bending wire units 1301A and 1303B are attached detachably to second bending-operation-mechanisms 1353A and 1353B, not shown in the drawing, provided between the first rotation mechanism and the second rotation mechanism.

Figure 38:
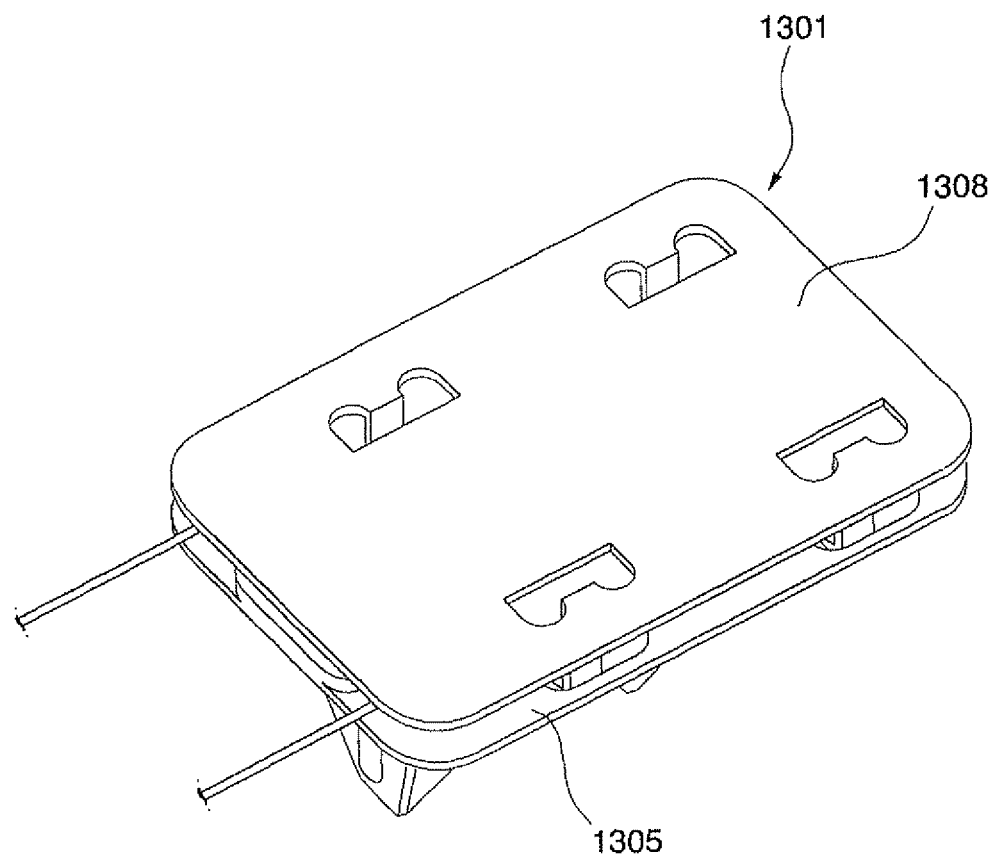
FIG. 38 is a perspective view showing a first wire unit.
Figure 39:
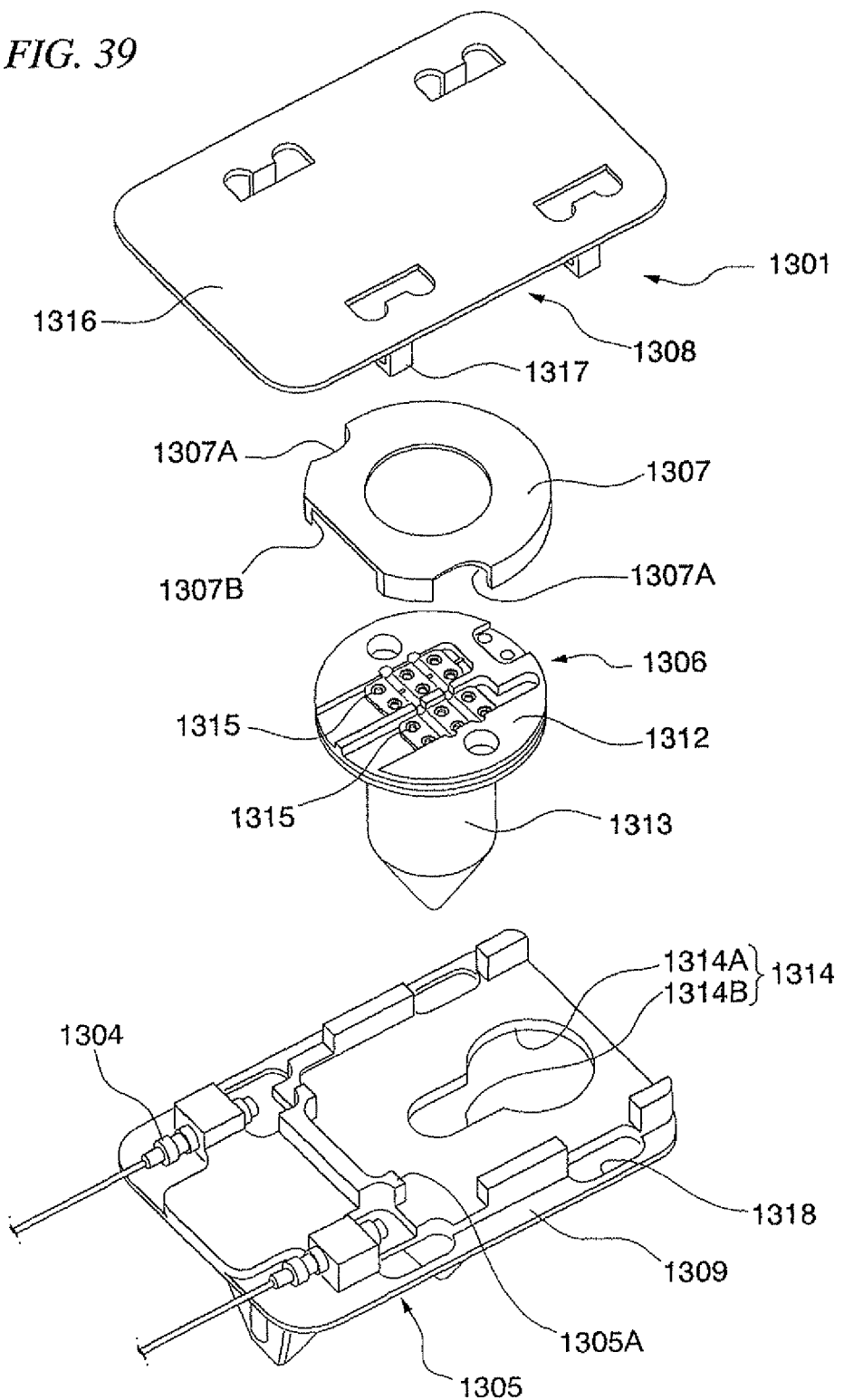
FIG. 39 shows the first wire unit in exploded view.

FIG. 38 is a perspective view showing the first wire unit 1301. FIG. 39 shows the first wire unit 1301 in exploded view. It should be noted that the second wire unit 1302 has the same structure except having a wire connected thereto.

As illustrated in FIGS. 38 and 39, the first wire unit 1301 is provided with a coil 1304 having a wire extending from the arm section and being inserted therethrough; a coil base 1305 having the coil 1304 fixed thereon; a pulley (attachment member) 1306 having the wire wound therearound and being inserted into the coil base 1305; a freely rotatable wire cover 1307 attached to the pulley 1306; and a unit cover 1308 attached to the coil base 1305.

Figure 40:
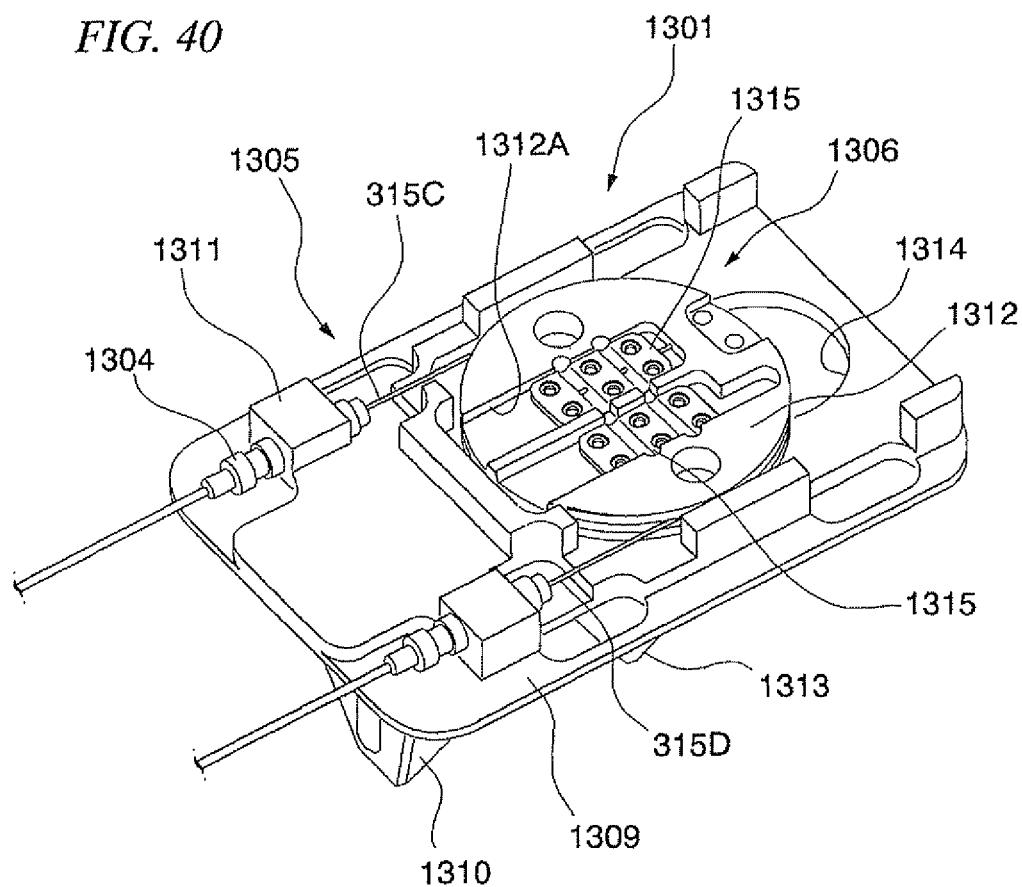
FIG. 40 shows the first wire unit except for a unit cover and a wire cover.

FIG. 40 shows the first wire unit 1301 except for the unit cover 1308 and the wire cover 1307. The coil base 1305, made from a resin, etc., has a base section 1309 having various mechanisms thereto; and a protruding section (first protruding section) 1310 protruding downward from the base section 1309. In addition, coils 1304 are fixed to both ends of one of the end sections via a fixed member 1311.

Figure 41:
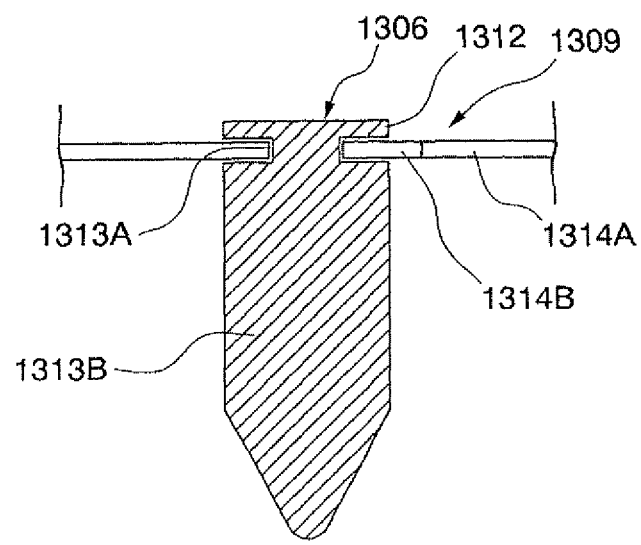
FIG. 41 is a cross-sectional view of a pulley inserted into a base section of the first wire unit.

FIG. 41 is a cross-sectional view of the pulley 1306 inserted through the base section 1309. As illustrated in FIG. 41, the pulley 1306 has a disk section 1312 having the wire extending from the arm section and being wound therearound; and an attachment section (second protruding section) 1313 extending beneath the disk section 1312. The attachment section 1313 has a first attachment section 1313A, disposed beneath the disk section 1312, having a diameter smaller than that of the disk section 1312; and a second attachment section 1313B, disposed beneath the first attachment section 1313A, having a diameter greater than that of the first attachment section 1313A. The freely rotatable attachment section 1313 of the pulley 1306 is inserted into a hole section 1314 provided onto the base section 1309 of the coil base 1305. As illustrated in FIG. 39, the hole section 1314 has a round hole 1314A having a diameter greater than that of the second attachment section 1313B; and a groove 1314B having a diameter greater than that of the first attachment section 1313A and smaller than that of the second attachment section 1313B. Therefore, the disk section 1312 is positioned above the base section 1309, and the attachment section 1313 protrudes downward relative to the base section 1309. In addition, the pulley 1306 is disposed so that the first attachment section 1313A is positioned in the groove 1314B.

The wires 315C and 315D connected to the arm sections and inserted through the coils 1304 protrude from the fixed members 1311 disposed on both ends thereof. The wires 315C and 315D each wound around the outer periphery of the disk section 1312 are inserted into the disk section 1312 from the end section opposite the fixed member 1311 of the disk section 1312. A groove 1312A is provided on an upper surface of the disk section 1312, and the end sections of the wires 315C and 315D are exposed in the groove 1312A. In addition, the end sections of the wires 315C and 315D are fixed to the disk section 1312 by the wire-fixing members 1315. In this way, the wires 315C and 315D are connected to the pulley 1306 in one unit.

It should be noted that FIG. 40 shows a mere example of fixture. That is, as to which one of the horizontally disposed wires 315C and 315D is inserted through the fixed member 1311 is determined in consideration of positions associated with attaching them onto the operation section 1350 so that maneuvering of the operation section 1350 provides appropriate operations of the arm sections 302A and 302B.

Figure 42:
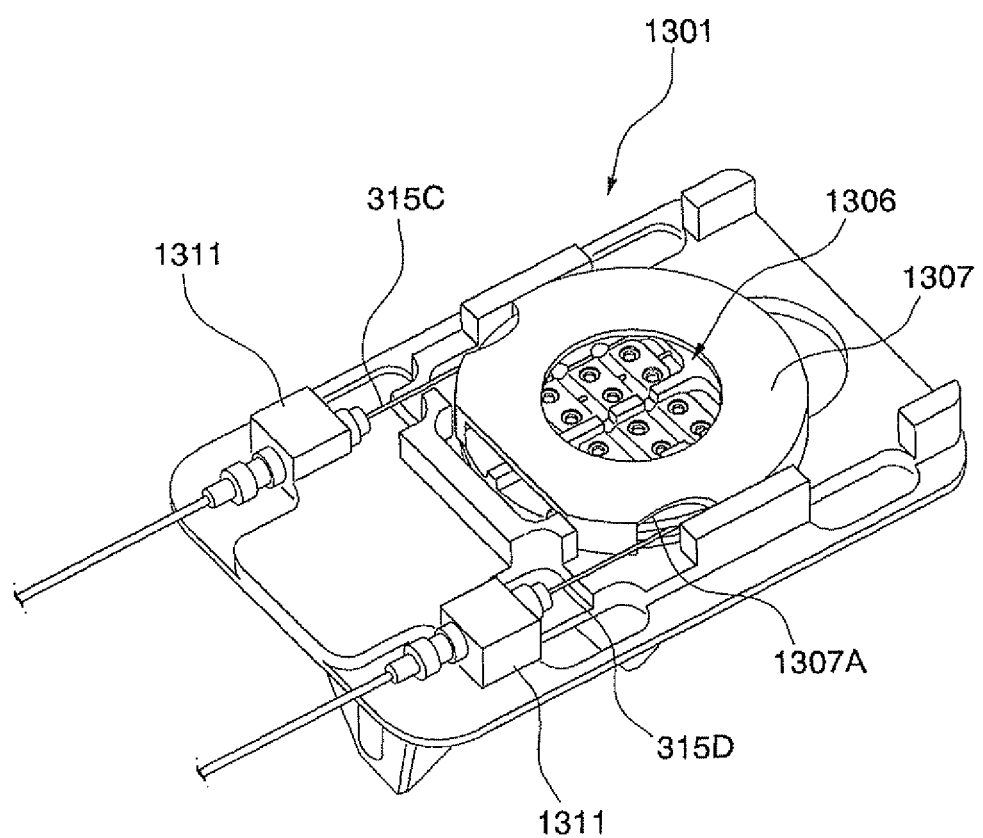
FIG. 42 shows the first wire unit except for the unit cover.

As illustrated in FIGS. 39 and 42, a substantial disk wire cover 1307 is attached on the pulley 1306, and the wire cover 1307 pushes the wire-fixing member 1315. The diameter of the wire cover 1307 is greater than that of the disk section 1312 of the pulley 1306. The lateral surface formed in the circumferential direction of the wire cover 1307 covers the outside of the wires 315C and 315D wound around the pulley 1306.

A notch 1307A for passing the wire therethrough and a plane section 1307B making contact with the coil base 1305 are formed to the wire cover 1307. As illustrated in FIG. 42, the wires 315C and 315D protruding from the fixed member 1311 are wound around the pulley 1306 through the notch 1307A. The plane section 1307B makes contact with the protrusion 1305A formed on the coil base 1305. This limits the rotation of the wire cover 1307, i.e., rotation of the pulley 1306 does not cause the wire cover 1307 to rotate. Therefore, this prevents the wires 315C and 315D from making contact with the wire cover 1307 since the position of the wire cover 1307 and the notch 1307A do not change and correlation relative to the fixed member 1311 is maintained.

As illustrated in FIG. 39, the unit cover 1308 is provided with a main body 1316 greater than the base section 1309 of the coil base 1305; and four engagement holes 1317 extending downward from the vicinity of the periphery of the main body 1316. Attaching the unit cover 1308 from above the base section 1309 so that the four engagement holes 1318 provided on the base section 1309 engage with engagement claws 1317 provides unitary assemble with the coil base 1305, thereby preventing floating of the wire cover 1307.

Freeplay is provided between the engagement claws 1317 and the engagement holes 1318 in an engaged state while engagement is maintained so that the engagement claws 1317 are movable by a predetermined length, e.g., several millimeters in the engagement hole 1318 in the width direction and in the longitudinal direction relative to the coil base 1305. Therefore, the unit cover 1308 unitarily assembled with the coil base 1305 is movable relative to the coil base 1305 by the predetermined length in the width direction and in the longitudinal direction with respect to the coil base 1305.

Figure 43:
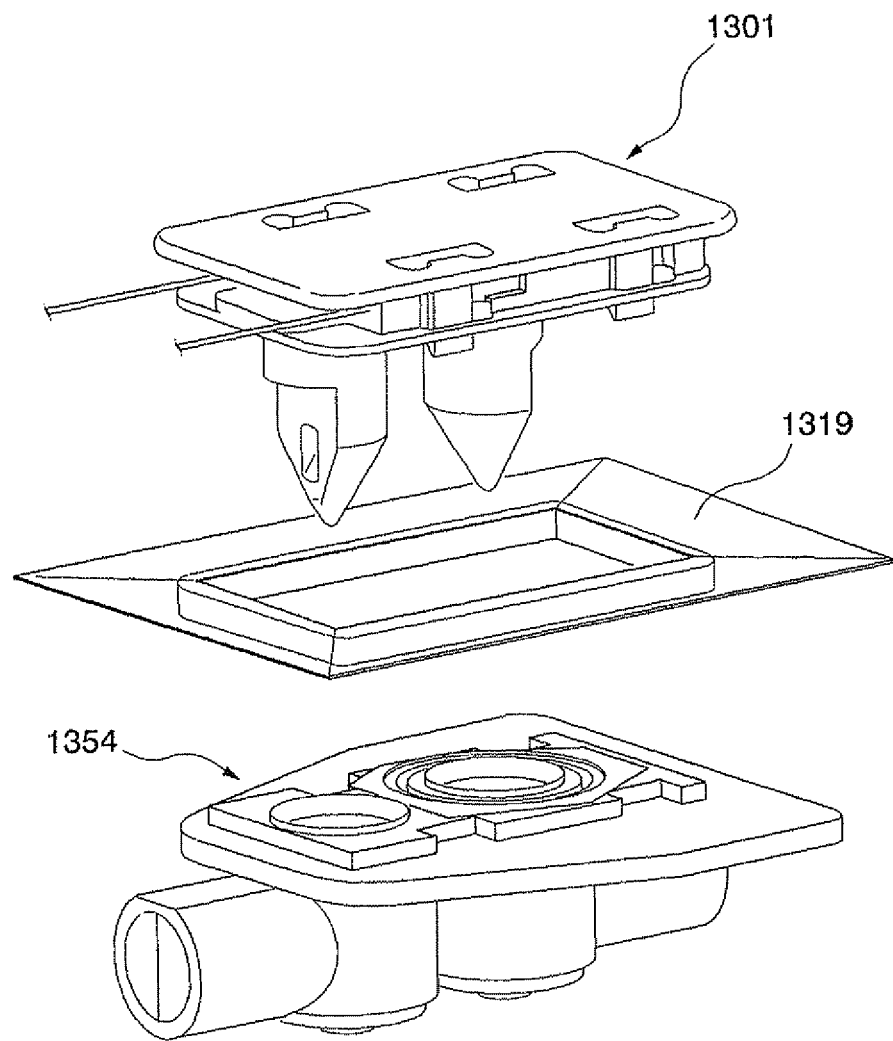
FIG. 43 shows the first wire unit and a first mating attachment section.

FIG. 43 illustrates the first wire unit 1301 and a first-mating attachment section 1354 provided to the first rotation mechanism 1351 of the operation section 1350. A pollution-preventive drape 1319 is placed between the first wire unit 1301 and the first-mating attachment section 1354 having the drape 1319 attached thereon. An attachment procedure thereof will be explained later.

Figure 44:
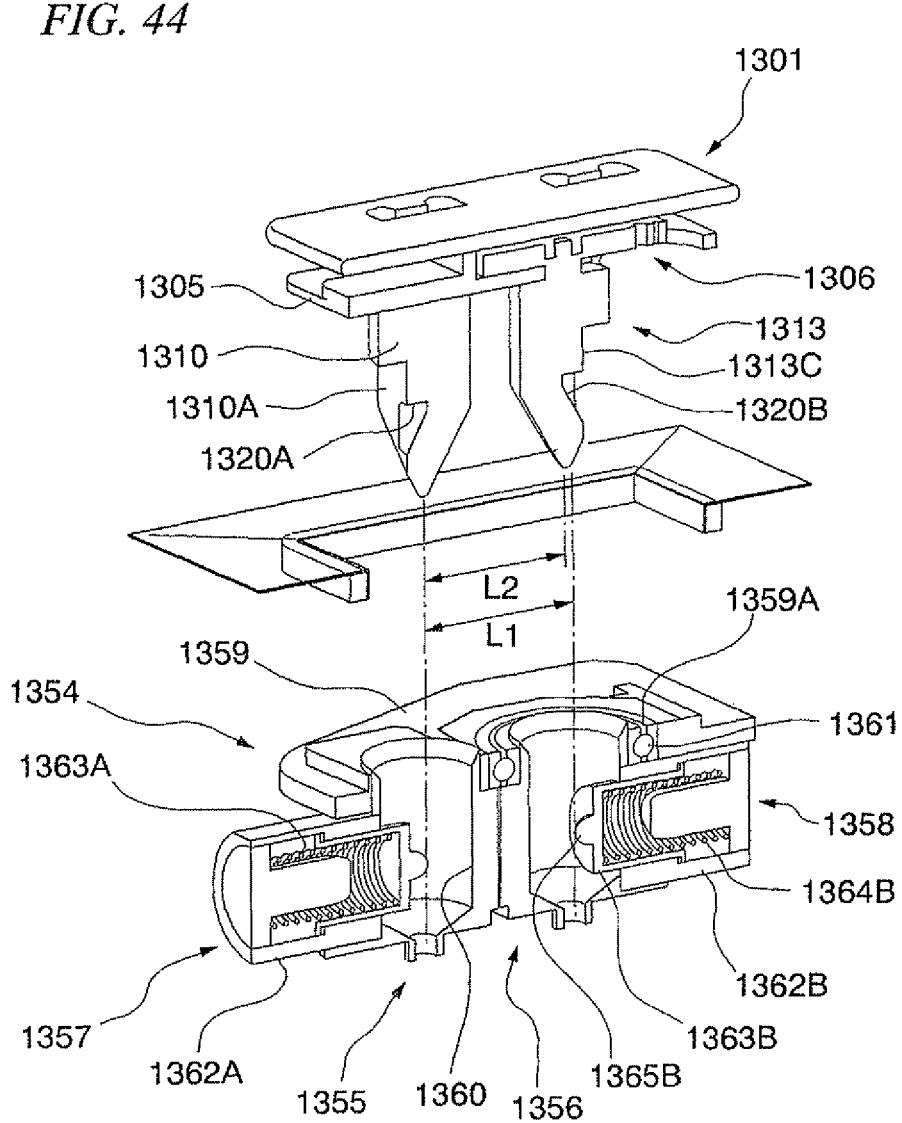
FIG. 44 is a cross-sectional view of FIG. 43.

FIG. 44 is a cross-sectional view of FIG. 43. A protruding section 1310 of the coil base 1305 and the attachment section 1313 of the bending-wire unit 1303A protrude downward relative to the first wire unit 1301. The protruding section 1310 and the attachment section 1313 having substantial cylindrical shapes have taper tips which gradually reduce in diameter. Partly notched outer peripheries excluding the tapered tips form second outer peripheries 1310A and 1313C that are parallel with the axial line of the attachment section 1313. The cross-sections, in both the protruding section 1310 and the attachment section 1313, orthogonal to the axial line passing through a second outer periphery has a D-letter shape since the second outer peripheries 1310A and 1313C are planes having zero curvature.

Fitting-holes 1320A and 1320B for engaging with the first-mating attachment section 1354 are provided to the second outer peripheries 1310A and 1313C inwardly with respect to radial direction respectively. The direction of the fitting-hole 1320A, currently having an opening directed to the coil 1304, may be different. In addition, the direction of the fitting-hole 1320B of the attachment section 1313 varies based on the rotation of the pulley 1306. The wires 315C and 315D are connected with the pulley 1306 so that the arm sections are in parallel with the axial line of the insertion section of the endoscope in an initial state while the fitting-hole 1320B has an opening directed opposite the coil 1304 as illustrated in FIG. 44.

In addition, the opening shapes of the fitting-holes 1320A and 1320B on the second outer peripheries 1310A and 1313C are elongated in the axial line directions of the protruding section 1310 and the attachment section 1313. The fitting-holes 1320A and 1320B each are formed to have taper shapes wherein the holes become shallower in the vicinity of the tips of the protruding section 1310 and the attachment section 1313. Taper angles of the fitting-holes 1320A and 1320B set to have 30 to 40 degrees facilitate attachment strength and detachability compatibly.

The first-mating attachment section 1354 is provided with: a first insertion section 1355 having the protruding section 1310 inserted therethrough; a second insertion section 1356 attached to the first insertion section 1355 detachably and having the attachment section 1313 inserted therethrough; a first support section 1357 for supporting the protruding section 1310 and the first insertion section 1355 unitarily and detachably; and a second support section 1358 for supporting the attachment section 1313 and the second insertion section 1356 unitarily and detachably.

The first insertion section 1355 has a plane base section 1359 and a non-rotative and substantial cylindrical insertion hole 1360 attached to the base section 1359. The substantial cylindrical second insertion section 1356 is attached to a hole 1359A provided to the base section 1359 via a bearing 1361. That is, the second insertion section 1356 is freely rotative relative to the base section 1359. Rotating the rotation shaft of the first rotation mechanism 1351 connected to the second insertion section 1356 causes the second insertion section 1356 to rotate in synchronization.

In addition, the end surfaces of the insertion hole 1360 and the second insertion section 1356 in the vicinity of the base section 1359 are chamfered to facilitate the insertion of the protruding section 1310 and the attachment section 1313.

The first support section 1357 and the second support section 1358 having substantially the same structures have fixed sections 1362A and 1362B fixed to the insertion hole 1360 and the second insertion section 1356 respectively; and fitting members 1363A and 1363B enclosed in the fixed section 1362. The second support section 1358 having substantially the same structure and movement as those of the first support section 1357 will be explained as follows.

The substantial cylindrical fixed section 1362B of the second support section 1358 is attached to an outer periphery of the second insertion section 1356 so that axial lines cross orthogonally with each other. In addition, the maneuvering amount of the first rotation mechanism 1351 is set to be an initial state, i.e., zero when the axial line of the second support section 1358 is in parallel with the line obtained by connecting the axial line of the insertion hole 1360 and the axial line of the second insertion section 1356. The substantial cylindrical fitting protrusion 1363B having a diameter smaller than that of the fixed section 1362B is enclosed in the fixed section 1362B. An urging member 1364B, e.g., a spiral spring placed between the fixed section 1362B and the fitting protrusion 1363B urges the fitting protrusion 1363B toward the second insertion section 1356. The wall surface of the second insertion section 1356 cut partially corresponding to the fixed section 1362B attached thereto allows the fitting protrusion 1363B to protrude into the second insertion section 1356 by a predetermined length by the urging force of the urging member 1364B. A fitting protrusion 1365B having a shape engageable with the fitting-hole 1320B is provided on the tip of the fitting protrusion 1363B.

Figure 45:
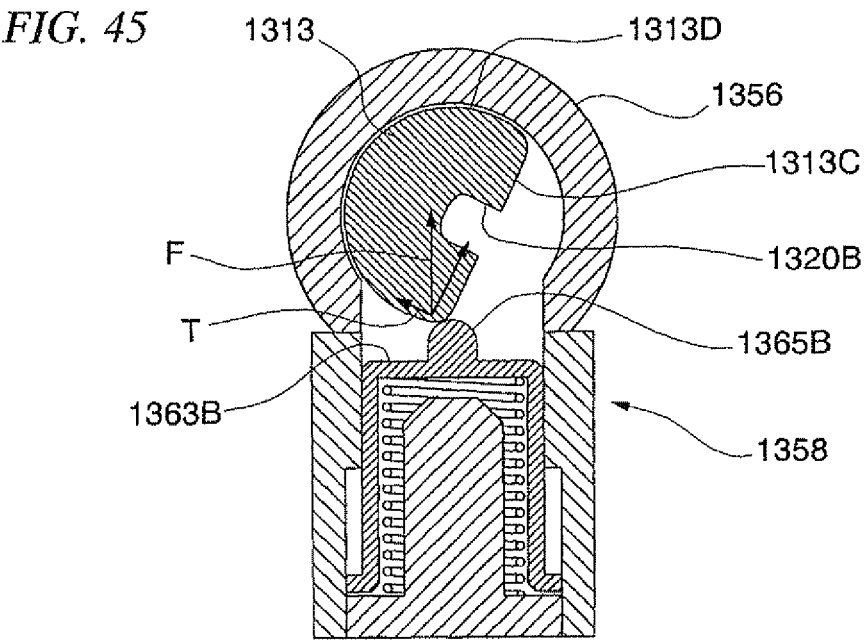
FIG. 45 is a cross-sectional view illustrating movements of a fitting-hole of an attachment section and a fitting-member of a second supporting section.
Figure 46:
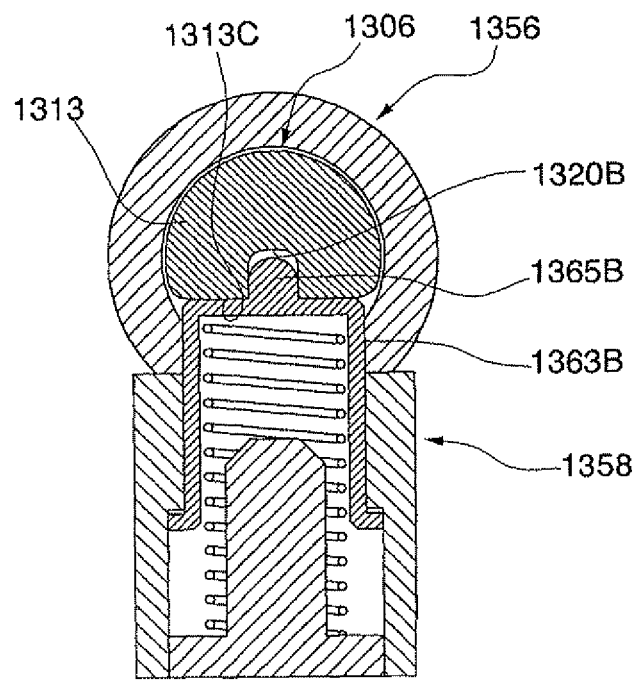
FIG. 46 shows an engaged state between an attachment section and a second supporting section.

FIGS. 45 and 46 are cross-sectional views showing a fitting-hole 1320B of the attachment section 1313, and movement of the fitting protrusion 1363B of the second support section 1358. As previously explained, the outer periphery of the attachment section 1313 corresponding to the part having the fitting-hole 1320B provided thereon has the flat second outer periphery 1313C. In addition, the second outer periphery 1313C in the vicinity of an outer arch periphery 1313D of the attachment section 1313 is formed to have a slightly curved surface which is outwardly convex in a radial direction.

As illustrated in FIG. 45, when the fitting-hole 1320B does not face the fitting protrusion 1365B of the fitting protrusion 1363B, and when the fitting protrusion 1365B makes contact with the second outer periphery 1313C, a part of the urging force F acting on the fitting protrusion 1363B and disintegrated into tangential directions relative to the outer periphery 1313D of the attachment section 1313 acts as torque T which causes the attachment section 1313 to rotate in the direction in which the fitting-hole 1320B approaches the fitting protrusion 1365B. Accordingly, the attachment section 1313 rotates, and as illustrated in FIG. 46, the fitting-hole 1320B faces and engages with the fitting protrusion 1365B; therefore, the second insertion section 1356 and the attachment section 1313 are supported in one unit.

In addition, the torque T causes the attachment section 1313 to rotate, and the reaction force of the torque T causes the second support section 1358 and the second insertion section 1356 to rotate to some extent since the pulley 1306 is supported significantly by the tension of the wire wound therearound in the present embodiment. In addition, the rotation of the attachment section 1313 relative to the second support section 1358 causes the fitting-hole 1320B to face and engage with the fitting protrusion 1365B. Also, the protruding section 1310 of the coil base 1305 and the first insertion section 1355 are supported in the same manner. However, the insertion hole 1360 incapable of rotating relative to the base section 1359 does not make the aforementioned relative rotation; therefore, the fitting protrusion 1365A fits into the fitting-hole 1320A.

Figure 47:
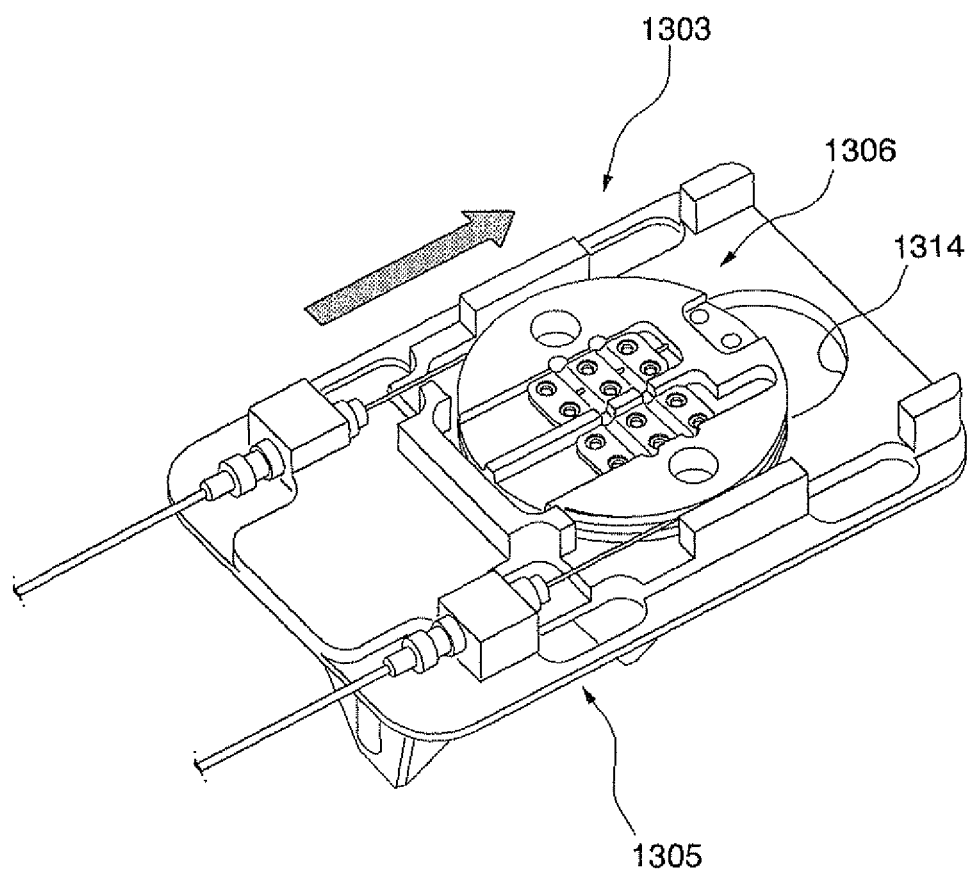
FIG. 47 shows a second wire unit except for a unit cover and a wire cover.

FIG. 47 shows the second-bending-wire unit 1303 except the unit cover 1308 and the wire cover 1307. The shape of the hole section 1314 of the coil base 1305 of the second-bending-wire unit 1303 having substantially the same structure as that of the first wire unit 1301 is set so that the pulley 1306 can move opposite the coil 1304 by a predetermined distance (in a direction indicated by an arrow).

The second-bending-wire unit 1303 is attached to a third mating-attachment section 1366 detachably. The third mating-attachment section 1366 is provided to a mating second bending-operation mechanism 1353 as illustrated in FIG. 37. The third mating-attachment section 1366 has substantially the same structure as that of the aforementioned first-mating attachment section 1354. A second insertion section 1356 having the pulley 1306 inserted therethrough and incapable of rotating relative to the first insertion section 1355 is attached so that the second insertion section 1356 can move toward a second-supporting section by a predetermined distance. The second insertion section of the third mating-attachment section 1366 is connected to a slider 1368 provided to an operation stick 1367 via a transmission member, e.g., a wire which is not shown in the drawing. Drawing the slider 1368 proximally causes the second insertion section and the pulley of the second-bending-wire unit 1303 to move proximally, thereby bending the second bending section 308 of the arm section (see FIG. 36).

Movement of the medical treatment endoscope 1300 having the aforementioned structure in use will be explained as follows. In an example explained here, the operation section 1350 is unsterilized and used repeatedly; and the rest of the components other than the operation section 1350 are sterilized and non-recyclable.

To start with, six wire units having wires extending from the arm sections 302A and 302B connected thereto are connected to the operation section 1350 to allow the operation section 1350 to operate the arm sections 302A and 302B. The sterilized components in this state including the arm sections 302A and 302B which are about to be inserted into the body cavity of a patient must be prevented from making contact with the unsterilized operation section 1350 as much as possible.

Figure 48:
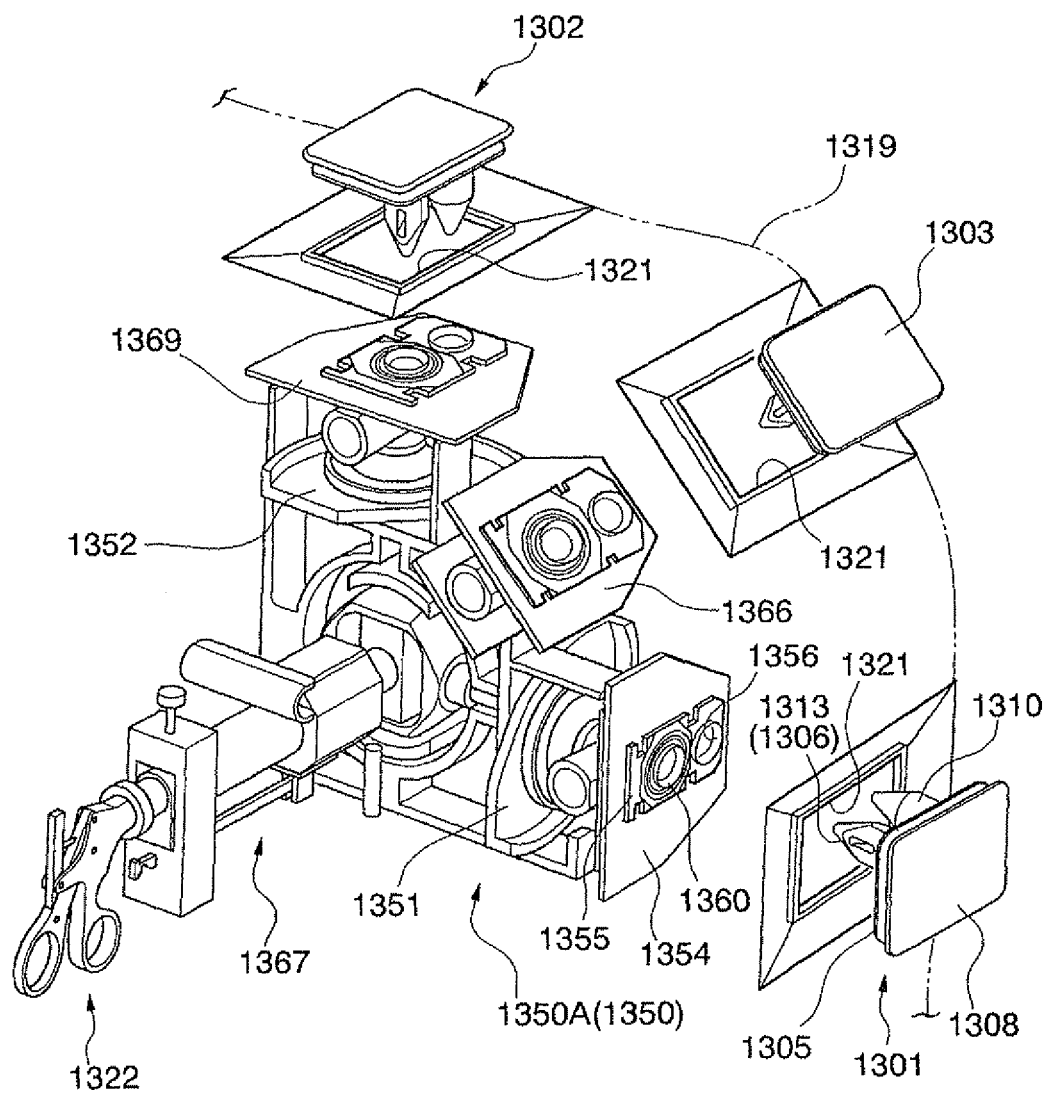
FIG. 48 shows movement of attaching a wire unit to the operation section.

To address this, all the operation section 1350 is covered with the drape 1319 as illustrated in FIG. 48. The drape 1319 has an opening 552A corresponding to the first-mating attachment section 1354 having the first wire unit 1301 attached thereto; the second mating-attachment section 1369 having the second wire unit 1302 attached thereto; and the third mating-attachment section 1366 having the second-bending-wire unit 1303 attached thereto. It should be noted that the second mating-attachment section 1369 attached to the second rotation mechanism 1352 has the same structure as that of the first-mating attachment section 1354. Also, the second operation unit 1350B is covered with the drape 1319 similarly to the first operation unit 1350A shown in FIG. 48.

Subsequently, the first wire unit 1301 is attached to the first-mating attachment section 1354. At the time of attachment, the unit cover 1308 of each wire unit is grasped and pushed so that the protruding section 1310 of the coil base 1305 is inserted into the insertion hole 1360 of the first insertion section 1355; and the attachment section 1313 of the pulley 1306 is inserted into the second insertion section 1356.

Pushing the protruding section 1310 and the attachment section 1313 which axial lines are separated from each other to some extent causes the protruding section 1310 and the attachment section 1313 to be inserted and introduced coaxially into the insertion hole 1360 and the second insertion section 1356, respectively, since this state of the tips of the protruding section 1310 and the attachment section 1313 are tapered and since the insertion hole 1360 and the second insertion section 1356 are chamfered.

Furthermore, movement of the coil base 1305 relative to the unit cover 1308 to some extent absorbs the operational shift caused by inaccurate attachment movement corresponding to the positions of the insertion hole 1360 and the second insertion section 1356 since the unit cover 1308 and the coil base 1305 are in one unit so that the unit cover 1308 and the coil base 1305 can make relative movement to some extent in the longitudinal direction and the width direction with respect to the unit cover 1308. This results in facilitating the insertion of the protruding section 1310 and the attachment section 1313 into the insertion hole 1360 and the second insertion section 1356, respectively.

Figure 49:
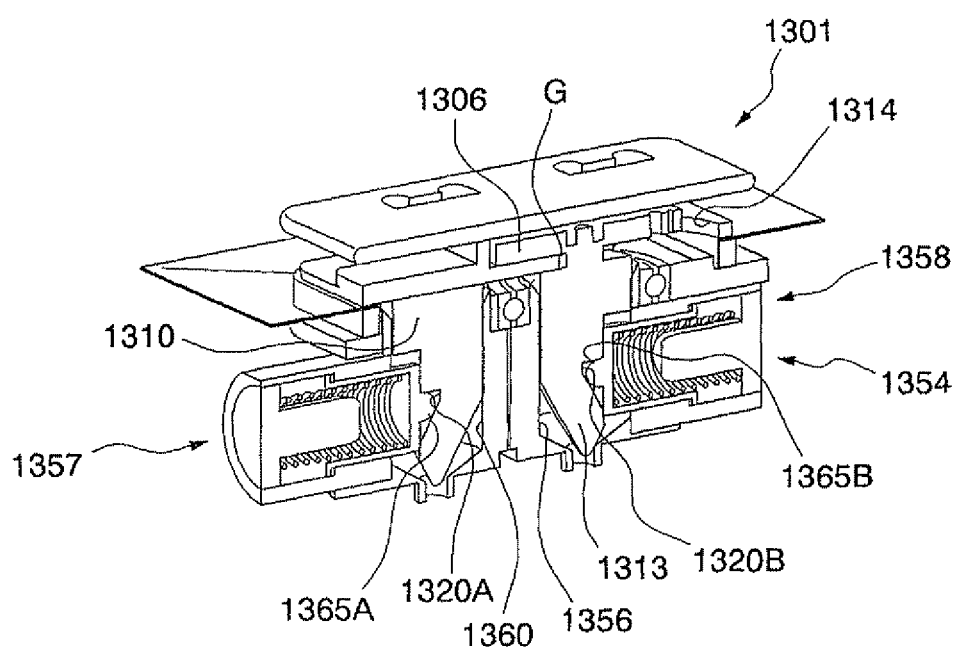
FIG. 49 is a cross-sectional view showing an attached state of the first wire unit to the first mating attachment section.

Further compressing the unit cover 1308 while the protruding section 1310 and the attachment section 1313 are inserted into the insertion hole 1360 and the second insertion section 1356, respectively, causes the fitting-hole 1320A of the protruding section 1310 to engage with the fitting protrusion 1365A of the first support section 1357 as illustrated in FIG. 49. Simultaneously, the movement of the attachment section 1313 relative to the second support section 1358 causes the fitting-hole 1320B to face and engage with the fitting protrusion 1365B. The initial state of the arm sections 302A and 302B is also simultaneously correlated to the initial state of the first rotation mechanism 1351 of the operation section 1350. That is, the correlation of the first wire unit 1301 relative to the first-mating attachment section 1354 is fixed so that initializing the first rotation mechanism 1351 causes the arm sections 302A and 302B to be initialized.

The torque T can cause the pulley 1306 to move relative to the second support section 1358 desirably regardless of the urging member 1364B urging the fitting protrusion 1363B since the second outer periphery 1313C provided corresponding to the fitting-hole 1320B of the attachment section 1313 has a curvature smaller than that of a cylindrical part including the outer periphery 1313D.

Maneuvering the operation section 1350 causes the second insertion section 1356 to be rotated, thereby rotating the pulley 1306, supported by the second support section 1358 in one unit with the second insertion section 1356, synchronously since the first wire unit 1301 is attached to the first-mating attachment section 1354 in one unit.

The distance L1 between the axial line of the insertion hole 1360 of the first insertion section 1355 and the axial line of the second insertion section 1356 is set to be longer than the distance L2 between the axial line of the protruding section 1310 and the axial line of the attachment section 1313 while the pulley 1306 makes close contact with the wall surface of the hole section 1314 in the vicinity (left-hand side in FIG. 44) of the coil 1304 which is provided to the base section 1309 of the coil base 1305 as shown in FIG. 44. Therefore, attaching the first wire unit 1301 to the first-mating attachment section 1354 in one unit causes the pulley 1306 to move in the vicinity of the round hole 1314A, thereby obtaining a space G between the wall surface of the hole section 1314 in the vicinity of the coil 1304 and the pulley 1306, and providing a non-contact state between the base section 1309 and the attachment section 1313. Accordingly, it can prevent the friction force produced between the wall surface of the hole section 1314 in the vicinity of the coil 1304 and the pulley 1306 from providing heavier rotational operation of the first rotation mechanism 1351.

Furthermore, FIG. 46 shows that the attachment section 1313 makes contact with the fitting protrusion 1363B not only at the fitting-hole 1320B but also at the plane section 1313C around the fitting-hole 1320B while the fitting protrusion 1365B engages with the fitting-hole 1320B. Therefore, the rotation of the second support section 1358 synchronous with the rotation of the pulley 1306 increases the area of the second outer periphery 1313C making contact with the fitting protrusion 1363B, thereby reducing the stress acting on the fitting protrusion 1365B and reducing the possibility of damaging the fitting protrusion 1365B and the fitting-hole 1320B. It should be noted that damage to the fitting protrusion 1365B and the fitting-hole 1320B can be prevented more desirably by setting dimensions, e.g., the diameter of the fitting protrusion 1365B so that the area making contact with the second outer periphery 1313C therearound is greater than the area of the end surface of the fitting protrusion 1365B.

FIG. 48 shows the same procedure for attaching the second wire unit 1302 to the second mating-attachment section 1369 and attaching the second-bending-wire unit 1303 to the third mating-attachment section 1366. The same attaching operation is conducted to the second operation unit 1350B which is not shown in the drawing. Accordingly, all the wires of the arm sections 302A and 302B connected to the operation section 1350 allow the operation section 1350 to operate the arm sections 302A and 302B. Subsequently, desirable manipulation is conducted by inserting the procedure instrument 1322 into the operation stick 1367 and conducting the same operation as that of the medical treatment endoscope 501 of the first embodiment.

After the manipulation, the used procedure instrument 1322 is removed from the operation stick 1367 and each wire unit is removed from each mating attachment section. The removals necessitate grasping the unit cover 1308 and retracting the wire units in parallel with the axial lines of the protruding section 1310 and the attachment section 1313. Accordingly, the tapered fitting-holes 1320A and 1320B cause the fitting members 1363A and 1363B of the first support section 1357 and the second support section 1358 to retract gradually toward the fixed sections 1362A and 1362B, respectively, thereby allowing the wire units to be removed.

The operation section 1350 having too complex of a structure to be sterilized is detachable from the wires for operating the arm sections 302A and 302B that are inserted into a human body in the medical treatment endoscope 1300 according to the present embodiment provided with wire units 1301, 1302, and 1303, and mating attachment sections 1354, 1366, and 1369. Therefore, manipulations in more sanitary conditions can be conducted by a sterilized throwaway unit or by sterilizing a unit for reuse for the arm section or an endoscope section.

Also, each wire connected to each wire unit will hardly be contaminated by the operation section 1350 since a part of the unsterilized operation section 1350 does not protrude from the opening 1321 of the drape 1319 covering the operation section 1350, and since sterilized protrusions (e.g., the protruding section 1310 or the attachment section 1313 in the vicinity of each wire unit 1301, 1302, and 1303) are inserted and fixed into the mating attachment sections 1354, 1366, and 1369 inside of the drape 1319, respectively.

Also, each wire unit having substantially the same shape with each other can reduce component variation for production, thereby enabling low-cost mass-production of throwaway unit.

It should be noted that the aforementioned preferred embodiments of the present invention do not limit the present invention. The configuration of the present invention allows for additions, omissions, substitutions and further replacements without departing from the spirit and scope of the present invention.

Figure 50:
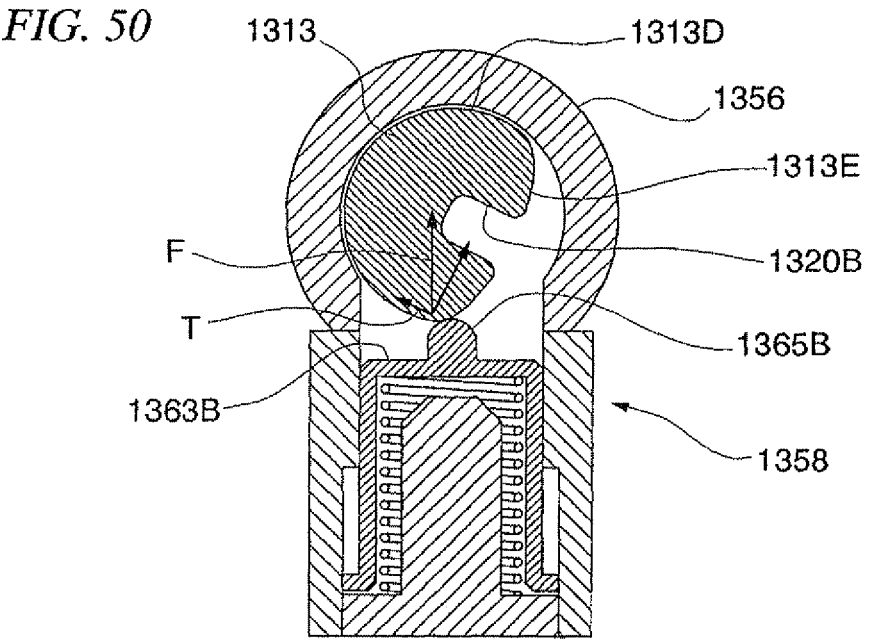
FIG. 50 is a cross-sectional view illustrating movements of a fitting-hole of an attachment section and a fitting-member of a second supporting section in a medical treatment endoscope of a modified example of the present invention.

For example, FIG. 50 shows a modified example in which the second outer periphery may be a second outer periphery 1313E having a curvature smaller than that of the outer periphery including the outer periphery 1313D in contrast to the aforementioned embodiment explaining the example in which the second outer periphery 1313C having the fitting-hole 1320B provided thereon is flat in the second attachment section 1313B of the pulley 1306. Torque T produced similarly in this case can provide smooth fitting of the fitting protrusion 1365B into the fitting-hole 1320B.

Figure 51:
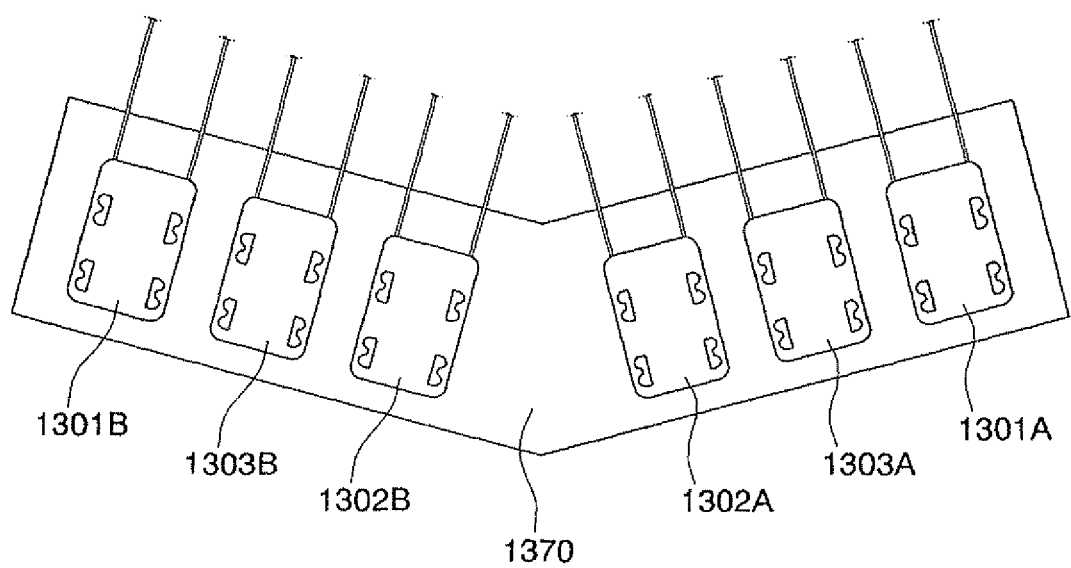
FIG. 51 is a view showing a modified example of the wire unit in the present invention.
Figure 52:
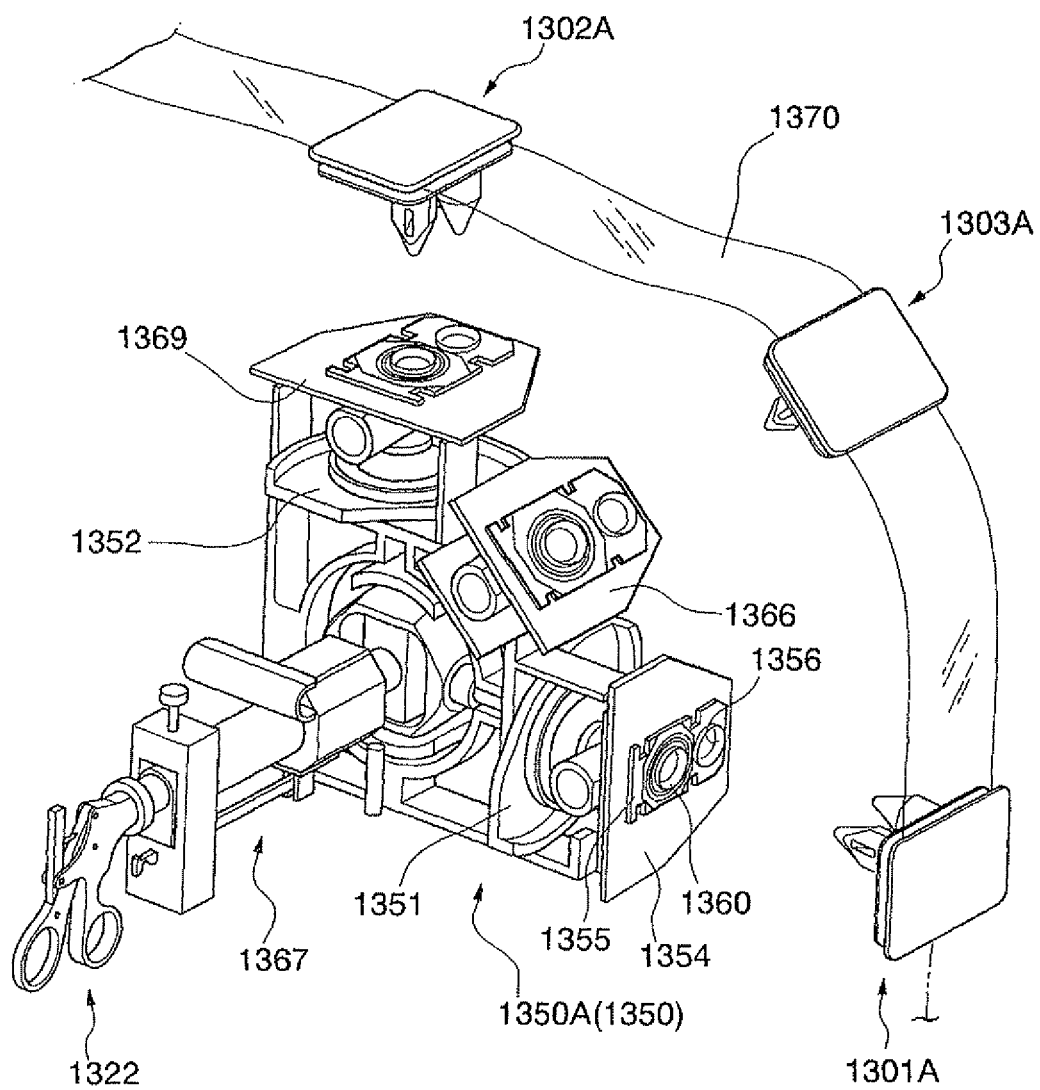
FIG. 52 shows movement of attaching the wire unit to the operation section.

Also, the wire units 1301A, 1302A, 1303A, 1301B, 1302B, and 1303B can be connected by a connection member 1370, e.g., plastic or textile having a constant expandability corresponding to mating attachment sections 1354, 1369, and 1368, respectively in modified examples shown in FIGS. 51 and 52. This can prevent erroneous attachment to a mating attachment section not corresponding to each wire unit. In addition, no longer need for covering the whole operation section with the drape can reduce manipulation-related cost.

In addition, the number of operation units may be varied desirably corresponding to the number of arms of the arm section in contrast to the aforementioned embodiment explaining the example in which the operation section is provided with the first operation unit and the second operation unit. Also, a configuration may be free from the second-bending-wire unit and the third mating attachment section in a case where the arm section is not provided with the second bending part 308.

In addition, the protruding section of the coil base may not have to be formed in D-letter-shape since the attachment hole of the first insertion section is not rotative relative to the base section in contrast to the aforementioned embodiment explaining the example in which both the protruding section of the coil base and the attachment section of the pulley are formed to have a D-letter-shaped cross-section.

Furthermore, it should be noted that the present invention is limited by the scope of claims attached hereto, and not by the aforementioned explanations.

What is claimed is:

1. A medical treatment apparatus comprising:
    an endoscope having a bending part configured to do a first bending motion in a first direction in accordance with a first linear motion of a first transmission member and configured to do a second bending motion in a second direction which is different from the first direction in accordance with a second linear motion of a second transmission member;
    an operation input unit which inputs an operation for actuating the first and the second bending motions in the first and the second direction in the bending part, the operation input unit being configured to be operated by an operator;
    a first axis member which connects and rotatably supports the operation input unit;
    a second axis member crossing the first axis member which connects and rotatably supports the operation input unit;
    a first conversion member being connected to the first axis member, converting a rotation motion of the first axis member to a linear motion, and transmitting the linear motion thereof to the first transmission member;
    a second conversion member being connected to the second axis member at a position distant from the first conversion member, converting a rotation motion of the second axis member to a linear motion, and transmitting the linear motion thereof to the second transmission member;
    a first attaching-detaching mechanism detachably connecting the first conversion member to the first axis member;
    a second attaching-detaching mechanism detachably connecting the second conversion member to the second axis member; and
    a connecting member connecting the first conversion member and the second conversion member with the second conversion member being spaced from the first conversion member, wherein
    the first axis member is configured to be rotated by a tilting movement of the operation input unit in the first direction provided by the operator; and
    the second axis member is configured to be rotated by a tilting movement of the operation input unit in the second direction provided by the operator.

2. The medical treatment apparatus according to claim 1, wherein
    the first conversion member and the second conversion member include a first attachment member, a mating attachment section, a fitting-member, and a fitting-hole, wherein:
    the first attachment member has a cylindrical attachment section, and is attached to an end section of the first transmission member connected to the operation input unit;
    the mating attachment section includes a first mating attachment member, and
    the first mating attachment member is provided to the operation input unit and has an attachment hole into which the cylindrical attachment section of the first attachment member is inserted;
    the fitting-member is provided in the attachment hole of the first mating attachment section, and
    the fitting member is urged so as to protrude relative to an axial line of the attachment hole;
    the fitting-hole is provided on an outer periphery of the cylindrical attachment section, and
    the fitting-hole is capable of engaging with the fitting-member; and
    the outer periphery of the cylindrical attachment section is provided with a first outer periphery and a second outer periphery,
    the second outer periphery has a curvature value smaller than a curvature value of the first outer periphery of the cylindrical attachment section in a cross-section orthogonal to an axial line of the cylindrical attachment section, and
    the first attachment member is attached to the first mating attachment member detachably by engaging the fitting-member into the fitting-hole.

3. The medical treatment apparatus according to claim 2, wherein
    the second outer periphery is formed on a plane which is in parallel with the axial line of the cylindrical attachment section, and
    a cross-section of the cylindrical attachment section passing through the second outer periphery and crossing orthogonally with the axial line of the attachment section has a D-letter shape.

4. The medical treatment apparatus according to claim 2, wherein the fitting-member has:
    a fitting-protrusion, provided to a tip protruding into the attachment hole, for engaging with the fitting-hole; and
    a contact surface having an area greater than an end surface of the fitting-protrusion and making contact with the second outer periphery of the attachment section when the fitting-protrusion engages with the fitting-hole.

5. The medical treatment apparatus according to claim 2, wherein the fitting-hole of the cylindrical attachment section is formed to have a depth which becomes shallower while approaching the tip inserted into the mating attachment member.

6. The medical treatment apparatus according to claim 1, wherein
    the first conversion member and the second conversion member include a second attachment member, a mating attachment section, and a second mating attachment member, wherein:
    the second attachment member has a cylindrical protruding section, and the second attachment member is attached to an end section of the second transmission member connected relative to the operation input unit;

the mating attachment section includes a second mating attachment member, and the second mating attachment member is provided on the operation input unit and has an attachment hole into which the protruding section of the second attachment member is inserted;

the second attachment member has a base having a first tapered protruding section narrowing toward a tip thereof;

a pulley having a second tapered protruding section narrowing toward a tip thereof, the pulley attached to the base being freely rotative, and the pulley having the transmission member wound around therearound; and a cover attached to the base so as to place the pulley between the cover and the base, the second mating attachment member has a first-mating attachment section having a first-attachment hole into which the first protruding section is inserted; and a second-mating attachment section having a second-attachment hole into which the second protruding section is inserted, the freely rotative first-mating attachment member being attached to the second-mating attachment section; and the cover attached to the base is freely movable in a predetermined range relative to the base, and at least a wall surface of the first-attachment hole and the second-attachment hole is chamfered so that depth of the wall surface becomes shallower toward an end section into which the first protruding section or the second protruding section is inserted.

7. The medical treatment apparatus according to claim 6, wherein the second protruding section of the pulley is in non-contact state relative to the base when the second attachment section is attached to the second mating attachment section.

8. The medical treatment apparatus according to claim 1, wherein the connecting member is expandable.

9. The medical treatment apparatus according to claim 1, wherein the first transmission member and the second transmission member are flexible.

* * * * *